United States Patent
Omura et al.

(10) Patent No.: US 6,605,595 B1
(45) Date of Patent: Aug. 12, 2003

(54) AVERMECTIN DERIVATIVES

(75) Inventors: Satoshi Omura, Tokyo (JP); Toshiaki Sunazuka, Tokyo (JP); Andreas Turberg, Haan (DE); Georg von Samson-Himmelstjerna, Solingen (DE); Olaf Hansen, Langenfeld (DE); Achim Harder, Cologne (DE)

(73) Assignee: The Kitasato Institute, Tokyo (JP)

( * ) Notice: Subject to any disclaimer, the term of this patent is extended or adjusted under 35 U.S.C. 154(b) by 0 days.

(21) Appl. No.: 09/890,824

(22) PCT Filed: Feb. 9, 2000

(86) PCT No.: PCT/JP00/00691

§ 371 (c)(1),
(2), (4) Date: Feb. 11, 2002

(87) PCT Pub. No.: WO00/47597

PCT Pub. Date: Aug. 17, 2000

(30) Foreign Application Priority Data

Feb. 9, 1999 (JP) ............................................. 11-031058
Sep. 2, 1999 (JP) ........................................... 11-248633

(51) Int. Cl.[7] ........................ A01N 43/04; A01N 43/02; C07D 305/00
(52) U.S. Cl. .......................... 514/30; 514/450; 549/264
(58) Field of Search .................... 514/30, 450; 549/264

(56) References Cited

U.S. PATENT DOCUMENTS

| | | | | |
|---|---|---|---|---|
| 4,427,663 A | * | 1/1984 | Mrozik ........................ | 424/180 |
| 4,833,168 A | * | 5/1989 | Wyuatt, Jr. ................. | 514/450 |
| 4,895,837 A | * | 1/1990 | Mrozik et al. ............... | 514/30 |
| 4,906,619 A | * | 3/1990 | Eskola et al. ................ | 536/30 |
| 5,030,622 A | * | 7/1991 | Mrozik et al. ............... | 514/30 |
| 5,206,155 A | | 4/1993 | Omura et al. ............... | 435/71.3 |
| 5,369,021 A | | 11/1994 | Satoshi et al. .............. | 435/71.3 |

FOREIGN PATENT DOCUMENTS

| | | |
|---|---|---|
| JP | 3-25467 | 2/1991 |
| JP | 3-74397 | 3/1991 |
| JP | 6-33273 | 5/1994 |
| WO | WO 94/29328 | 12/1994 |

OTHER PUBLICATIONS

Shin, et al., "Cleavage of the Spiroketal Portion of Avermectin . . . ", Tetrahedron Letters, vol. 31 (1990), pp. 3525–3528.

Mrozik, et al., "Avermectin Acyl Derivatives with Anthelmintic Activity", J. Med. Chem., vol. 25 (1982), pp. 658–663.

* cited by examiner

Primary Examiner—Alan L. Rotman
Assistant Examiner—Héctor M. Reyes
(74) Attorney, Agent, or Firm—Fitzpatrick, Cella, Harper & Scinto

(57) ABSTRACT

Avermectin derivatives represented by the general formula (I) or salts thereof:

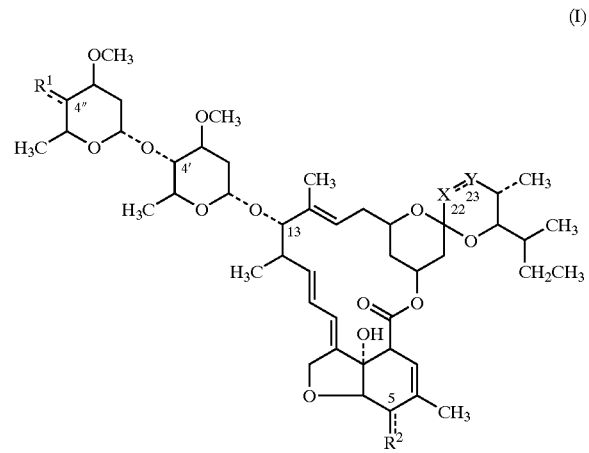

(I)

wherein —X----Y— represents —CH=CH—, —CH$_2$—C(=O)—, —CH$_2$—CH$_2$—, or —CH$_2$—CH(R$^{13}$)—; for example, 1) when —X----Y— represents —CH=CH—, R$^1$ represents (R$^{11}$)(R$^{12}$)C [wherein R$^{11}$ represents a substituted or unsubstituted lower alkyl group; a formyl group; a lower alkoxylcarbonyl group etc.; and R$^{12}$ represents a hydrogen atom or a lower alkyl group]; when the bond between R$^2$ and a carbon atom at the 5-position is a single bond, R$^2$ represents a hydroxyl group or a tri(lower alkyl)silyloxy group; or R$^2$ forms a carbonyl group or a hydroxime group together with the carbon atom at the 5-position; 2) when —X----Y— represents —CH$_2$—C(=O)—, R$^1$ represents (R$^{11a}$)(R$^{12a}$)C [wherein R$^{11a}$ represents a lower alkoxycarbonyl group, or —COOCH$_2$CH=CH$_2$; and R$^{12a}$ represents a hydrogen atom]; and R$^2$ represents a hydroxyl group or a tri(lower alkyl)silyloxy group.

9 Claims, No Drawings

AVERMECTIN DERIVATIVES

This application is a 371 of PCT/JP00/00691 filed Feb. 9, 2000.

TECHNICAL FIELD

The present invention relates to avermectin derivatives having antiparasitic activity.

BACKGROUND ART

Avermectins are antiparasitic antibiotics produced by *Streptomyces avermitilis*. Four main ingredients (A1a, A2a, B1a and B2a) have been known, and among them, avermectin B1a is known to have potent activity (Japanese Patent Unexamined Publication (KOKAI) No. (Hei) 3-254678/1991).

Various derivatives have been synthesized so far to provide avermectin derivatives having higher activity. However, these derivatives fail to have fully satisfactory antiparasitic activity.

DISCLOSURE OF THE INVENTION

An object of the present invention is to provide avermectin derivatives having antiparasitic activity.

In order to find avermectin derivatives having higher antiparasitic activity, the inventors of the present invention synthesized various derivatives using avermectins B1a and B2a as starting materials. As a result, we succeeded in obtaining derivatives represented by the following general formula (I) which have high antiparasitic activity. The present invention was achieved on the basis of the findings.

The present invention thus provides compounds represented by the general formula (I) or salts thereof:

(I)

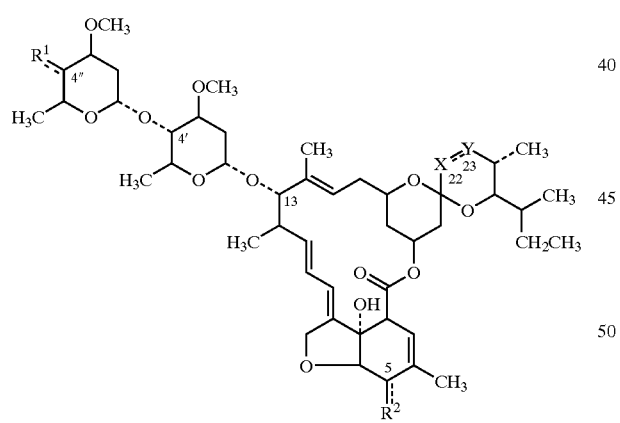

wherein —X----Y— represents —CH=CH—, —CH$_2$—C(=O)—, —CH$_2$—CH$_2$—, or —CH$_2$—CH(R$^{13}$)—;

a line ---- between R$^1$ and a carbon atom at the 4"-position represents a single or double bond;

a line ---- between R$^2$ and a carbon atom at the 5-position represents a single or double bond;

1) when —X----Y— represents —CH=CH—, the line ---- between R$^1$ and a carbon atom at the 4"-position represents a double bond;

R$^1$ represents (R$^{11}$)(R$^{12}$)C [wherein R$^{11}$ represents a substituted or unsubstituted lower alkyl group; a formyl group; a lower alkoxylcarbonyl group, the alkyl moiety of the said lower alkoxylcarbonyl group may be substituted with a heterocyclic group; —CH=N—OR$^3$ wherein R$^3$ represents a hydrogen atom or a lower alkyl group; a lower alkenyloxycarbonyl group; —CH=N—NH—CONH$_2$; a cyano group; —COR$^4$ wherein R$^4$ represents a hydroxyl group or N(R$^5$)(R$^6$) wherein R$^5$ and R$^6$ form a nitrogen containing heterocyclic group together with the adjacent nitrogen atom; a vinyl group substituted with a lower alkenyloxycarbonyl group; —CO—S—CH$_2$—CH$_2$—NH—CO—R$^x$ wherein R$^x$ represents a lower alkyl group; or —CH=CH—COOH; and R$^{12}$ represents a hydrogen atom, or when R$^{11}$ represents a cyano group, R$^{12}$ represents a hydrogen atom or a lower alkyl group]; when the line ---- between R$^2$ and a carbon atom at the 5-position represents a single bond, R$^2$ represents a hydroxyl group, a lower alkoxyl group, or a tri(lower alkyl)silyloxy group; or when the line ---- between R$^2$ and a carbon atom at the 5-position represents a double bond, R$^2$ forms a carbonyl group or a hydroxime group {—C(=NOH)}, together with the carbon atom at the 5-position;

2) when —X----Y— represents —CH$_2$—C(=O)—, the line ---- between R$^1$ and a carbon atom at the 4"-position represents a double bond;

R$^1$ represents (R$^{11a}$)(R$^{12a}$)C [wherein R$^{11a}$ represents a lower alkoxycarbonyl group, the alkyl moiety of the said lower alkoxycarbonyl group may be substituted with a heterocyclic group, or —COOCH$_2$CH=CH$_2$; and R$^{12a}$ represents a hydrogen atom]; the line ---- between R$^2$ and a carbon atom at the 5-position represents a single bond; and R$^2$ represents a hydroxyl group, a lower alkoxyl group, or a tri(lower alkyl)silyloxy group;

3) when —X----Y— represents —CH$_2$—CH$_2$—,

R$^1$ represents (R$^{11b}$)(R$^{12b}$)C [wherein R$^{11b}$ represents a cyano group, a carboxyl group, or a lower alkenyloxycarbonyl group; and R$^{12b}$ represents a hydrogen atom]; or when the line ---- between R$^1$ and a carbon atom at the 4"-position represents a single bond, R$^1$ may represent a carboxymethyl group or a cyanomethyl group; the line ---- between R$^2$ and a carbon atom at the 5-position represents a single bond; and R$^2$ represents a hydroxyl group, a lower alkoxyl group, or a tri(lower alkyl)silyloxy group;

4) when —X----Y— represents —CH$_2$—CH(R$^{13}$)—, the line ---- between R$^1$ and a carbon atom at the 4"-position represents a double bond;

R$^1$ represents (R$^{11c}$)(R$^{12c}$)C [wherein R$^{11c}$ represents a cyano group, a carboxyl group, a lower alkoxycarbonyl group or a lower alkenyloxycarbonyl group; and R$^{12c}$ represents a hydrogen atom]; R$^{13}$ represents a hydroxyl group or a lower alkylcabonyloxy group; the line ---- between R$^2$ and a carbon atom at the 5-position represents a single bond; and R$^2$ represents a hydroxyl group, a lower alkoxyl group or a tri(lower alkyl)silyloxy group.

Among the compounds of the general formula (I) according to the present invention, those wherein —X----Y— is —CH=CH— or the salts thereof are preferred.

Among the compounds of the general formula (I) according to the present invention, those wherein —X----Y— represents —CH=CH—, and R$^{11}$ represents a substituted or unsubstituted lower alkyl group, a cyano group, or —COR$^4$ wherein R$^4$ has the same meaning as that defined above, or the salts thereof are also preferred.

Among the compounds of the general formula (I) according to the present invention, those wherein $R^2$ is a hydroxyl group or a tri(lower alkyl)silyloxy group or the salts thereof are preferred.

Among the compounds of the general formula (I) according to the present invention, those wherein —X----Y— represents —$CH_2$—$CH_2$— or the salts thereof are preferred. Among them, those wherein $R^{11b}$ represents a cyano group or a carboxyl group or the salts thereof are preferred.

According to another aspect of the present invention, there are provided medicaments which comprise as an active ingredient the compound represented by the aforementioned general formula (I) or the physiologically acceptable salt thereof. The medicaments can be administered as antiparasitics to a mammal including a human.

According to further aspects of the present invention, there are provided a use of the compound represented by the aforementioned general formula (I) or the physiologically acceptable salt thereof for the manufacture of the aforementioned medicament; and a method for therapeutic treatment of parasitosis which comprises the step of administering a therapeutically effective amount of the compound represented by the aforementioned general formula (I) or the physiologically acceptable salt thereof to a mammal including a human.

BEST MODE FOR CARRYING OUT THE INVENTION

Hereinafter the compounds represented by the general formula (I) are referred to as the compounds (I). The compounds of other formula numbers are abbreviated in a similar manner.

In the compounds (I) of the present invention, —X----Y— represents —CH=CH—, —$CH_2$—C(=O)—, —$CH_2$—$CH_2$—, or —$CH_2$—CH($R^{13}$)— (in each formula, the carbon atom on the left side corresponds to X.).

In the compounds (I) of the present invention, the compounds, wherein $R^2$ is a hydroxyl group or a tri(lower alkyl)silyloxy group when —X----Y— represents —CH=CH— and the line ---- between $R^2$ and a carbon atom at the 5-position represents a single bond, are referred to as the compounds (Ia), and those wherein —X----Y— represents —CH=CH— and $R^2$ forms a carbonyl group or a hydroxime group together with the carbon atom at the 5-position are referred to as the compounds (Ic).

In the compounds (I) of the present invention, the compounds wherein —X----Y— represents —$CH_2$—C(=O)—, the line ---- between $R^2$ and a carbon atom at the 5-position represents a single bond, and $R^2$ represents a hydroxyl group or a tri(lower alkyl)silyloxy group are referred to as the compounds (Ib).

In the compounds (I) of the present invention, the compounds wherein —X----Y— represents —$CH_2$—$CH_2$—, the line ---- between $R^2$ and a carbon atom at the 5-position represents a single bond, and $R^2$ represents a hydroxyl group or a tri(lower alkyl)silyloxy group are sometimes referred to particularly as "ivermectin derivatives." "Avermectin derivatives" referred to in the specification include the aforementioned ivermectin derivatives.

In the compounds (I) of the present invention, the compounds wherein —X----Y— represents —$CH_2$—CH($R^{13}$)— wherein $R^{13}$ represents a hydroxyl group or a lower alkylcarbonyloxy group, the line ---- between $R^2$ and a carbon atom at the 5-position represents a single bond, and $R^2$ represents a hydroxyl group or a tri(lower alkyl)silyloxy group are sometimes referred to as the compounds (Id).

In the definition of each group in the compounds (I), the lower alkyl group may be any of $C_1$–$C_8$ linear, branched, and cyclic alkyl groups or a combination thereof, preferably a $C_1$–$C_8$ linear or branched alkyl group. The lower alkyl group includes, for example, a methyl group, ethyl group, propyl group, isopropyl group, cyclopropyl group, butyl group, isobutyl group, sec-butyl group, tert-butyl group, cyclopropylmethyl group, cyclobutyl group, pentyl group, hexyl group, heptyl group, octyl group, and the like. A lower alkyl moiety in functional groups having the lower alkyl moiety, such as the lower alkoxycarbonyl group, lower alkoxyl group, lower alkylcarbonyloxy group and tri(lower alkyl)silyloxy group has the same meaning as that defined in the aforementioned lower alkyl group unless otherwise specifically mentioned. The lower alkyl moieties in the tri(lower alkyl)silyloxy group may be the same or different.

Examples of a lower alkenyl moiety in the lower alkenyloxycarbonyl group include $C_2$–$C_6$ straight and branched alkenyl groups, for example, a vinyl group, allyl group, methacryl group, butenyl group, pentenyl group, hexenyl group, and the like. The number of double bonds present in the alkenyl group is not particularly limited, and preferably one.

The heterocyclic group may be either an aromatic or aliphatic heterocyclic group. Examples of the aromatic heterocyclic group include, for example, a 5- or 6-membered monocyclic aromatic heterocyclic group which contains at least one heteroatom selected from the group consisting of nitrogen, oxygen, and sulfur atoms. More specifically, examples include a pyridyl group, pyrrolyl group, furyl group, thienyl group, thiazolyl group, pyrazinyl group, imidazolyl group, pyrazolyl group, triazolyl group, tetrazolyl group, and oxazolyl group. Examples of the aliphatic heterocyclic group include, for example, a 5- or 6-membered monocyclic aliphatic heterocyclic group which contains at least one heteroatom selected from the group consisting of nitrogen, oxygen, and sulfur atoms. More specifically, examples include a pyrrolidinyl group, tetrahydrofuryl group, and tetrahydropyranyl group.

The nitrogen containing heterocyclic group formed together with the adjacent nitrogen atom includes a morpholino group, thiomorpholino group, piperidino group, 1-piperazinyl group, and 1-pyrrolidinyl group.

The type and number of the substituent of the substituted alkyl group are not particularly limited. Preferably, the number of the substituent is from 1 to 3, and examples include a hydroxyl group, a halogen atom ("a halogen atom" used herein may be any of fluorine, chlorine, bromine, and iodine atoms), an amino group, a hydroxyamino group, a mono(lower alkyl)amino group, a mono(lower alkoxy) amino group, an alkanoylamino group, an azide group, a heterocyclic group (examples include those exemplified for the aforementioned heterocyclic group and the nitrogen containing heterocyclic group formed together with the adjacent nitrogen atom), a lower alkanoyloxy group, a heterocyclic carbonyloxy group(i.e., heterocycle-C(=O)—O wherein the heterocyclic moiety has the same meaning as that defined in the aforementioned heterocyclic group and the heterocyclic moiety may be substituted with a halogen atom or a lower alkoxycarbonyl group), and a heterocyclic oxy group such as tetrahydropyranyloxy group.

In the definition of the substituent of the substituted lower alkyl group, a lower alkyl moiety of the mono(lower alkyl) amino group, mono(lower alkoxy)amino group, alkanoylamino group, lower alkanoyloxy group and lower alkoxycarbonyl group has the same meaning as that defined in the aforementioned lower alkyl group.

Examples of the salt of the compounds (I) include acid-addition salts, metal salts, ammonium salts, and organic amine-addition salts. Examples of the acid-addition salts include inorganic acid salts such as hydrochlorides, sulfates, nitrates and phosphates, and organic acid salts such as acetates, maleates, fumarates and citrates. Examples of the metal salts include alkali metal salts such as sodium salts and potassium salts, alkaline-earth metal salts such as magnesium salts and calcium salts, aluminium salts, and zinc salts. Examples of the ammonium salts include ammonium salts and tetramethylammonium salts, and examples of the organic amine-addition salts include salts with morpholine and piperidine. When a salt of the compound (I) is used as an active ingredient of the medicament of the present invention, a physiologically acceptable salt is preferably used.

Preparations of the compounds (I) will be explained below.

Avermectins B1a and B2a, which are used as starting materials for the avermectin derivatives disclosed in the present invention, are isolated from the culture of *Streptomyces avermitilis*, and they are known compounds (Japanese Patent Unexamined Publication (KOKAI) Nos. (Hei) 3-74397/1991 and 3-254678/1991, and U.S. Pat. No. 5,206,155 and the like.)

In the present invention, 5-O-tri(lower alkyl)silyl-4"-oxoavermectin B1a (the compounds (IIa)), which are starting materials for the preparation of the compounds (Ia), can be synthesized by using avermectin B1a as a starting material according to the method disclosed in Japanese Patent Examined Publication (KOKOKU) No. (Hei) 6-33273/1994 or a similar method thereto. Specifically, the compounds (IIa) used as the starting material can be obtained by subjecting the hydroxyl group at the 5-position of avermectin B1a to tri(lower alkyl)silylation, and then oxidizing the hydroxyl group at the 4"-position. Examples of oxidations other than the method disclosed in Japanese Patent Examined Publication (KOKOKU) No. (Hei) 6-33273/1994 include oxidation with phenyl dichlorophosphate ($PhOPOCl_2$)/triethylamine (TEA)/dimethylsulfoxide (DMSO) in isopropyl acetate, oxidation with tetrapropylammonium perruthenate ($Pr_4NRuO_4$)/4-methylmorpholine N-oxide (NMO) in the presence of Molecular Sieves 4A (MS4A) in methylene chloride, and oxidation with sulfur trioxide/pyridine complex in dimethylsulfoxide (DMSO).

5-O-Tri(lower alkyl)silyl-4",23-dioxoavermectin B2a (the compounds (IIb)), which are starting materials for the preparation of the compounds (Ib), can be obtained by using avermectin B2a as a starting material according to the method disclosed in Japanese Patent Unexamined Publication (KOKAI) No. (Hei) 3-74397/1991 or a similar method thereto, which method comprises the step of producing 5-O-tri(lower alkyl)silylavermectin B2a and the following oxidation at the 23- and 4"-positions.

In the following preparations, when a defined group is changed under conditions for a method to be applied, or the group is unsuitable for carrying out the method, desired compounds can be obtained by employing introduction and elimination of a protective group conventionally used in synthetic organic chemistry [see, for example, Protective Groups in Organic Synthesis, T. W. Greene, John Wiley & Sons Inc. (1981)].

Preparation 1

Among the compounds (I), the compound wherein —X----Y— is —CH=CH— or —$CH_2$—C(=O)—, $R^1$ is a lower alkoxycarbonylmethylidene group optionally substituted with a heterocyclic group, a lower alkenyloxycarbonylmethylidene group, or a cyanomethylidene group, and $R^2$ is a tri(lower alkyl)silyloxy group (the compounds (IIIa) and (IIIb)) can be prepared by the process set out below:

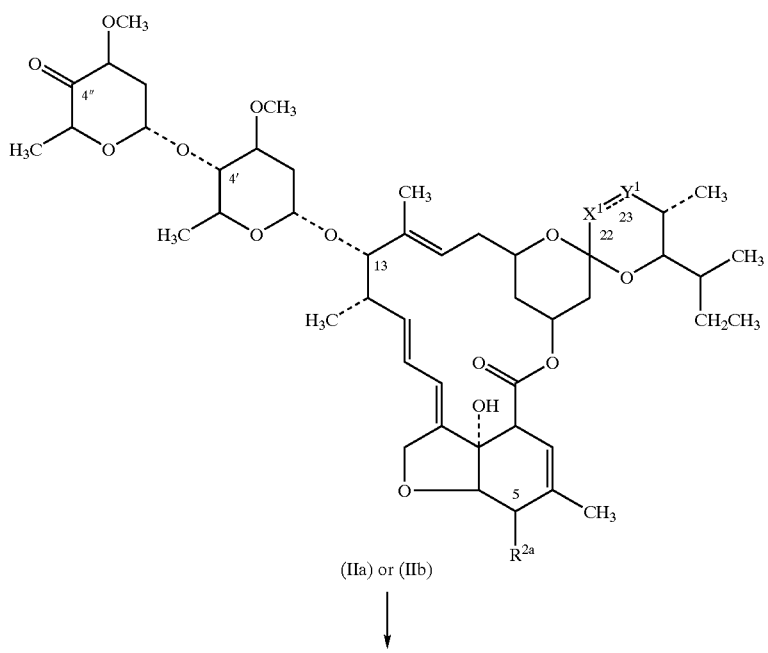

(IIa) or (IIb)

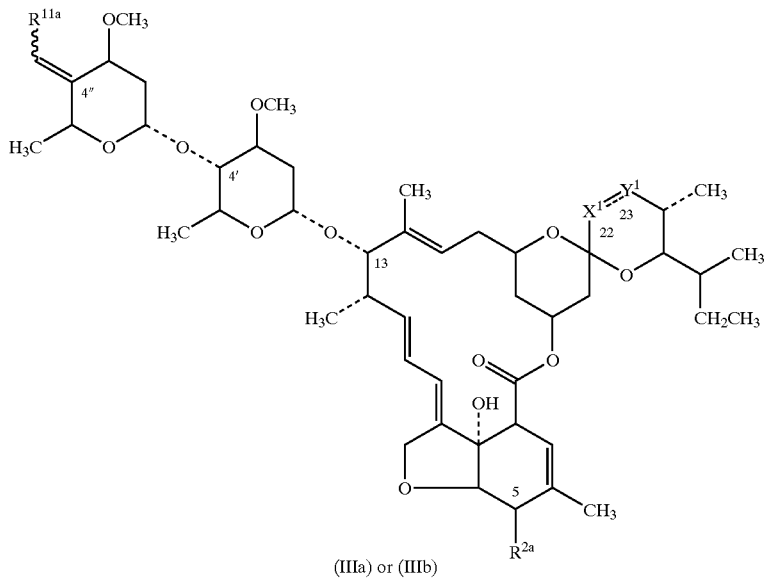

(IIIa) or (IIIb)

(In the scheme, $R^{11a}$ represents a lower alkoxycarbonyl group optionally substituted with a heterocyclic group, a lower alkenyloxycarbonyl group, or a cyano group among the definition of $R^{11}$; $R^{2a}$ represents a tri(lower alkyl)silyloxy group among the definition of $R^2$; and —$X^1$----$Y^1$— represents —CH=CH— or —CH$_2$—C(=O)—.)

The compound (IIIa) or (IIIb) can be obtained by reacting the compound (IIa) or (IIb) with 1 to 10 equivalents of a compound (IV) represented by the formula: (RO)$_2$P(O)CH$_2$R$^{11a}$ wherein R represents a lower alkyl group having the same meaning as that defined above and $R^{11a}$ has the same meaning as that defined above, in the presence of 1 to 10 equivalents of a base in an inert solvent at a temperature ranging from −78° C. to a boiling point of a solvent used for 1 minute to 24 hours.

As the inert solvent, tetrahydrofuran, ether, benzene, toluene, and the like can be used alone or as a mixture thereof. Examples of the base include potassium tert-butoxide, sodium hydride, potassium hydride, lithium hexamethyldisilazane, and lithium diisopropylamide.

The compound (IIIa) wherein —X----Y— is —CH=CH—, $R^{11}$ is a lower alkoxycarbonyl group optionally substituted with a heterocyclic group and $R^2$ is a tri(lower alkyl)silyloxy group can also be obtained using as a starting material the compound (VIIa) wherein —X----Y— is —CH=CH—, $R^{11}$ is a carboxyl group and $R^2$ is a tri(lower alkyl)silyloxy group which is obtained in Preparation 4 explained below.

The reaction can be carried out by reacting the compound (VIIa) with a corresponding lower alcohol optionally substituted with a heterocyclic group or an ester of a corresponding lower alcohol optionally substituted with a heterocyclic group in the presence or absence of a base in an inert solvent at a temperature ranging from 0° C. to a boiling point of a solvent used for one minute to 3 days to prepare the desired compounds.

As the inert solvent, lower alcohols such as methanol, ethanol, propanol and tert-butanol, tetrahydrofuran, ether, chloroform, methylene chloride, 1,2-dichloroethane, and the like may be used. The corresponding lower alcohol optionally substituted with a heterocyclic group or the ester of the corresponding lower alcohol optionally substituted with a heterocyclic group, per se, may be used as the inert solvent.

As the base, N-ethyl diisopropylamine, triethylamine, pyridine, 4-dimethylaminopyridine, and the like may be used.

Preparation 2

Among the compounds (I), the compound wherein —X----Y— is —CH=CH—, $R^{11}$ is a hydroxymethyl group, and $R^2$ is a tri(lower alkyl)silyloxy group (the compound (Va)) can be prepared by the process set out below:

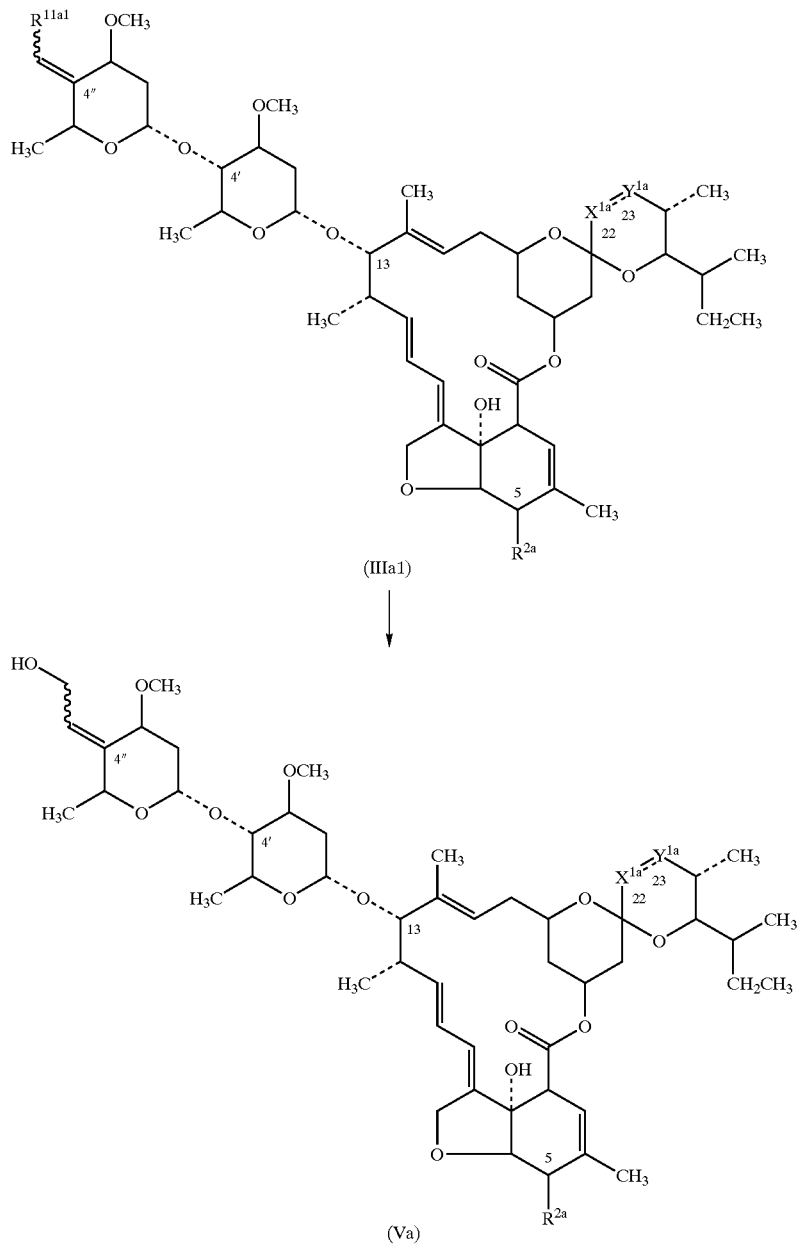

(In the scheme, $R^{11a1}$ represents a lower alkoxycarbonyl group optionally substituted with a heterocyclic group, or a lower alkenyloxycarbonyl group among the definition of $R^{1a}$; —$X^{1a}$----$Y^{1a}$— represents —CH=CH—, and $R^{2a}$ has the same meaning as that defined above.)

The compound (Va) can be obtained by treating the compound wherein $R^{11a}$ is a lower alkoxycarbonyl group optionally substituted with a heterocyclic group, or a lower alkenyloxycarbonyl group, and —$X^1$----$Y^1$— is —CH=CH— (compound (IIIa1) among the compounds obtained in Preparation 1 with an equivalent to an excess amount of a reducing agent in an inert solvent at a temperature ranging from −78° C. to a boiling point of a solvent used for 1 minute to 24 hours.

As the inert solvent, methanol, ethanol, water, tetrahydrofuran, ether, benzene, toluene, pyridine, hexane, methylene chloride, chloroform, 1,2-dichloroethane, and the like may be used alone or as a mixture thereof. Examples of the reducing agent include sodium borohydride, lithium aluminium hydride, and diisobutylaluminium hydride.

The compounds wherein $R^{11}$ is a halomethyl group can be prepared by treating the compound obtained above wherein $R^{11}$ is a hydroxymethyl group with a halogenating agent in the presence or absence of a base in an inert solvent at a temperature ranging from −78° C. to a boiling point of a solvent used for 1 minute to 24 hours.

As the inert solvent, methylene chloride, chloroform, 1,2-dichloroethane, benzene, ether, tetrahydrofuran, and the like may be used alone or as a mixture thereof. As the halogenating agent, p-toluenesulfonyl chloride, thionyl chloride, thionyl bromide, and the like may be used. As the base, N-ethyl diisopropylamine, triethylamine, pyridine, 4-dimethylaminopyridine, and the like may be used.

The compounds wherein $R^{11}$ is an aminomethyl group can also be prepared by reacting the compound wherein $R^{11}$ is a halomethyl group with an azide-formation agent in an inert solvent at a temperature ranging from −78° C. to a boiling point of a solvent used for 1 minute to 24 hours and carrying out reduction in a conventional manner.

Sodium azide, potassium azide, and the like may be used as the azide-formation agent.

As the inert solvent, ether, tetrahydrofuran, and the like may be used alone or as a mixture thereof.

Preparation 3

Among the compounds (I), the compound wherein —X----Y— is —CH=CH—, $R^{11}$ is a formyl group, and $R^2$ is a tri(lower alkyl)silyloxy group (the compound (VIa)) can be prepared by the process set out below:

(In the scheme, $R^{2a}$ and —$X^{1a}$----$Y^{1a}$— have the same meanings as those defined above.)

The compound (VIa) can be obtained by treating the compound (Va) obtained in Preparation 2 with an equivalent to an excess amount of an oxidizing agent in an inert solvent at a temperature ranging from −78° C. to a boiling point of a solvent used for 1 minute to 24 hours.

As the inert solvent, water, tetrahydrofuran, ether, benzene, hexane, methylene chloride, chloroform, 1,2-dichloroethane, tert-butanol, and the like may be used alone or as a mixture thereof. Examples of the oxidizing agent include pyridinium chlorochromate, pyridinium dichromate, manganese dioxide, and potassium permanganate.

The compound (VIa) wherein the lower alkoxycarbonyl group optionally substituted with a heterocyclic group or the

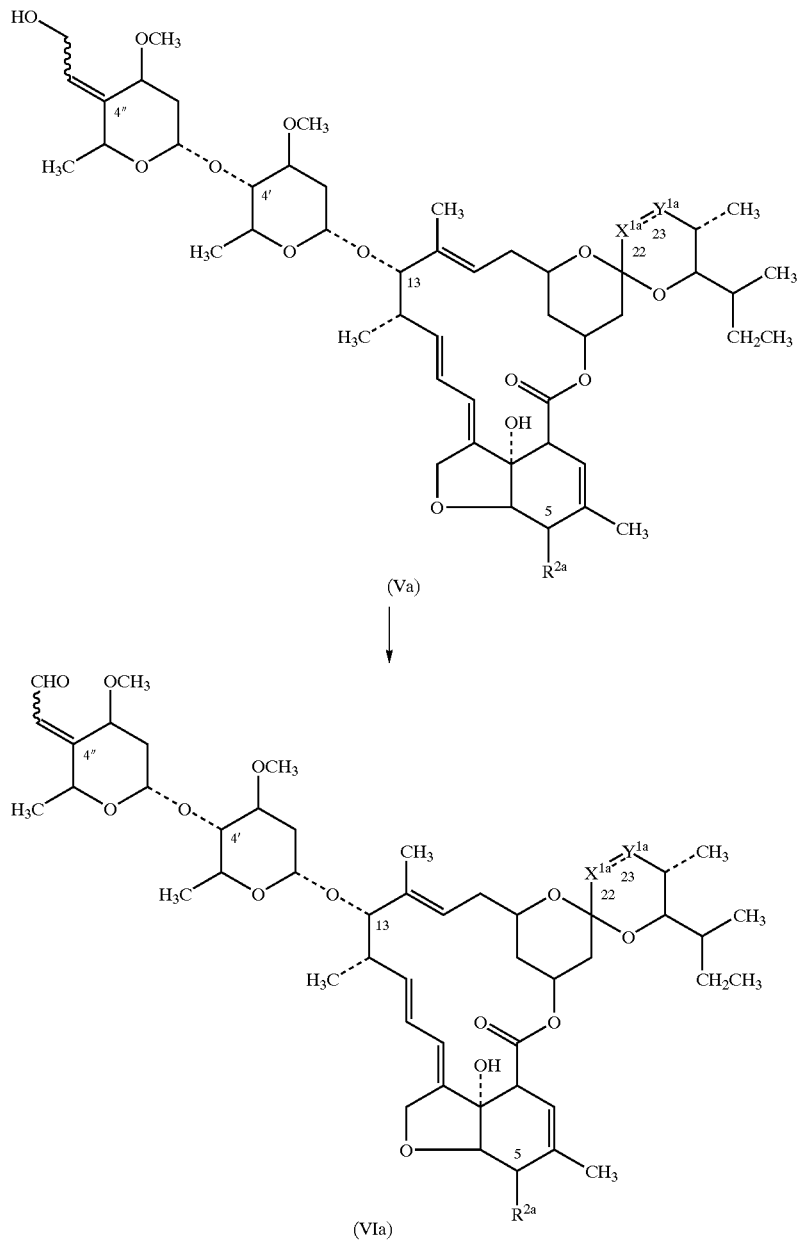

lower alkenyloxycarbonyl group is converted into a formyl group can also be obtained by controlling reaction conditions for reduction of the lower alkoxycarbonyl group optionally substituted with a heterocyclic group or the lower alkenyloxycarbonyl group of the compound (IIIa1) which is used as a starting material in Preparation 2. Examples of the reaction solvent, the reducing agent, equivalents of the reducing agent, the reaction time and the reaction temperature for the reduction of the compound (IIIa1) to obtain the compound (VIa) include those exemplified in Preparation 2.

The compound wherein $R^{11}$ is a vinyl group or a substituted vinyl group (e.g., $R^{11}$ is —CH=CH—COOH) can be prepared by subjecting the compound obtained above wherein $R^{11}$ is a formyl group to the Wittig reaction.

Examples of the solvent, the reaction temperature, equivalents of the reagent, the reaction time and the like for the Wittig reaction are similar to those described in Preparation 1.

Preparation 4

Among the compounds (I), the compound wherein —X----Y— is —CH=CH—, $R^{11}$ is a carboxyl group, and $R^2$ is a tri(lower alkyl)silyloxy group (the compound (VIIa)) can be prepared by the process set out below:

dinium chlorochromate, Jones reagent, chromium trioxide, and potassium permanganate.

The compound (VIIa) can also be obtained by oxidizing the formyl group of the compound (VIa) obtained in Preparation 3 according to the method for preparing the compound (VIIa) from the compound (Va).

The compound (VIIa) can also be obtained by hydrolyzing the compound (IIIa) obtained in Preparation 1 in the presence of an equivalent to an excess amount of an acid or a base in an inert solvent. Examples of the inert solvent include methanol, ethanol, water, tetrahydrofuran, ether, and acetonitrile. Examples of the acid include hydrochloric acid, sulfuric acid, and nitric acid, and examples of the base include sodium hydroxide, potassium hydroxide, and lithium hydroxide.

The compound (VIIa) can also be obtained by treating the compound wherein $R^{11a}$ is a lower alkenyloxycarbonyl group among the compound (IIIa) obtained in Preparation 1 with an equivalent to an excess amount of a reducing agent in the presence of a palladium catalyst in an inert solvent at a temperature ranging from −78° C. to a boiling point of a solvent used for 1 minute to 24 hours. Examples of the inert solvent include methanol and ethanol, and examples of the reducing agent include sodium borohydride, formic acid and hydrazine. Examples of the palladium catalyst include tetrakis(triphenylphosphono)palladium.

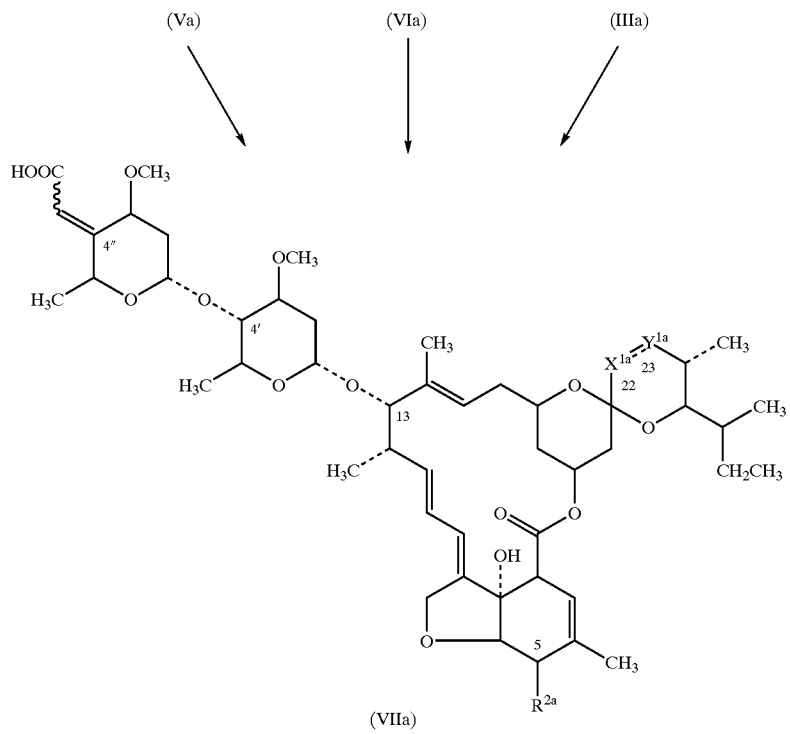

(In the scheme, $R^{2a}$ and —$X^{1a}$----$Y^{1a}$— have the same meanings as those defined above.)

The compound (VIIa) can be obtained by treating the compound (Va) obtained in Preparation 2 with an equivalent to an excess amount of an oxidizing agent in an inert solvent at a temperature ranging from −78° C. to a boiling point of a solvent used for 1 minute to 24 hours. As the inert solvent, water, tetrahydrofuran, ether, benzene, hexane, chloroform, methylene chloride, 1,2-dichloroethane, tert-butanol, and the like may be used alone or as a mixture thereof. Examples of the oxidizing agent include pyridinium dichromate, pyri- The compound wherein $R^{11}$ is —CO—S—$CH_2$—$CH_2$—NH—CO—$R^x$ ($R^x$ has the same meaning as that defined above) can be prepared by further reacting the compound obtained above wherein $R^{11}$ is a carboxyl group with HS—$CH_2$—$CH_2$—NH—CO—$R^x$ ($R^x$ has the same meaning as that defined above).

For the preparation of the compound wherein $R^{11}$ is —CO—S—$CH_2$—$CH_2$—NH—CO—$R^x$ ($R^x$ has the same meaning as that defined above) from the compound wherein $R^{11}$ is a carboxyl group, reaction is generally carried out in the presence of a condensing agent and a base.

Examples of the solvent and the base used in the preparation of the compound wherein $R^{11}$ is —CO—S—CH$_2$—CH$_2$—NH—CO—R$^x$ (R$^x$ has the same meaning as that defined above) from the compound wherein $R^{11}$ is a carboxyl group include the inert solvents and the bases used in the reaction of the compounds (VIIa) and (XV) in Preparation 9 explained below.

As the condensing agent, benzotriazol-1-yloxytripyrrolidinophosphonium hexafluorophosphate and the like, as well as the condensing agents used in the reaction of the compounds (VIIa) and (XV) in Preparation 9 explained below, may be used.

Examples of the reaction time, the reaction temperature, equivalents of the reagent, and the like for the preparation of the compound wherein $R^{11}$ is —CO—S—CH$_2$—CH$_2$—NH—CO—R$^x$ (R$^x$ has the same meaning as that defined above) from the compound wherein $R^{11}$ is a carboxyl group are similar to those used in the reaction of the compounds (VIIa) and (XV) in Preparation 9 explained below.

Preparation 5

Among the compounds (I), the compound wherein —X----Y— is —CH=CH—, $R^{11}$ is a lower alkanoyloxymethyl group, or a heterocyclic carbonyloxymethyl group: heterocycle-C(=O)—O—CH$_2$— wherein the heterocyclic moiety has the same meaning as that defined in the aforementioned heterocyclic group and may be substituted with a halogen atom or a lower alkoxycarbonyl group, and $R^2$ is a tri(lower alkyl)silyloxy group (the compound (IXa)) can be obtained by the following method.

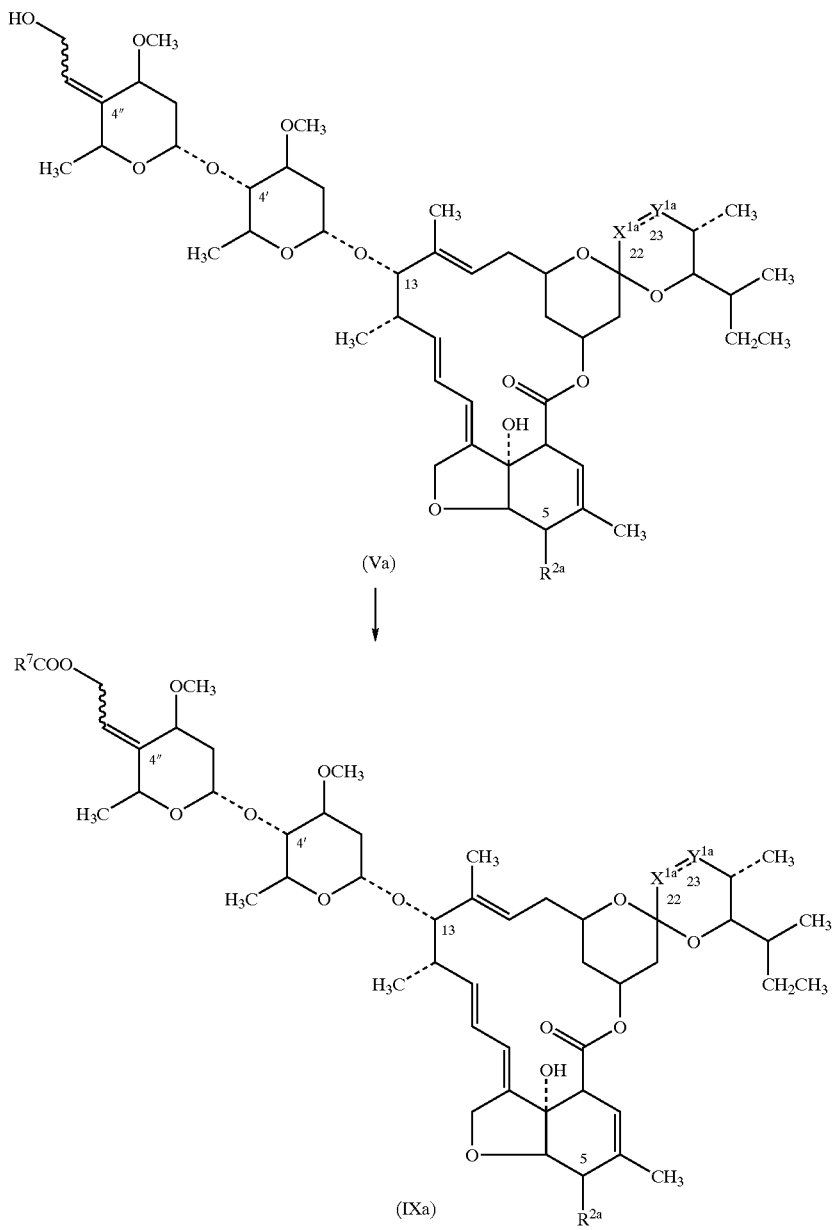

(In the scheme, $R^7$ represents a lower alkyl group or a heterocyclic group which may be substituted with a halogen atom or a lower alkoxycarbonyl group; $R^{2a}$ and —$X^{1a}$—$Y^{1a}$— have the same meanings as those defined above. The lower alkyl group, heterocyclic group, halogen atom and lower alkoxycarbonyl group in the definition of $R^7$ have the same meanings as those defined above, respectively.)

The compound (IXa) can be obtained by reacting the compound (Va) obtained in Preparation 2 with an equivalent to an excess amount of the compound (VIIIa) represented by the formula: $R^7COCl$ wherein $R^7$ has the same meaning as that defined above, in the presence or absence of an equivalent to an excess amount of a base in an inert solvent at a temperature ranging from −78° C. to a boiling point of a solvent used for 1 minute to 24 hours. Examples of the inert solvent include chloroform, methylene chloride, 1,2-dichloroethane and pyridine, and examples of the base include triethylamine, diisopropylethylamine, pyridine, and dimethylaminopyridine.

The desired compound (IXa) can also be obtained by reacting the compound (Va) with an equivalent to an excess amount of the compound (VIIIb) represented by the formula: $(R^7CO)_2O$ wherein $R^7$ has the same meaning as that defined above, in the presence or absence of an equivalent to an excess amount of a base in an inert solvent at a temperature ranging from −78° C. to a boiling point of a solvent used for 1 minute to 24 hours. Examples of the inert solvent and the base used include those used in the reaction of the compounds (Va) and (VIIIa).

The desired compound (IXa) can alternatively be obtained by reacting the compound (Va) with an equivalent to an excess amount of the compound (VIIIc) represented by the formula: $R^7COOH$ wherein $R^7$ has the same meaning as that defined above, for 1 minute to 24 hours in the presence or absence of an equivalent to an excess amount of a base and in the presence of an equivalent to an excess amount of a condensing agent in an inert solvent at a temperature ranging from −78° C. to a boiling point of a solvent used. Examples of the inert solvent and the base used include those used in the reaction of the compounds (Va) and (VIIIa). Examples of the condensing agent include 1-ethyl-3-(3-dimethylaminopropyl)carbodiimide (WSCI) hydrochloride and 1,3-dicyclocarbodiimide.

Preparation 6

Among the compounds (I), the compound wherein —X—-Y— is —CH=CH—, $R^{11}$ is —CH=N—$OR^3$ wherein $R^3$ has the same meaning as that defined above, or —CH=N—NH—$CONH_2$, and $R^2$ is a tri(lower alkyl) silyloxy group (the compound (XIa)) can be obtained by using the compound (VIa) obtained in Preparation 3 as a starting material by the following method.

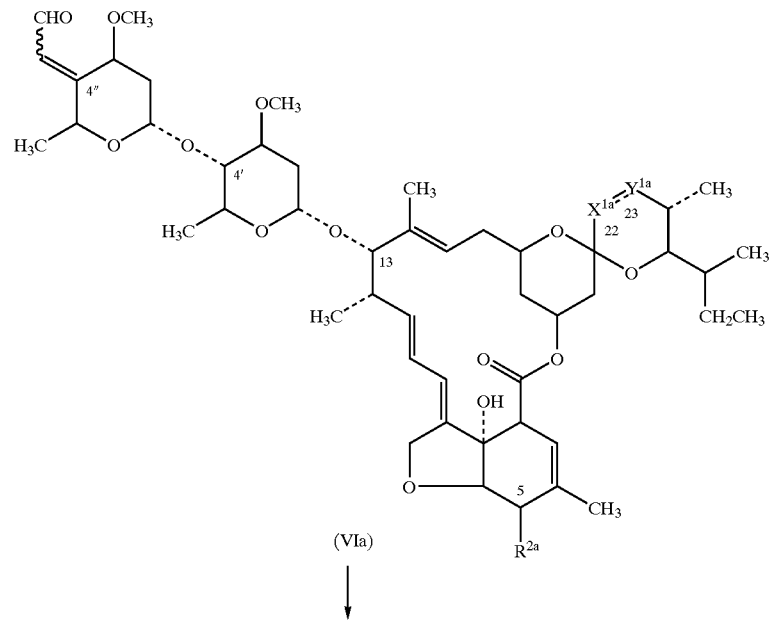

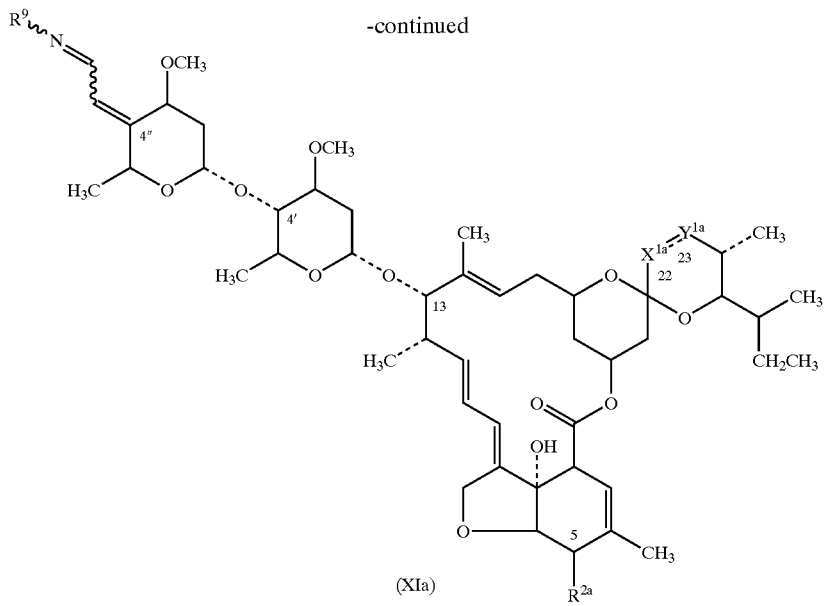

(XIa)

(In the scheme, $R^9$ represents $OR^3$ wherein $R^3$ has the same meaning as that defined above, or $NH—CONH_2$, and $R^{2a}$ and $—X^{1a}----Y^{1a}—$ have the same meanings as those defined above.)

The compound (XIa) can be obtained by reacting the compound (VIa) with an equivalent to an excess amount of the compound (X) represented by the formula: $H_2N—OR^3$ wherein $R^3$ has the same meaning as that defined above or a salt thereof (examples thereof include acid addition salts having the same meaning as that defined above), or an equivalent to an excess amount of a semicarbazide or a salt thereof (examples thereof include acid addition salts having the same meaning as that defined above) for 1 minute to 24 hours in the presence or absence of an equivalent to an excess amount of a base in an inert solvent at a temperature ranging from −78° C. to a boiling point of a solvent used. Examples of the inert solvent include methanol and ethanol.

Examples of the base include pyridine, triethylamine, and dimethylaminopyridine.

The compound wherein $R^{11}$ is $—CH_2—NH—OR^3$ can be prepared by reducing the compound obtained above wherein $R^{11}$ is $—CH=N—OR^3$. The reduction can be carried out, for example, using a reducing reagent such as diisobutylaluminium hydride in an inert solvent such as dichloromethane, chloroform and tetrahydrofuran.

Preparation 7

Among the compounds (I), the compound wherein $—X----Y—$ is $—CH=CH—$, $R^{11}$ is a tetrahydropyranyloxymethyl group, and $R^2$ is a tri(lower alkyl)silyloxy group (the compound (XIIa)) can be obtained by using the compound (Va) obtained in Preparation 2 by the following method.

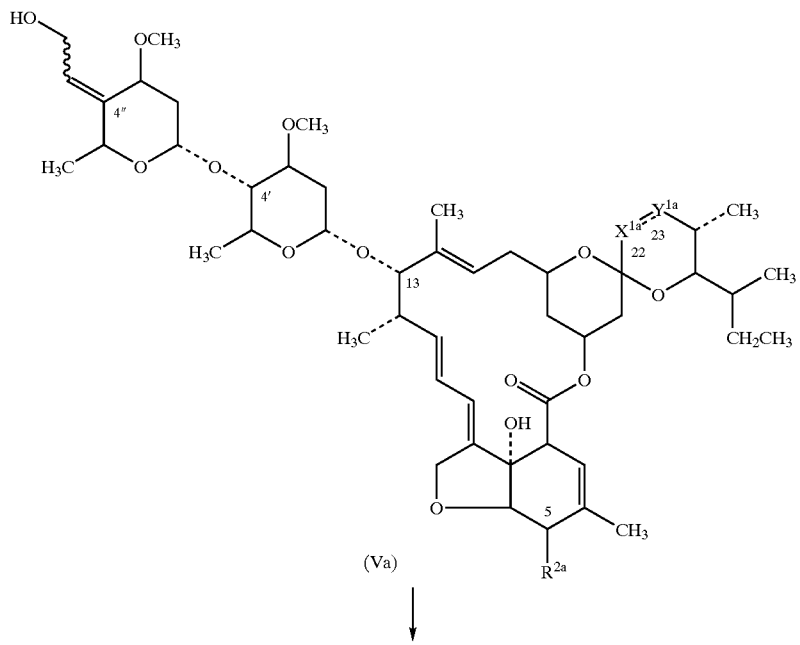

(Va)

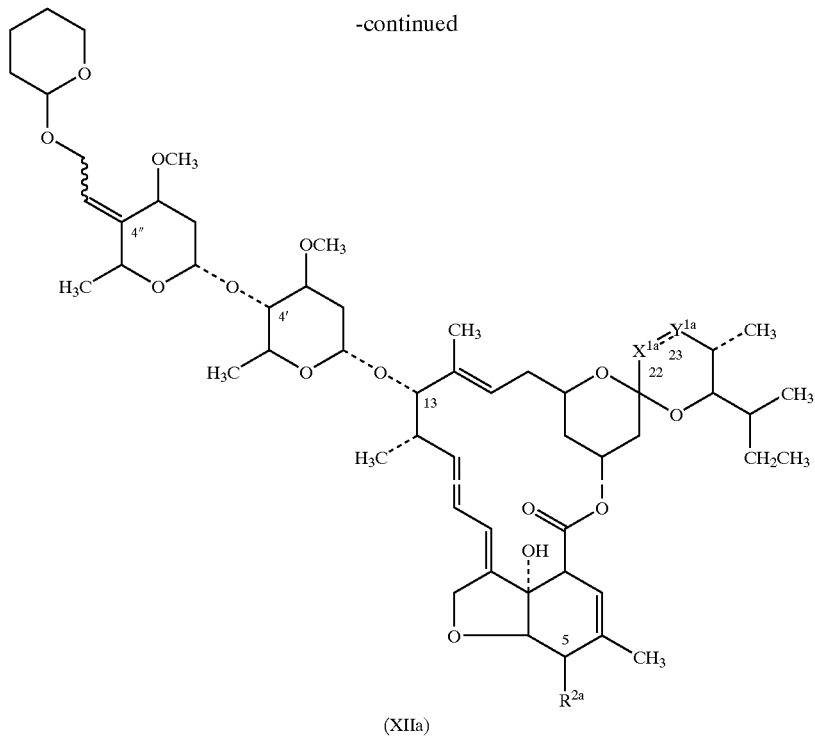

(XIIa)

(In the scheme, $R^{2a}$ and —$X^{1a}$----$Y^{1a}$— have the same meanings as those defined above.)

The compound (XIIa) can be obtained by reacting the compound (Va) obtained in Preparation 2 with an equivalent to an excess amount of dihydropyran in the presence of an acid catalyst in an inert solvent. Examples of the acid catalyst include hydrochloric acid, p-toluenesulfonic acid, and pyridinium p-toluenesulfonate. Examples of the inert solvent include chloroform and methylene chloride.

Preparation 8

Among the compounds (I), the compound wherein —X----Y— is —CH=CH—, $R^{11}$ is an aminomethyl group or a methylaminomethyl group, and $R^2$ is a tri(lower alkyl) silyloxy group (the compound (XIIIa)) can be prepared by using the compound (VIa) obtained in Preparation 3 as a starting material by the following method.

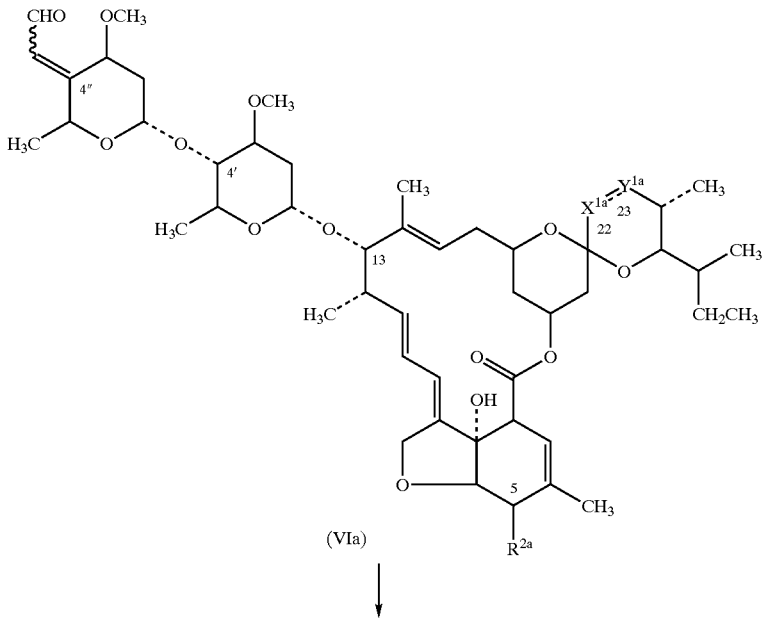

(VIa)

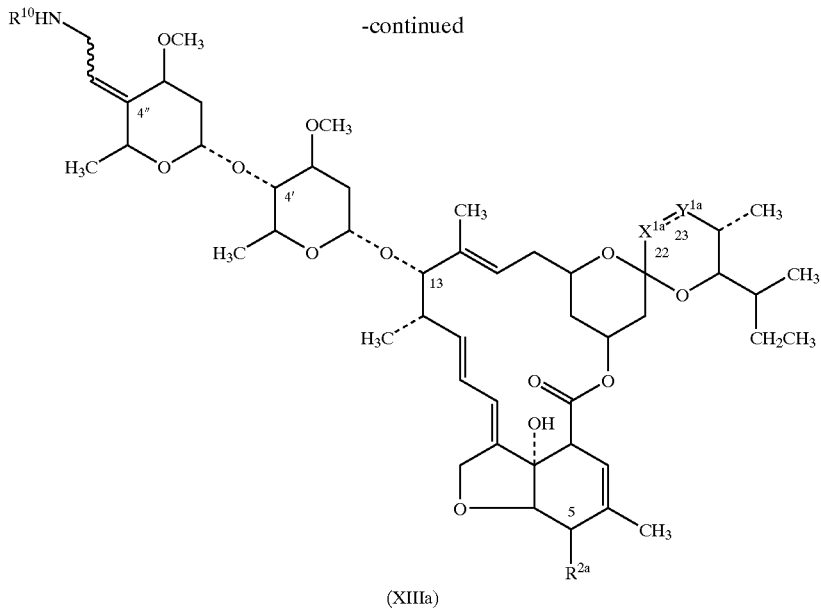

(XIIIa)

(In the scheme, $R^{10}$ represents a hydrogen atom or a methyl group, and $R^{2a}$ and —$X^{1a}$----$Y^{1a}$— have the same meanings as those defined above.)

The compound (XIIIa) wherein $R^{10}$ is a hydrogen atom can be obtained by reacting the compound (VIa) with an equivalent to an excess amount of hexamethyldisilazane in the presence of a catalytic amount to an excess amount of a metal salt in an inert solvent at a temperature ranging from −78° C. to a boiling point of a solvent used for 1 minute to 24 hours, and then adding an equivalent to an excess amount of a reducing agent.

Examples of the inert solvent include methyl acetate, ethyl acetate, propyl acetate, isopropyl acetate, methanol and ethanol. Examples of the metal salt include zinc chloride, and examples of the reducing agent include sodium borohydride, formic acid, hydrogen gas, and lithium aluminium hydride.

In Preparation 8 explained above, the compound (XIIIa) wherein $R^{10}$ is a methyl group can be obtained by using heptamethyldisilazane instead of hexamethyldisilazane.

Preparation 9

Among the compounds (I), the compound wherein —X----Y— is —CH=CH—, $R^{11}$ is CONR$^5$R$^6$ wherein $R^5$ and $R^6$ have the same meanings as those defined above, and $R^2$ is a tri(lower alkyl)silyloxy group (the compound (XIVa)) can be prepared by using the compound (VIIa) obtained in Preparation 4 as a starting material by the method set out below.

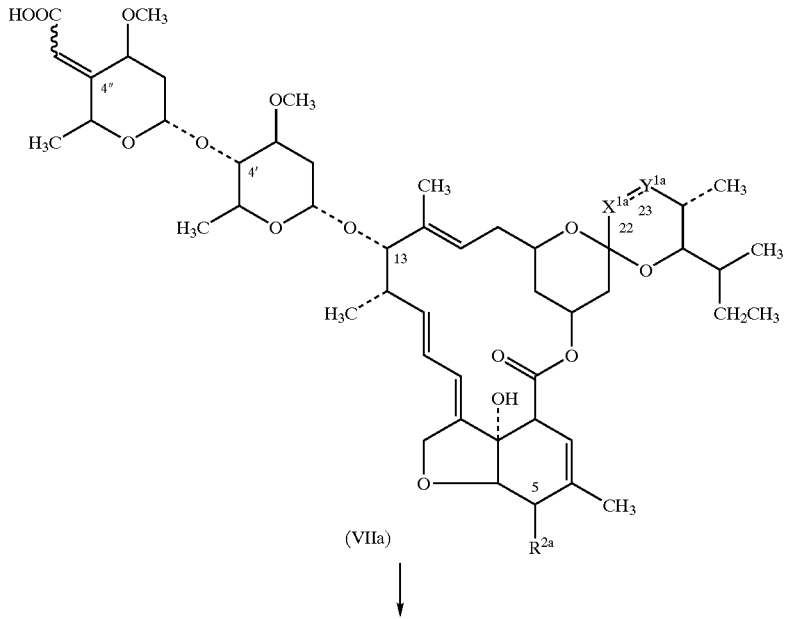

(VIIa)

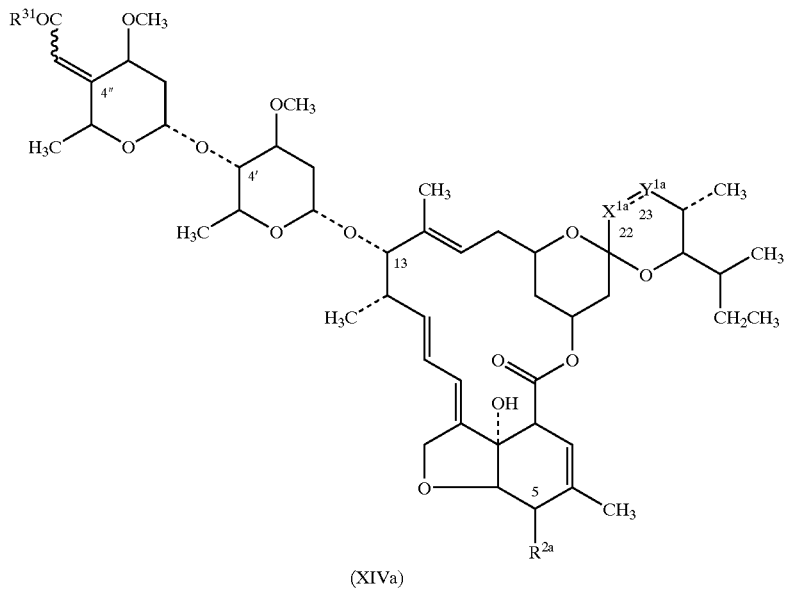

(XIVa)

(In the scheme, $R^{31}$ represents $NR^5R^6$ wherein $R^5$ and $R^6$ have the same meanings as those defined above, respectively, and $R^{2a}$ and —$X^{1a}$----$Y^{1a}$— have the same meanings as those defined above.)

The compound (XIVa) can be obtained by reacting the compound (VIIa) with an equivalent to an excess amount of the compound (XV) represented by the formula: $R^{31}H$ wherein $R^{31}$ has the same meaning as that defined above, for 1 minute to 24 hours in the presence of a base and a condensing agent in an inert solvent at a temperature ranging from −78° C. to a boiling point of a solvent used.

Examples of the inert solvent include chloroform, methylene chloride, methyl acetate, ethyl acetate, propyl acetate, isopropyl acetate, methanol, and ethanol. Examples of the condensing agent include 1-ethyl-3-(3-dimethylaminopropyl)carbodiimide (WSCI) hydrochloride, and 1,3-dicyclohexylcarbodiimide. Examples of the base include triethylamine, diisopropylethylamine, dimethylaminopyridine, and pyridine.

The compound (XIVa) can also be obtained by treating the compound (VIIa) with a chlorinating agent in an inert solvent or in the absence of a solvent at a temperature ranging from an ice-cooling temperature to a boiling point of a solvent used (at a boiling temperature of the chlorinating agent when no solvent is used) to convert the compound into a corresponding acid chloride, and reacting the resulting acid chloride with the compound (XV) represented by the formula: $R^{31}H$ wherein $R^{31}$ has the same meaning as that defined above in an inert solvent in the presence of a base at a temperature ranging from an ice-cooling temperature to a boiling point of a solvent used. Examples of the chlorinating agent include phosphorus oxychloride, phosphorus pentachloride, phosphorus trichloride, thionyl chloride, and thionyl bromide. Examples of the inert solvent for the chlorination include chloroform, methylene chloride, 1,2-dichloroethane, toluene, and benzene. Examples of the inert solvent for the condensation reaction include chloroform, methylene chloride, methyl acetate, ethyl acetate, propyl acetate, isopropyl acetate, tetrahydrofuran, methanol, and ethanol. Examples of the base include triethylamine, diisopropylethylamine, dimethylaminopyridine, and pyridine.

Preparation 10

Among the compounds (I), the compound wherein —X----Y— is —CH=CH— or —CH$_2$—C(=O)—, and $R^2$ is a hydroxyl group (the compounds (XVIa) and (XVIb)) can be obtained by carrying out deprotection at the 5-position of the compounds obtained in Preparations 1 to 9 and other methods.

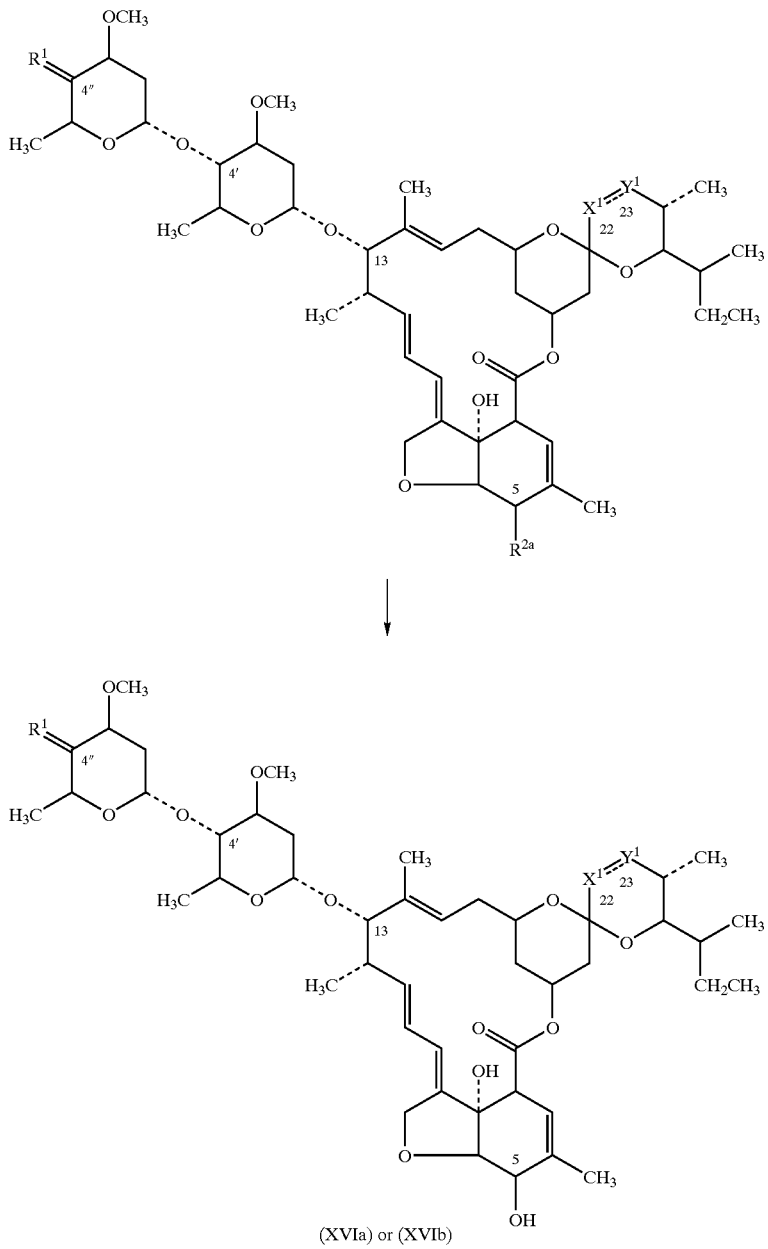

(In the scheme, $R^1$, $R^{2a}$ and —$X^1$----$Y^1$— have the same meanings as those defined above.)

The compound (XVIa) or (XVIb) can be obtained by treating the compound obtained in Preparations 1 to 9 for 1 minute to 24 hours with a catalytic amount to an amount serving as a solvent of a desilylating agent in an inert solvent at a temperature ranging from −78° C. to a boiling point of a solvent used.

As the inert solvent, tetrahydrofuran, ether, benzene, toluene, pyridine, isopropyl acetate, and the like may be used alone or as a mixture thereof. Examples of the desilylating agent include hydrogen fluoride, hydrochloric acid, hydrogen bromide, sulfuric acid, and hydrogen fluoride/pyridine complex.

The tri(lower alkyl)silyloxy group at the 5-position is sometimes converted into a hydroxyl group depending on reaction conditions for conversion of a functional group at the other position.

Preparation 11

Among the compounds (I), the compound wherein $R^2$ represents a carbonyl group together with the carbon atom at the 5-position (the compound (Ic)) can be obtained by oxidizing the compound (XVIaa) wherein —X----Y— is —CH=CH— among the compound (XVIa) obtained in Preparation 10.

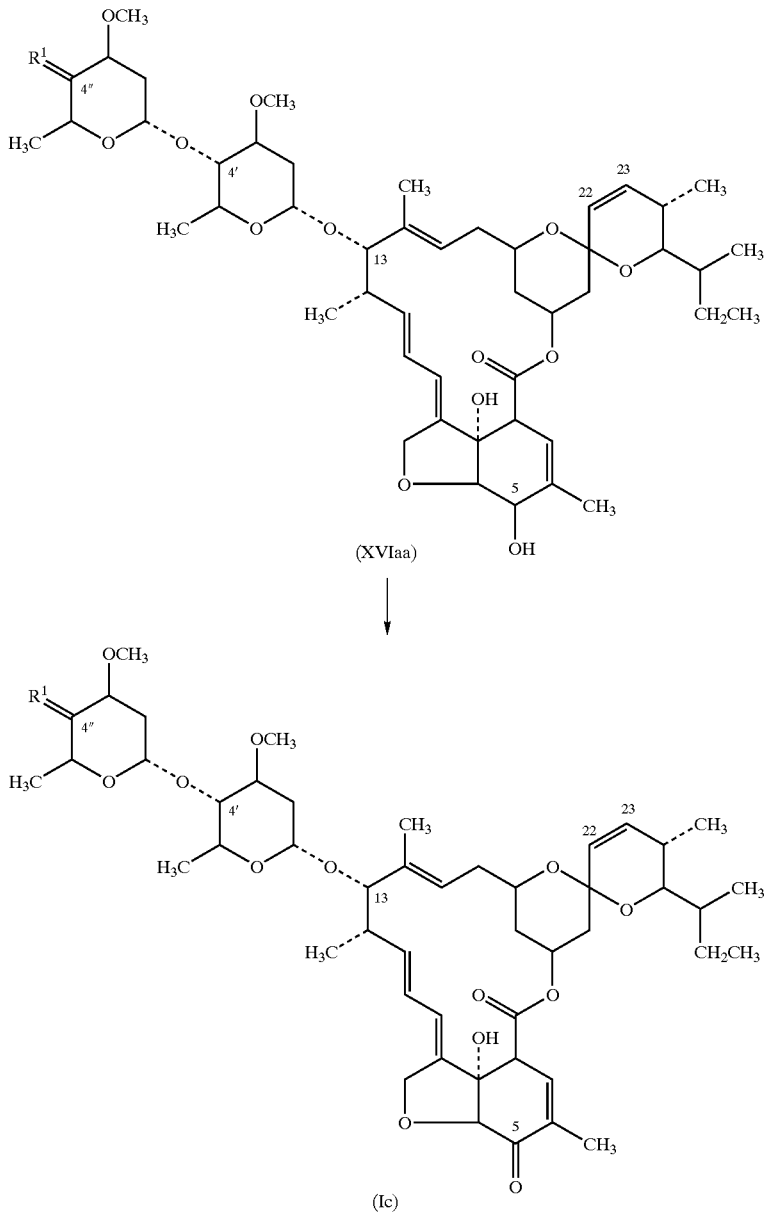

(In the scheme, $R^1$ has the same meaning as that defined above.)

The compound (Ic) can be prepared by treating the compound (XVIaa) with an equivalent to an excess amount of an oxidizing agent in an inert solvent at a temperature ranging from −78° C. to a boiling point of a solvent used. The reaction is generally finished in 1 minute to 2 days.

Examples of the inert solvent include chloroform, methylene chloride, and 1,2-dichloroethane. Examples of the oxidizing agent include manganese dioxide, pyridinium chlorochromate, chromium trioxide, and pyridinium dichromate.

The compound wherein $R^2$ forms a hydroxime group together with the carbon atom at the 5-position can be obtained by further reacting the resulting compound (Ic) with hydroxylamine or a salt thereof (examples of the salt include acid addition salts having the same meaning as that defined above).

The reaction of the compound (Ic) with hydroxylamine or a salt thereof can be carried out in the presence or absence of a base in an inert solvent at a temperature ranging from −78° C. to a boiling point of a solvent used. The hydroxylamine or a salt thereof and the base can be used in an equivalent to an excess amount. The reaction is generally finished in 1 minute to 2 days.

Examples of the inert solvent include lower alcohols such as methanol, ethanol and propanol, ethers such as ether and tetrahydrofuran, and halogenated hydrocarbons such as chloroform, methylene chloride and 1,2-dichloroethane.

Examples of the base include pyridine, 2,6-dimethylpyridine, dimethylaminopyridine, triethylamine, and diisopropylamine.

Preparation 12

The compound, wherein the double bond between the 22- and 23-positions are reduced (ivermectin derivatives, the compounds (B1)), can be prepared by the method set out below.

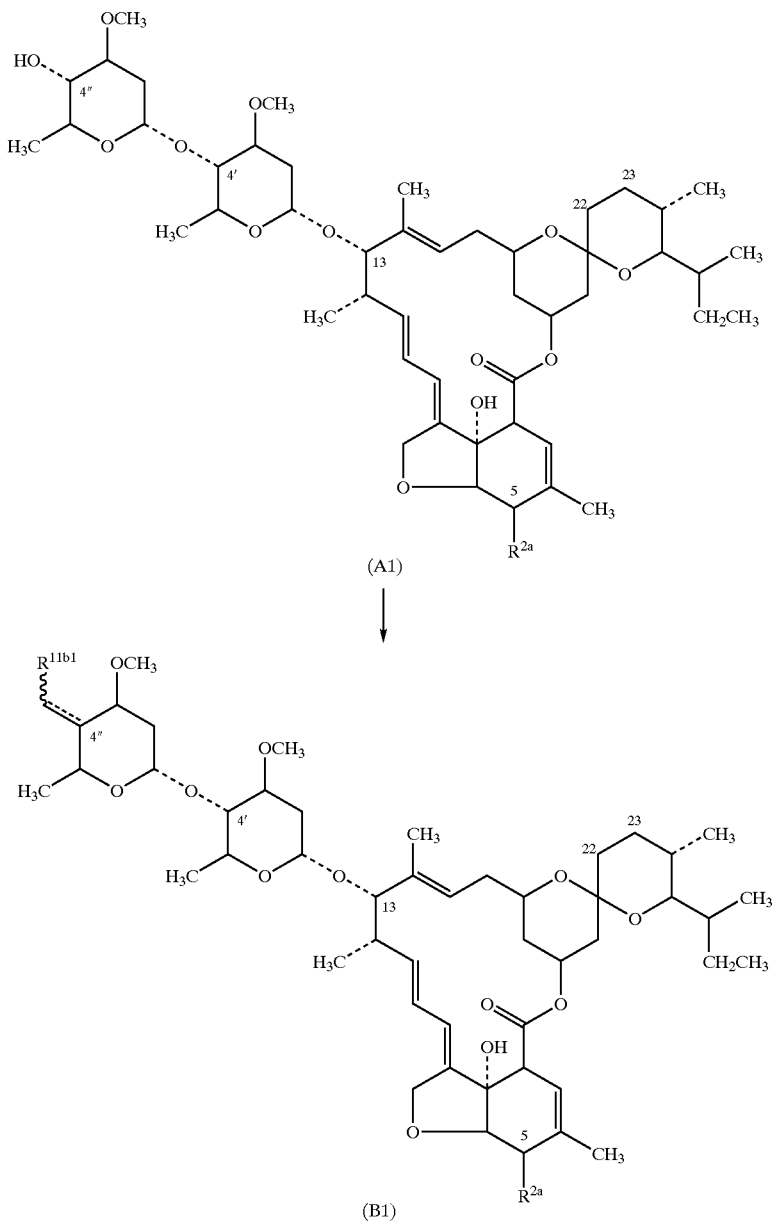

By using as a starting material an ivermectin derivative (A1), which is a known compound or can be prepared by a method similar to known methods, the corresponding carbonyl compound can be obtained through oxidation at the 4"-position according to a conventional method. The compound (B1) can be obtained by using the resulting compound for a reaction with the compound represented by the formula: $(RO)_2P(O)CH_2R^{11b1}$ wherein R has the same meaning as that defined above, and $R^{11b1}$ represents a cyano group or a lower alkenyloxycarbonyl group in a manner similar to that described in Preparation 1.

For the preparation of the compound wherein $R^{11b1}$ is a carboxyl group among the compounds (B1), the compound wherein $R^{11b1}$ is a cyano group or a lower alkenyloxycarbonyl group among the compounds (B1) is used as a starting material and subjected to a reaction in a manner similar to Preparation 4.

The compound wherein $R^1$ is a cyanomethyl group or a carboxymethyl group and —X----Y— is —$CH_2$—$CH_2$— can be prepared by catalytically reducing the compound obtained in Preparation 1 wherein $R^{11}$ is a cyano group or the compound obtained in Preparation 4 wherein $R^{11}$ is a carboxyl group for 1 minute to 100 hours in the presence of a catalyst such as triphenylphosphinerhodium chloride and a hydrogen source such as hydrogen and ammonium formate in a solvent such as benzene at a temperature ranging from 0° C. to a boiling point of a solvent used.

Deprotection of the hydroxyl group at the 5-position in the above compounds can be carried out according to the method described in Preparation 10.

Preparation 13

The compound wherein only the hydroxyl group at the 4"-position of the avermectin B2a derivative (the compound (C)) is oxidized into the corresponding carbonyl group (the compound (D)) or that wherein the hydroxyl groups at the 4"- and 23-positions of the compounds (C) are oxidized into the corresponding carbonyl groups, respectively (the compound (E)), can be prepared by treating the compound (C) with an appropriate oxidizing reagent.

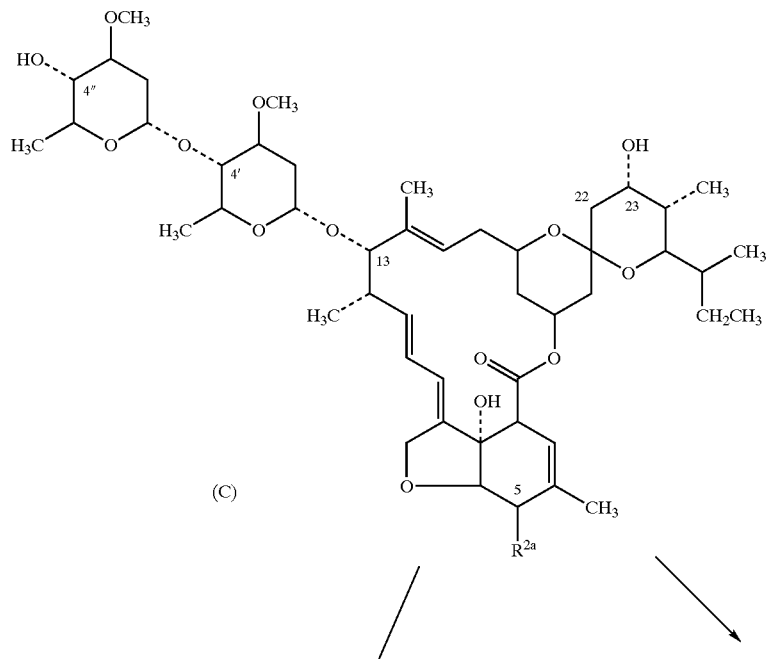
(C)
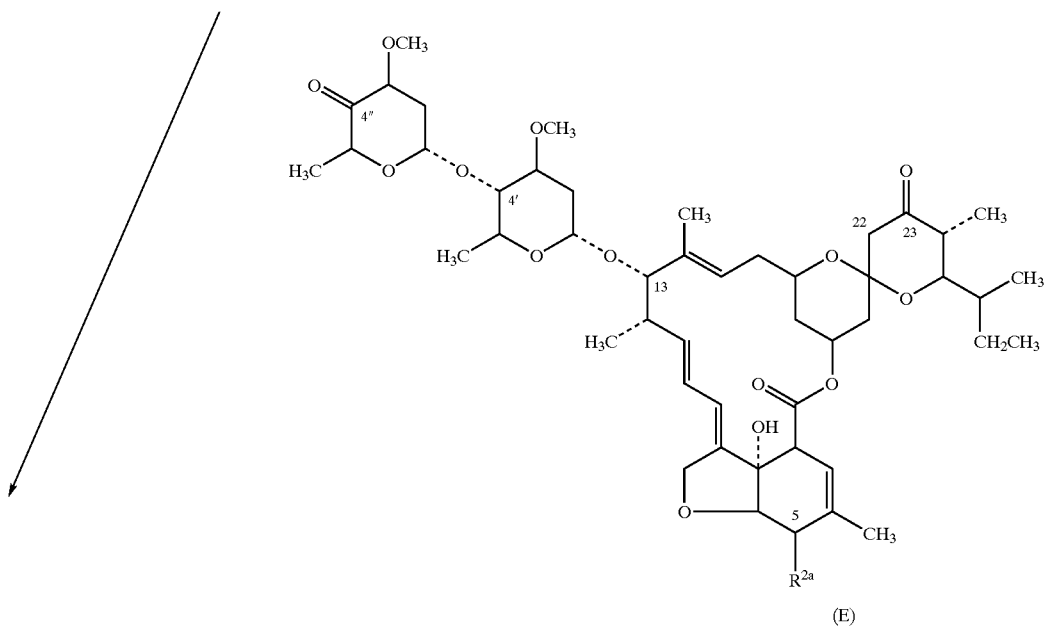
(E)

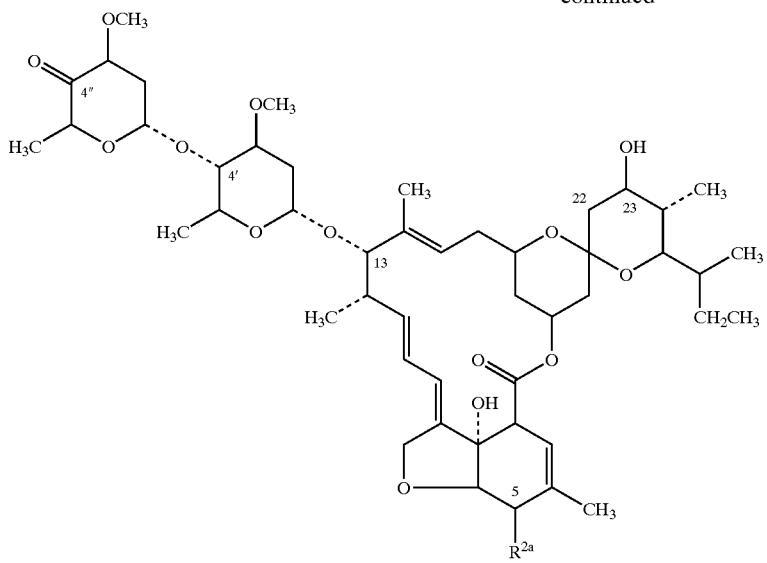

(D)

(In the scheme, $R^{2a}$ has the same meaning as that defined above.)

The compound wherein $R^{11}$ is a cyano group or a carboxyl group can be prepared by treating the compound (D) wherein only the hydroxyl group at the 4"-position is oxidized into the corresponding carbonyl group in a manner similar to that in Preparation 1 or 4.

Deprotection of the hydroxyl group at the 5-position in the above compounds can be carried out according to the method described in Preparation 10.

Preparation 14

Among the compounds (I), the compound (F), wherein —X----Y— is —$CH_2$—CH(OH)—, and $R^{11c}$ is a cyano group, a lower alkoxycarbonyl group or a lower alkenyloxycarbonyl group, can be prepared using the compound (D) obtained in Preparation 13 as a starting material in a manner similar to that in Preparation 1.

Preparation 15

Among the compounds (I), the compound (G), wherein —X----Y— is —$CH_2$—CH($R^{13a}$)— wherein $R^{13a}$ represents a lower alkylcarbonyloxy group which has the same meaning as that defined above, and $R^{11c}$ is a cyano group, a lower alkoxycarbonyl group or a lower alkenyloxycarbonyl group, can be prepared using the compound (F) obtained in Preparation 14 as a starting material in a manner similar to that in Preparation 5 (i.e., lower-alkanoylation of the hydroxyl group).

Preparation 16

Among the compounds (I), the compound (H) wherein —X----Y— is —$CH_2$—CH($R^{13}$)— wherein $R^{13}$ has the same meaning as that defined above, and $R^{11c}$ is a carboxyl group can be prepared by hydrolyzing the compound (F) or (G) wherein —X----Y— is —$CH_2$—CH($R^{13}$)— wherein $R^{13}$ has the same meaning as that defined above, and $R^{11c}$ is a cyano group, a lower alkoxycarbonyl group or a lower alkenyloxycarbonyl group in a conventional manner.

The aforementioned methods are typical examples of the preparations of the compounds (I), and the preparations of the compounds (I) are not limited to those explained above. It can be easily understood by a person skilled in the art that the compounds of the present invention can be prepared by other methods and the compounds (I) can also be obtained by carrying out the above methods in an appropriate combination or with an appropriate modification or alteration, if necessary.

In addition, the compounds (I) can also be obtained by an appropriate combination of the methods for converting a functional group which are usually used in the field of synthetic organic chemistry. For example, the compound wherein $R^2$ is a methoxy group can be prepared by a conventional methylation of the hydroxyl group of the corresponding compound wherein $R^2$ is a hydroxyl group. Similarly, the compound wherein $R^2$ is a lower alkoxyl group can be prepared by alkylation. For converting functional groups, desired conversions of functional groups can efficiently be made by protecting appropriate functional groups by methods for protection and deprotection conventionally used in the field of synthetic organic chemistry [e.g., see Protective Groups in Organic Synthesis, T. W. Greene, John Wiley & Sons Inc. (1981)], if necessary.

Specific examples of the aforementioned preparation and other preparations are described in Examples, and accordingly, a person skilled in the art can prepare any compounds falling within the compound (I) by referring to the above general explanations and specific explanations in Examples, and by appropriately choosing starting materials, reagents and reaction conditions and adding an appropriate alteration or modification, if necessary.

Purification of the desired compounds in the aforementioned preparations can be made by an appropriate combination of methods ordinarily used in the filed of synthetic organic chemistry, for example, filtration, extraction, washing, drying, concentration, crystallization, and various chromatography and the like. Synthetic intermediates may be subjected to a next reaction without purification.

Isomers such as regio isomers, geometrical isomers, tautomers and optical isomers may exist as the compounds (I). Any possible isomers and mixtures thereof in any proportion fall within the scope of the present invention. When a bond of a functional group that substitutes on a carbon atom forming a double bond is represented by a waved line in the specification, it means that the compound is an E- or Z-compound, or a mixture thereof.

For the preparation of a salt of the compound (I), a resulting salt, per se, may be purified when the compound (I) is obtained in the form of a salt. When a product is obtained in a free form, a salt may be isolated and purified after dissolving or suspending the product in a suitable solvent, and adding an acid or a base thereto to form a salt. The compounds (I) and salts thereof may exist in the forms of adducts with water or various solvents (i.e., hydrates or solvates), and these adducts also fall into the scope of the present invention. Moreover, any forms of crystal also fall into the scope of the present invention.

Specific examples of the compounds (I) obtained according to the present invention are shown in Tables 1 to 8. However, the compounds of the present invention are not limited to these examples. In the tables, OTBDMS represents tert-butyldimethylsilyloxy ($OSi(CH_3)_2C(CH_3)_3$), and (a) and (b) represent two isomers based on the hydroxyl group of the oxime moiety (Compounds 9 and 10, and Compounds 12 and 13) or two isomers based on the exomethylene at the 4"-position (Compounds 18 and 19). The isomers appended by (a) represent those having a larger Rf value (lower polarity) and the isomers appended by (b) represent those having a smaller Rf value (higher polarity) in thin-layer chromatography. As a developing solvent, one of the following solvents was used.

Toluene/acetone=4/1
Toluene/ethyl acetate=6/1

TABLE 1

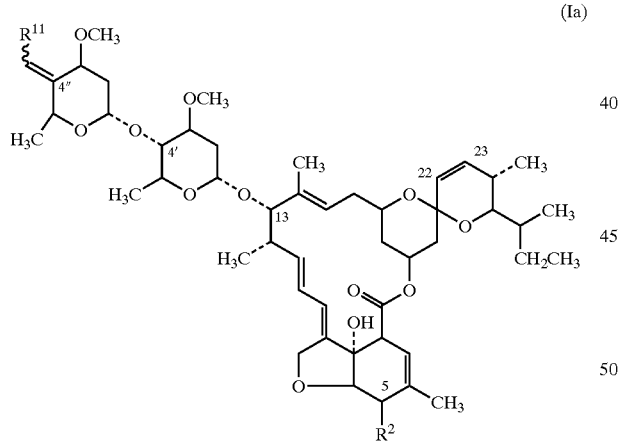

(Ia)

| Compound No. | $R^{11}$ | $R^2$ |
|---|---|---|
| 1 | $CO_2CH_2CH_3$ | OTBDMS |
| 2 | $CO_2CH_2CH_3$ | OH |
| 3 | $CH_2OH$ | OTBDMS |
| 4 | $CH_2OH$ | OH |
| 5 | CHO | OTBDMS |
| 6 | $CO_2CH_3$ | OTBDMS |
| 7 | $CO_2CH_3$ | OH |
| 8 | CHO | OH |
| 9 | $CH=N-OH$(a) | OH |
| 10 | $CH=N-OH$(b) | OH |
| 11 | $CH_2NHCH_3$ | OH |
| 12 | $CH=N-OCH_3$(a) | OH |
| 13 | $CH=N-OCH_3$(b) | OH |
| 14 | $CH_2NH_2$ | OTBDMS |

TABLE 1-continued

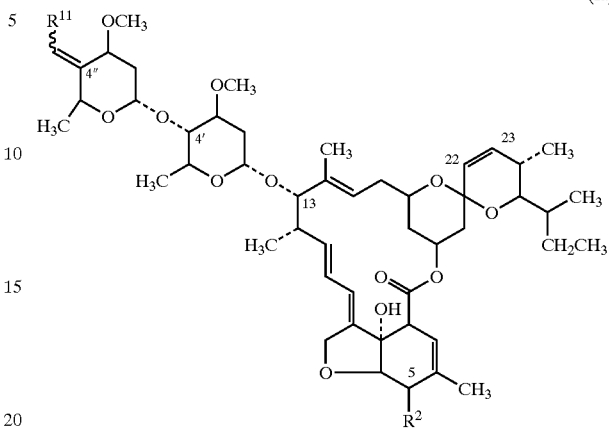

(Ia)

| Compound No. | $R^{11}$ | $R^2$ |
|---|---|---|
| 15 | CN(a) | OTBDMS |
| 16 | $CH_2O-C(O)-$(3-pyridyl) | OTBDMS |
| 17 | $CH_2O-C(O)-$(4-pyridyl) | OTBDMS |
| 18 | $CO_2CH_2CH=CH_2$(a) | OTBDMS |
| 19 | $CO_2CH_2CH=CH_2$(b) | OTBDMS |
| 20 | $CO_2CH_2CH=CH_2$ | OH |
| 21 | $CH_2O-C(O)-$(3-pyridyl) | OH |
| 22 | $CH=N-NHCONH_2$ | OH |
| 23 | CN | OH |
| 24 | COOH | OTBDMS |
| 25 | COOH | OH |
| 26 | $CH_2O-C(O)-$(4-pyridyl) | OH |
| 27 | $CH_2O-C(O)-$(2-pyrrolyl) | OH |

TABLE 1-continued
(Ia)
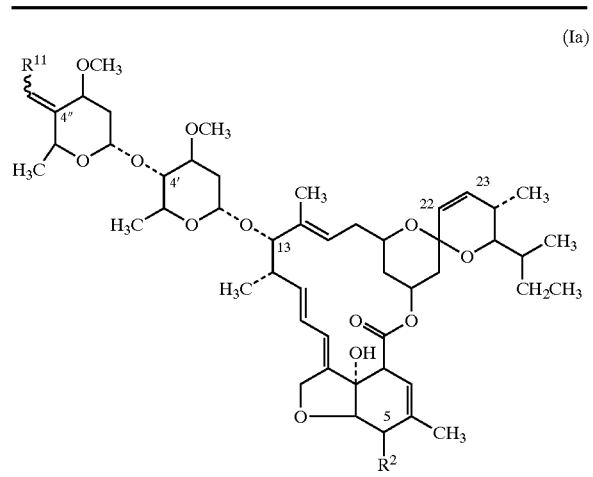
| Compound No. | R11 | R2 |
|---|---|---|
| 28 | CH2-[pyrrolidine-N-C(=O)-OC(CH3)3, with CO2 ester] | OTBDMS |
| 29 | CN(b) | OTBDMS |
| 30 | CH2-[pyrrolidine-N-C(=O)-OC(CH3)3, with CO2 ester] | OH |
| 31 | CH2O-[tetrahydropyran-2-yl] | OH |
| 32 | CH2OCOCH3 | OTBDMS |
| 33 | CH2O-C(=O)-[6-chloropyridin-3-yl] | OTBDMS |
| 34 | CH2O-C(=O)-[6-chloropyridin-3-yl] | OH |
TABLE 1-continued
(Ia)
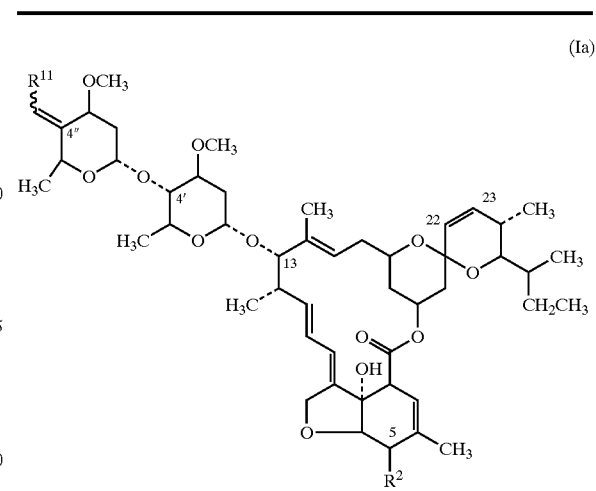
| Compound No. | R11 | R2 |
|---|---|---|
| 35 | CON-morpholine | OTBDMS |
| 36 | CON-morpholine | OH |
| 37 | CO2CH2-[furan-2-yl] | OH |
TABLE 2
(Ic)
| Compound No. | R11 |
|---|---|
| 38 | CHO |
| 39 | CH2OH |

TABLE 3
(Ib)
| Compound No. | R¹¹ᵃ | R² |
|---|---|---|
| 40 | CO₂CH₃ | OTBDMS |
| 41 | CO₂CH₃ | OH |
TABLE 4
(Id)
| Compound No. | R² | R²³ |
|---|---|---|
| 42 | OTBDMS | OH |
| 43 | OTBDMS | =O |
TABLE 5
(Id)
| Compound No. | R¹¹ᶜ | R² | R²³ |
|---|---|---|---|
| 44 | CO₂CH₃ | OTBDMS | =O |
| 45 | CO₂CH₃ | OH | =O |
| 46 | CO₂CH₂CH=CH₂ | OTBDMS | =O |
| 47 | COOH | OH | OH |
| 48 | CN | OH | OH |
| 49 | CN | OH | OCOCH₃ |
| 50 | CO₂CH₂CH=CH₂ | OTBDMS | OH |
| 51 | COOH | OTBDMS | OH |
| 52 | COOH | OH | OCOCH₃ |
| 78 | CO₂CH₃ | OH | OH |
TABLE 6
(Ia)
| Compound No. | R¹¹ | R² |
|---|---|---|
| 53 | CH₂OCO-(4-pyridyl) | =O |
| 54 | CN | =O |
| 55 | CH₂OCO-(4-pyridyl) | =N~OH |

TABLE 6-continued (Ia structure with R¹¹ at 4″ position and R² at 5 position)

| Compound No. | R¹¹ | R² |
|---|---|---|
| 56 | CN | =N∼OH |
| 57 | COOH | =O |
| 58 | COOH | =N∼OH |
| 61 | COOᵗBu | OTBDMS |
| 63 | COOᵗBu | OH |
| 65 | CH=CHCO₂CH₂CH=CH₂ | OTBDMS |
| 66 | CH=CHCOOH | OH |
| 67 | C(=O)-S-CH₂CH₂-NHCOCH₃ | OTBDMS |
| 68 | C(=O)-S-CH₂CH₂-NHCOCH₃ | OH |
| 69 | CH₂NHOCH₃ | OH |
| 70 | CH₂Cl | OTBDMS |
| 71 | CH₂Cl | OH |
| 72 | CH₂NH₂ | OTBDMS |
| 73 | CH₂NH₂ | OH |
| 74 | CH₂-piperazinyl (NH) | OH |
| 75 | CH₂-morpholinyl | OH |
| 76 | CH₂-piperidinyl | OH |
| 77 | CH₂NHCOCH₃ | OH |

TABLE 7

(Ia)

| Compound No. | =R²¹ | R² |
|---|---|---|
| 59 | =C(CN)(CH₃) | OTBDMS |
| 60 | =C(CN)(CH₃) | OTBDMS |
| 62 | =C(CN)(CH₃) | OH |
| 64 | =C(CN)(CH₃) | OH |

TABLE 8

Ivermectin derivatives

| Compound No. | R¹ | R² |
|---|---|---|
| 79 | OH | OTBDMS |
| 80 | =O | OTBDMS |
| 81 | =CHCO₂CH₂CH=CH₂ | OTBDMS |
| 82 | =CHCO₂CH₂CH=CH₂ | OTBDMS |
| 83 | =CHCN | OTBDMS |

TABLE 8-continued

Ivermectin derivatives

| Compound No. | R$^1$ | R$^2$ |
|---|---|---|
| 84 | =CHCN | OTBDMS |
| 85 | =CHCOOH | OH |
| 86 | =CHCN | OH |
| 87 | CH$_2$COOH | OH |
| 88 | CH$_2$CN | OH |

As the active ingredient of the medicament of the present invention, one or more substances selected from the group consisting of the compounds in the free form and physiologically acceptable salts thereof, and hydrates thereof and solvates thereof can be used. Any mixture of isomers or an isomer in a pure form may be used. The medicament of the present invention is generally provided in the form of a pharmaceutical composition which comprises one or more pharmaceutical additives and the aforementioned substance as an active ingredient. The route of administration is not particularly limited, and the medicament can be orally administered using preparations such as tablets, granules, capsules, syrups and powders, or parenterally administered by means of injection, intrarectal administration, transdermal administration or the like. Pharmaceutical formulations suitable for oral or parenteral administration are well-known to persons skilled in the art, and they can appropriately choose pharmaceutical additives suitable for the manufacture of the pharmaceutical formulations.

The medicament of the present invention may be applied to various parasitic diseases, and the kinds of the parasitic disease are not particularly limited. The medicament of the present invention may be applied to a human or a mammal other than a human. When the medicament is applied to a mammal other than a human, the medicament may be administered as a pharmaceutical composition, or alternatively, a pharmaceutical composition or the aforementioned active ingredient per se may be added to a feed. The compound of the present invention may be applied as pesticides such as an agent for controlling injurious insects such as blowflies, cockroaches, fleas and the like.

EXAMPLES

The present invention will be explained more specifically with reference to examples. However, the present invention is not limited to these examples.

Analytical data of the compounds described in the examples were measured by using the following apparatus. The number and structure of the compounds are the same as those described in Table 1 to 8 set out above.

IR: Horiba FT-210
NMR: JEOL (Nippon Denshi) JMN-EX270
MS: JEOL (Nippon Denshi) JMS-AX505

Solution A used in the following examples is a solution which is obtained by mixing 10 ml of hydrogen fluoride/pyridine complex, 6 ml of pyridine and 12 ml of tetrahydrofuran and stored in a polypropylene container below −10° C.

Among starting materials used in the following examples, 5-tert-butyldimethylsilyloxyavermectin B2a (5-O-tert-butyldimethylsilylavermectin B2a) is described in Tetrahedron Letters, Vol. 31, pp. 3525–3528 (1990) and J. Med. Chem., Vol. 25, pp. 658–663 (1982), and 5-tert-butyldimethylsilyloxy-7-trimethylsilyloxyavermectin B1a is described in U.S. Pat. No. 4,895,837.

Reference Example 1

Preparation of 5-O-tert-butyldimethylsilyl-4",23-dioxoavermectin B2a (compound [a])

In 3.5 ml of isopropyl acetate, 1.12 g of 5-O-tert-butyldimethylsilylavermectin B2a was dissolved, and 0.65 ml of dimethylsulfoxide (DMSO) and 1.5 ml of triethylamine were added to the solution under nitrogen gas atmosphere at −30° C. A solution of 0.6 ml of phenyl dichlorophosphate in 1.5 ml of isopropyl acetate was added slowly and dropwise thereto, and the mixture was stirred under nitrogen gas atmosphere below −20° C. for 1 hour and 30 minutes.

Then, a 1% aqueous phosphoric acid solution was added thereto and the mixture was extracted with ethyl acetate. The organic layer was washed with a saturated aqueous sodium hydrogencarbonate solution and dried over anhydrous sodium sulfate, and then the solvent was evaporated under reduced pressure to give a crude product. The resulting crude product was purified by column chromatography on silica gel using eluting solvents of hexane/ethyl acetate=4/1 to 2/1 to give 610 mg of the compound [a] in a 55% yield.

HR-FAB-MS: Calculated; C$_{54}$H$_{84}$O$_{15}$Si [M+Na]$^+$ 1023.5477, Found; 1023.5507 IR(KBr) $\lambda_{max}$cm$^{-1}$: 3469, 2962, 2933, 1739, 1724, 1452, 1124, 1054, 1006, 989 $^1$H NMR (270 MHz, CDCl$_3$, partial data) δ (ppm): 5.76 (1H, m), 5.70 (2H, m), 5.48 (1H, s), 5.30 (1H, s), 5.26 (1H, m), 4.90 (1H, t, J=7.3 Hz), 4.73 (1H, d, J=3.3 Hz), 4.64 (1H, d, J=15.8 Hz), 4.53 (1H, d, J=16.1 Hz), 4.38 (2H, m), 4.15 (1H, m), 3.98 (1H, s), 3.89 (1H, br.s), 3.77 (1H, d, J=5.6 Hz), 3.46 (3H, s), 3.39 (3H, s), 3.28 (1H, t, J=8.9 Hz), 1.76 (3H, s), 1.11 (3H, d, J=6.9 Hz), 0.09 (6H, s) $^{13}$C-NMR (67.8 MHz, CDCl$_3$) δ (ppm): 206.9, 205.8, 173.7, 140.1, 137.5, 137.3, 135.4, 124.8, 119.2, 117.6, 117.1, 100.5, 97.9, 94.7, 81.7, 81.0, 80.2, 80.0, 79.0, 77.9, 76.4, 70.6, 69.3, 68.1, 67.7, 67.6, 66.8, 60.3, 58.2, 56.3, 51.3, 46.3, 45.6, 40.3, 39.4, 39.3, 35.9, 35.8, 34.4, 33.7, 27.2, 25.7, 25.7, 25.7, 20.2, 19.9, 18.3, 15.0, 13.8, 12.3, 11.5, 8.6, −4.7, −5.0

Example 1

Preparation of Compound 1

To 0.5 ml of a 1.0 mol/L tetrahydrofuran solution of lithium hexamethyldisilazane, 0.1 ml of ethyl diethylphosphonoacetate was added, and the resulting mixture was stirred under ice-cooling (0° C.) for 30 minutes. Then, a solution of 235 mg of 5-O-tert-butyldimethylsilyl-4"-oxoavarmectin B1a represented by the following formula dissolved in 0.8 ml of tetrahydrofuran was added to the mixture, and the mixture was stirred at room temperature for 4 hours. To the reaction solution was added a saturated aqueous ammonium chloride solution and the mixture was extracted with ethyl acetate. The ethyl acetate layer was dried over anhydrous sodium sulfate, and the solvent was evaporated under reduced pressure to give a crude product. The resulting crude product was purified by column chromatography on silica gel using stepwise elution with eluting solvents of hexane/ethyl acetate=8/1~4/1~2/1~1/1 to give 72 mg of Compound 1 in a 29% yield.

4.98 (1H, m), 4.75 (1H, d, J=2.9 Hz), 4.46 (2H, m), 4.17 (2H, q, J=7.2 Hz), 4.01 (1H, s), 3.44 (3H, s), 3.35 (3H, s), 1.85 (3H, s) $^{13}$C-NMR (67.8 MHz, CDCl$_3$) δ (ppm): 173.7, 165.8, 156.4, 139.5, 138.1, 137.9, 136.3, 135.1, 127.7, 124.6, 120.4, 118.2, 118.0, 117.1, 96.2, 95.7, 95.0, 81.9, 80.3, 80.2, 79.0, 78.9, 74.8, 70.1, 68.4, 68.3, 68.3, 68.1, 67.7, 67.4, 60.3, 57.1, 56.4, 45.6, 40.4, 39.7, 36.6, 35.1, 34.7, 34.2, 33.4, 30.5, 27.5, 20.1, 19.9, 19.3, 17.9, 16.3, 15.0, 14.2, 12.9, 12.0

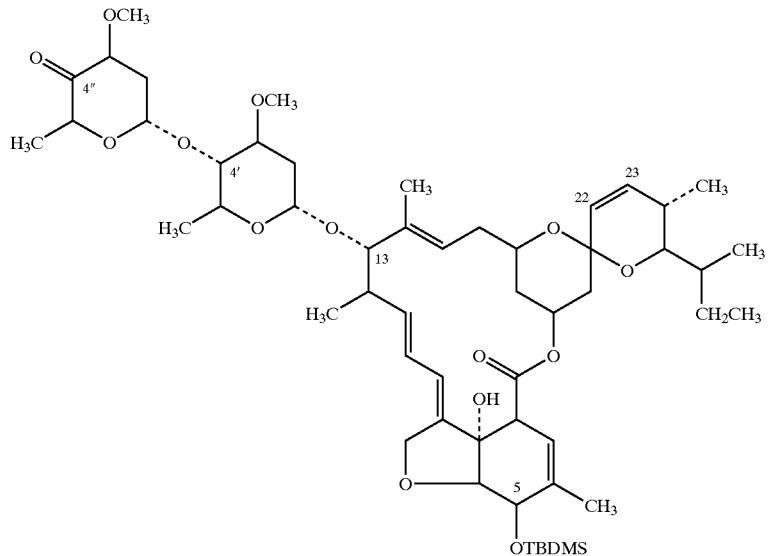

HR-FAB-MS: Calculated; C$_{58}$H$_{90}$O$_{15}$Si[M+Na]$^+$ 1077.5946, Found; 1077.5947 $^1$H NMR(270 MHz, CDCl$_3$, partial data) δ (ppm): 5.82 (1H, s), 5.73 (3H, m), 5.53 (1H, dd, J=2.3,9.9 Hz), 5.43 (1H, m), 5.33 (1H, m), 5.31 (1H, d, J=7.7 Hz), 5.13 (1H, s), 4.98 (1H,m), 4.75 (1H, d, J=2.9 Hz), 4.67 (1H, d, J=14.8 Hz), 4.56 (1H, d, J=14.8 Hz), 4.48 (1H, m), 4.40 (1H, m), 4.17 (2H, q, J=7.2 Hz), 3.91 (1H, s), 3.44 (3H, s), 3.36 (3H, s), 1.77 (3H, s), 0.91 (9H, s), 0.11 (6H, s)

Example 2

Preparation of Compound 2

In 1.5 ml of tetrahydrofuran, 50 mg of Compound 1 obtained in Example 1 was dissolved, 0.2 ml of the solution A was added thereto, and the mixture was stirred at room temperature for a night. Pyridine was added on an ice bath, and an aqueous sodium hydrogencarbonate solution was added for neutralization, and then the mixture was extracted with ethyl acetate. The ethyl acetate layer was dried over anhydrous magnesium sulfate, and the solvent was evaporated under reduced pressure to give a crude product. The resulting crude product was purified by column chromatography on silica gel using stepwise elution with eluting solvents of hexane/2-propanol=85/15~4/1~3/1 to give 27 mg of Compound 2 in a 62% yield.

HR-FAB-MS: Calculated; C$_{52}$H$_{76}$O$_{15}$[M+Na]$^+$ 963.5081, Found; 963.5082 IR(KBr) $\lambda_{max}$cm$^{-1}$: 3482, 2969, 2933, 1720, 1654, 1457, 1382, 1159, 1120, 991 $^1$H NMR (270 MHz, CDCl$_3$, partial data) δ (ppm): 5.82 (1H, s), 5.73 (3H, m), 5.53 (1H, dd, J=2.3, 9.9 Hz), 5.40 (3H, m), 5.13 (1H, s),

Example 3

Preparation of Compound 3

In 1.5 ml of methylene chloride, 164 mg of Compound 6 obtained in Example 6 was dissolved, 0.55 ml of a 1.0 mol/L tetrahydrofuran solution of diisobutylaluminium hydride was dropwise added thereto at −78° C. and then the mixture was stirred at the same temperature for 2 hours. Methanol was added thereto for inactivation of the excess reagent, and further celite and sodium sulfate decahydrate were added thereto. The mixture was stirred at room temperature for 30 minutes and filtered. The residue was washed with ethyl acetate. The organic layers were combined and concentrated under reduced pressure to give a crude product. The resulting crude product was purified by column chromatography on silica gel using stepwise elution with eluting solvents of methylene chloride/tetrahydrofuran=20/1~10/1~6/1 to give 132 mg of Compound 3 in a 83% yield.

HR-FAB-MS: Calculated; C$_{56}$H$_{88}$O$_{14}$Si[M+Na]$^+$ 1035.5840, Found; 1035.5841 IR(KBr) $\lambda_{max}$cm$^{-1}$: 3477, 2962, 2931, 1735, 1718, 1459, 1380, 1160, 1124, 989 $^1$H NMR (270 MHz, CDCl$_3$, partial data) δ (ppm): 5.70 (5H, m), 5.51 (1H, dd, J=2.3, 9.9 Hz), 5.36 (3H, m), 4.97 (1H, m), 4.73 (1H, d, J=3.3 Hz), 4.58 (2H, q, J=4.8 Hz), 4.39 (2H, m), 4.27 (3H, m), 3.93 (1H, s), 3.45 (3H, s), 3.38 (3H, s), 1.78 (3H, s), 1.31 (3H, d, J=6.3 Hz), 1.22 (3H, d, J=6.3 Hz), 1.12 (3H, d, J=7.0 Hz), 0.89 (9H, s), 0.10 (6H, s)

Example 4

Preparation of Compound 4

In 1 ml of tetrahydrofuran, 87 mg of Compound 3 obtained in Example 3 was dissolved, 1 ml of the solution A was added thereto, and the mixture was stirred at room temperature for a night. Then, the reaction mixture was treated and purified in the manners similar to those in Example 2 to give 49 mg of Compound 4 in a 64% yield.

HR-FAB-MS: Calculated; $C_{50}H_{74}O_{14}[M+Na]^+$ 921.4976, Found; 921.4922 IR(KBr) $\lambda_{max}cm^{-1}$: 3465, 2967, 2933, 1735, 1718, 1457, 1378, 1180, 1118, 989 $^1$H NMR (270 MHz, CDCl$_3$, partial data) δ (ppm): 5.88 (1H, m), 5.73 (4H, m), 5.54 (1H, dd, J=2.6, 9.9 Hz), 5.37 (3H, m), 4.98 (1H, m), 4.76 (1H, d, J=3.0 Hz), 4.67 (2H, s), 3.45 (3H, s), 3.36 (3H, s), 1.86 (3H, s), 1.33 (3H, d, J=6.6 Hz), 1.25 (3H, d, J=5.9 Hz), 1.14 (3H, d, J=6.9 Hz) $^{13}$C-NMR (67.8 MHz, CDCl$_3$) δ (ppm): 173.7, 141.6, 139.5, 138.1, 137.9, 136.3, 135.1, 127.7, 125.9, 124.7, 120.4, 118.3, 118.0, 96.7, 95.7, 95.0, 81.9, 80.4, 79.9, 79.0, 74.9, 73.2, 68.4, 68.3, 68.3, 67.7, 67.5, 67.1, 58.4, 56.9, 55.8, 45.7, 40.4, 39.8, 36.6, 35.1, 34.7, 34.2, 33.2, 30.6, 27.5, 20.2, 19.9, 18.2, 18.0, 16.4, 15.1, 12.9, 12.0 (one peak was not observed because of overlapping with another peak.)

Example 5

Preparation of Compound 5

In 3 ml of methylene chloride, 791 mg of Compound 3 obtained in Example 3 was dissolved, 0.8 g of manganese dioxide was added thereto, and the mixture was stirred for 1 day. The reaction mixture was diluted with diethyl ether and passed through a dry silica gel column, and the silica gel column was washed with diethyl ether. The resulting diethyl ether solution was concentrated under reduced pressure to give a crude product. The resulting crude product was purified by column chromatography on silica gel using stepwise elution with eluting solvents of hexane/ethyl acetate=4/1~2/1~1/1 to give 628 mg of Compound 5 in a 80% yield.

HR-FAB-MS: Calculated; $C_{56}H_{86}O_{14}Si[M+Na]^+$ 1033.5684, Found; 1033.5740 IR(KBr) $\lambda_{max}cm^{-1}$: 3444, 2962, 2933, 1727, 1660, 1461, 1384, 1160, 1124, 1008, 989 $^1$H NMR (270 MHz, CDCl$_3$, partial data) δ (ppm): 10.3 (1H, d, J=7.3 Hz), 5.90 (1H, d, J=7.3 Hz), 5.74 (4H, m), 5.54 (1H, dd, J=2.3, 9.9 Hz), 5.48 (1H, m), 5.33 (2H, m), 4.99 (1H, m), 4.78 (1H, s), 4.43 (1H, br.s), 4.13 (1H, s), 3.45 (3H, s), 3.44 (3H, s), 3.31 (1H, t, J=9.2 Hz), 2.03 (1H, m), 1.79 (3H, s), 1.35 (3H, d, J=6.3 Hz), 1.15 (3H, d, J=6.9 Hz), 0.13 (6H, s) $^{13}$C-NMR (67.8 MHz, CDCl$_3$) δ (ppm): 193.7, 174.1, 158.7, 140.2, 137.5, 137.4, 136.2, 135.1, 127.7, 125.1, 124.8, 119.2, 118.3, 117.1, 97.3, 95.7, 95.0, 82.0, 80.5, 80.2, 80.0, 79.1, 75.2, 74.8, 69.4, 68.4, 68.3, 67.9, 67.2, 67.0, 56.7, 56.4, 45.7, 40.4, 39.6, 36.5, 36.4, 35.1, 34.6, 34.2, 30.5, 27.5, 25.8, 25.8, 25.8, 20.3, 20.0, 18.4, 18.1, 17.6, 16.3, 15.1, 12.9, 12.0, −4.6, −4.9

Example 6

Preparation of Compound 6

To 0.55 ml of a 1.0 mol/L tetrahydrofuran solution of lithium hexamethyldisilazane, 0.11 ml of methyl diethylphosphonoacetate was added, and the resulting mixture was stirred under ice-cooling (0° C.) for 30 minutes. Then, 464 mg of 5-O-tert-butyldimethylsilyl-4"-oxoavermectin B1a dissolved in 1.4 ml of tetrahydrofuran was added to the mixture, and the mixture was stirred at room temperature for 4 hours. The reaction mixture was then treated and purified in the manners similar to those in Example 1 to give 402 mg of Compound 6 in a 82% yield.

HR-FAB-MS: Calculated; $C_{57}H_{88}O_{15}Si[M+Na]^+$ 1063.5790, Found; 1063.5840 IR(KBr) $\lambda_{max}cm^{-1}$: 3444, 2962, 2933, 1727, 1660, 1461, 1384, 1160, 1124, 1008, 989 $^1$H NMR (270 MHz, CDCl$_3$, partial data) δ (ppm): 5.84 (1H, s), 5.72 (3H, m), 5.54 (1H, dd, J=2.3, 9.9 Hz), 5.44 (1H, t, J=7.2 Hz), 5.35 (1H, m), 5.32 (1H, s), 5.13 (1H, s), 4.98 (1H, m), 4.76 (1H, s), 4.52 (2H, q, J=4.9 Hz), 4.45 (2H, m), 3.72 (3H, s), 3.45 (3H, s), 3.37 (3H, s), 1.78 (3H, s), 1.49 (3H, s), 1.41 (3H, d, J=6.6 Hz), 1.24 (3H, d, J=6.3 Hz), 1.13 (3H, d, J=6.9 Hz), 0.92 (9H, s), 0.13 (6H, s)

Example 7

Preparation of Compound 7

In 2 ml of tetrahydrofuran, 67 mg of Compound 6 obtained in Example 6 was dissolved, 0.3 ml of the solution A was added thereto, and the mixture was stirred at room temperature for a night. Then, the reaction mixture was treated and purified in the manners similar to those in Example 2 to give 41 mg of Compound 7 in a 67% yield.

HR-FAB-MS: Calculated; $C_{51}H_{74}O_{15}[M+Na]^+$ 949.4925, Found; 949.4955 IR(KBr) $\lambda_{max}cm^{-1}$: 3446, 2967, 2933, 1724, 1456, 1382, 1159, 1120, 987 $^1$H NMR (270 MHz, CDCl$_3$, partial data) δ (ppm): 5.77 (5H, m), 5.53 (1H, dd, J=2.6, 9.9 Hz), 5.40 (3H, m), 5.12 (1H, s), 4.98 (1H, m), 4.75 (1H, d, J=3.9 Hz), 4.66 (2H, s), 4.48 (1H, m), 4.28 (1H, br.s), 3.71 (3H, s), 3.45 (3H, s), 3.36 (3H, s), 1.85 (3H, s), 1.47 (3H, s), 1.40 (3H, d, J=7.6 Hz), 1.23 (3H, d, J=5.9 Hz), 1.12 (3H, d, J=6.9 Hz) $^{13}$C-NMR (67.8 MHz, CDCl$_3$) δ (ppm): 173.7, 166.2, 156.8, 139.5, 138.0, 137.9, 136.2, 135.1, 127.7, 124.6, 120.4, 118.2, 118.0, 116.6, 96.1, 95.7, 95.0, 81.9, 80.3, 80.2, 79.0, 78.9, 74.8, 70.2, 68.4, 68.3, 68.3, 68.1, 67.7, 67.4, 57.1, 56.5, 51.3, 45.6, 40.4, 39.7, 36.6, 35.1, 34.7, 34.2, 33.4, 30.5, 27.4, 20.1, 19.9, 19.3, 17.9, 16.3, 15.0, 13.0, 12.0

Example 8

Preparation of Compound 8

In 1 ml of tetrahydrofuran, 93 mg of Compound 5 obtained in Example 5 was dissolved, 1 ml of the solution A was added thereto, and the mixture was stirred at room temperature for a night. Then, the reaction mixture was treated and purified in the manners similar to those in Example 2 to give 62 mg of Compound 8 in a 75% yield.

HR-FAB-MS: Calculated; $C_{50}H_{72}O_{14}[M+Na]^+$ 919.4819, Found; 919.4821 IR(KBr) $\lambda_{max}cm^{-1}$: 3453, 2967, 2933, 1723, 1673, 1456, 1378, 1160, 1118, 991 $^1$H NMR (270 MHz, CDCl$_3$, partial data) δ (ppm): 10.36 (1H, d, J=7.6 Hz), 5.90 (1H, d, J=7.6 Hz), 5.86 (1H, m), 5.74 (3H, m), 5.53 (1H, dd, J=2.3, 9.9 Hz), 5.48 (1H, m), 5.41 (2H, m), 4.98 (1H, m), 4.78 (1H, br.s), 4.68 (1H, s), 4.53 (2H, m), 4.29 (1H, br.s), 3.45 (3H, s), 3.43 (3H, s), 2.02 (1H, m), 1.87 (3H, s), 1.36 (3H, d, J=6.6 Hz), 1.25 (3H, d, J=6.9 Hz), 1.16 (3H, d, J=6.3 Hz) $^{13}$C-NMR (67.8 MHz, CDCl$_3$) δ (ppm): 193.6, 173.7, 158.7, 139.6, 138.0, 138.0, 136.2, 135.1, 127.7, 125.1, 124.7, 120.4, 118.3, 118.0, 97.3, 95.7, 95.0, 82.0, 80.5, 80.4, 79.1, 75.2, 74.9, 68.4, 68.3, 68.3, 67.7, 67.3, 67.2, 67.1, 56.7, 56.4, 45.7, 40.4, 39.7, 36.6, 36.4, 35.1, 34.6, 34.2, 30.5, 27.5, 20.2, 19.9, 18.1, 17.7, 16.3, 15.1, 12.9, 12.0

Example 9

Preparation of Compounds 9 and 10

To a solution of 103 mg of Compound 5 obtained in Example 5 dissolved in 0.3 ml of ethanol, 21 mg of hydroxylamine hydrochloride and 0.5 ml of pyridine were added, and the resulting mixture was stirred at room temperature for 1 hour. To the reaction solution was added an aqueous sodium hydrogencarbonate solution and the mixture was extracted with ethyl acetate. The ethyl acetate layer was dried over anhydrous magnesium sulfate, and the solvent was evaporated under reduced pressure to give a crude product.

The resulting crude product was dissolved in 1 ml of tetrahydrofuran, 0.5 ml of the solution A was added thereto, and the mixture was stirred at room temperature for a night. To the reaction solution was added pyridine and an aqueous sodium hydrogencarbonate solution and the mixture was extracted with ethyl acetate. The ethyl acetate layer was dried over anhydrous magnesium sulfate, and the solvent was evaporated to give a crude product. The resulting crude product was purified by column chromatography on silica gel using stepwise elution with eluting solvents of toluene/acetone=10/1 to 5/1 to give 81 mg of a mixture of Compounds 9 and 10 in a 69% yield.

Compounds 9 and 10 are isomers based on the hydroxyl group of the oxime. The mixture was separated by thin-layer chromatography with a developing solvent of toluene/acetone=4/1 to give 45 mg of Compound 9 having the Rf value of 0.33, and 30 mg of Compound 10 having the Rf value of 0.23, respectively.

Compound 9:

HR-FAB-MS: Calculated; $C_{50}H_{73}NO_{14}[M+Na]^+$ 934.4928, Found; 934.4918 IR(KBr) $\lambda_{max}cm^{-1}$: 3417, 2967, 2933, 1714, 1456, 1378, 1160, 1118, 993 $^1$H NMR (270 MHz, CDCl$_3$, partial data) δ (ppm): 8.31 (1H, d, J=10.2 Hz), 6.08 (1H, d, J=10.2 Hz), 5.84 (1H, m), 5.74 (3H, m), 5.54 (1H, dd, J=2.3, 9.9 Hz), 5.41 (3H, m), 4.77 (1H, s), 4.67 (2H, s), 4.45 (1H, m), 4.29 (2H, m), 4.14 (1H, br.s), 3.46 (3H, s), 3.36 (3H, s), 1.86 (3H, s), 1.37 (3H, d, J=6.6 Hz), 1.25 (3H, d, J=6.3 Hz), 1.15 (3H, d, J=6.9 Hz)

Compound 10:

HR-FAB-MS: Calculated; $C_{50}H_{73}NO_{14}[M+Na]^+$ 934.4928, Found; 934.4929 IR(KBr) $\lambda_{max}cm^{-1}$: 3417, 2967, 2933, 1714, 1456, 1378, 1160, 1118, 993 $^1$H NMR (270 MHz, CDCl$_3$, partial data) δ (ppm): 7.72 (1H, d, J=9.6 Hz), 6.71 (1H, d, J=9.6 Hz), 5.85 (1H, m), 5.74 (3H, m), 5.55 (1H, dd, J=2.6, 9.9 Hz), 5.43 (4H, m), 4.77 (1H, d, J=3.0 Hz), 4.67 (2H, s), 4.48 (1H, m), 4.37 (1H, m), 4.28 (1H, d, J=7.2 Hz), 3.45 (3H, s), 3.37 (3H, s), 1.86 (3H, s), 1.40 (3H, d, J=6.6 Hz), 1.25 (3H, d, J=6.3 Hz), 1.15 (3H, d, J=6.9 Hz) $^{13}$C-NMR (67.8 MHz, CDCl$_3$) δ (ppm): 173.7, 148.0, 144.9, 139.5, 138.1, 137.9, 136.3, 135.8, 135.1, 127.7, 124.7, 120.4, 118.3, 118.1, 112.0, 97.0, 95.8, 95.1, 81.9, 80.4, 79.2, 79.2, 79.1, 74.9, 74.0, 68.4, 68.4, 67.9, 67.7, 67.4, 56.9, 56.3, 45.7, 40.5, 39.8, 36.6, 35.5, 35.2, 34.7, 34.2, 30.6, 27.5, 20.2, 19.9, 18.3, 18.1, 16.4, 15.1, 13.0, 12.0

Example 10

Preparation of Compound 11

To a solution of 30 mg of Compound 5 obtained in Example 5 dissolved in 0.4 ml of isopropyl acetate, 6 mg of zinc(II) chloride and 20 μl of heptamethyldisilazane were added, and the resulting mixture was heated to 45° C. and stirred. The reaction was continued at the same temperature for 4 hours. After the mixture was cooled to 0° C., 0.4 ml of ethanol and 5 mg of sodium borohydride was added thereto, and then the mixture was stirred at room temperature for 30 minutes. To the reaction solution was added a saturated brine and the mixture was extracted with ethyl acetate. The ethyl acetate layer was dried over anhydrous magnesium sulfate, and the solvent was evaporated under reduced pressure to give a crude product.

The resulting crude product was purified by thin-layer chromatography on silica gel of 0.5 mm thickness using a developing solvent of methylene chloride/methanol=9/1 to give 5-O-tert-butyldimethylsilyl-4"-N-methylaminoethylideneavermectin B1a.

The resulting 5-O-tert-butyldimethylsilyl-4"-N-methylaminoethylideneavermectin B1a was dissolved in 0.4 ml of tetrahydrofuran, 0.2 ml of the solution A was added thereto, and the mixture was stirred at room temperature for a night. The mixture was then treated in a manner similar to that in Example 2, and purified by column chromatography on silica gel using stepwise elution with eluting solvents of methylene chloride/methanol=6/1 to 2/1 and methanol to give 6 mg of Compound 11 in a 68% yield.

HR-FAB-MS: Calculated; $C_{51}H_{77}NO_{13}[M+Na]^+$ 912.5475, Found; 912.5460 IR(KBr) $\lambda_{max}cm^{-1}$: 3477, 2931, 1737, 1716, 1454, 1118, 989 $^1$H NMR (270 MHz, CDCl$_3$, partial data) δ (ppm): 5.79 (4H, m), 5.61 (1H, m), 5.55 (1H, dd, J=2.3, 9.9 Hz), 5.38 (3H, m), 4.99 (1H, m), 4.76 (1H, d, J=3.0 Hz), 4.68 (2H, s), 4.40 (1H, m), 4.27 (2H, m), 3.46 (3H, s), 3.35 (3H, s), 2.49 (3H, s), 1.87 (3H, s), 1.34 (3H, d, J=6.3 Hz), 1.15 (3H, d, J=6.9 Hz)

Example 11

Preparation of Compounds 12 and 13

In 0.3 ml of ethanol, 87 mg of Compound 5 obtained in Example 5 was dissolved, 22 mg of methyloxyamine hydrochloride and 0.5 ml of pyridine were added thereto, and the mixture was stirred at room temperature for 1 hour. To the reaction solution was added an aqueous sodium hydrogencarbonate solution and the mixture was extracted with ethyl acetate. The ethyl acetate layer was dried over anhydrous magnesium sulfate, and the solvent was evaporated under reduced pressure to give a crude product.

The resulting crude product was dissolved in 1 ml of tetrahydrofuran, 0.5 ml of the solution A was added thereto, and the mixture was stirred at room temperature for a night. To the reaction solution was added pyridine and an aqueous sodium hydrogencarbonate solution and the mixture was extracted with ethyl acetate. The ethyl acetate layer was dried over anhydrous magnesium sulfate, and the solvent was evaporated under reduced pressure to give a crude product. The resulting crude product was purified by column chromatography on silica gel using an eluting solvent of toluene/acetone=8/1 to give 86 mg of a mixture of Compounds 12 and 13 in a 100% yield.

Compounds 12 and 13 are isomers based on the methoxy group of the oxime. The mixture was separated by thin-layer chromatography with an eluting solvent of toluene/acetone=4/1 to give 40 mg of Compound 12 having the Rf value of 0.54, and 25 mg of Compound 13 having the Rf value of 0.49.

Compound 12:

HR-FAB-MS: Calculated; $C_{51}H_{75}NO_{14}[M+Na]^+$ 948.5084, Found; 948.5142 IR(KBr) $\lambda_{max}cm^{-1}$: 3467, 2967, 2933, 1735, 1716, 1457, 1157, 1118, 1041, 989 $^1$H NMR (270 MHz, CDCl$_3$, partial data) δ (ppm): 8.28 (1H, d, J=10.3 Hz), 6.09 (1H, d, J=10.3 Hz), 5.73 (5H, m), 5.54 (1H, dd, J=2.3, 9.9 Hz), 5.40 (3H, m), 4.99 (1H, m), 4.76 (1H, d, J=3.0 Hz), 4.67 (2H, s), 4.45 (1H, m), 4.29 (2H, m), 3.89 (3H, s), 3.45 (3H, s), 3.35 (3H, s), 1.87 (3H, s), 1.36 (3H, d, J=6.6 Hz), 1.25 (3H, d, J=6.3 Hz), 1.15 (3H, d, J=6.9 Hz)

Compound 13:

HR-FAB-MS: Calculated; $C_{51}H_{75}NO_{14}[M+Na]^+$ 948.5084, Found; 948.5093 IR(KBr) $\lambda_{max}cm^{-1}$: 3455, 2966, 2933, 1731, 1716, 1456, 1378, 1159, 1118, 1052, 995 $^1$H NMR (270 MHz, CDCl$_3$, partial data) δ (ppm): 7.63 (1H, d, J=9.6 Hz), 6.61 (1H, d, J=9.6 Hz), 5.85 (1H, m), 5.74 (3H, m), 5.55 (1H, dd, J=2.6, 9.9 Hz), 5.43 (4H, m), 4.99 (1H, m), 4.77 (1H, d, J=3.0 Hz), 4.67 (2H, s), 3.92 (3H, s), 3.45 (3H, s), 3.37 (3H, s), 1.87 (3H, s), 1.39 (3H, d, J=6.6 Hz), 1.15 (3H, d, J=6.9 Hz)

Example 12

Preparation of Compound 14

To a solution of 200 mg of Compound 5 obtained in Example 5 dissolved in 5 ml of isopropyl acetate, 30 mg of zinc(II) chloride and 175 μl of hexamethyldisilazane were added, and the mixture was heated to 50° C. and stirred. The reaction was continued at the same temperature for 3 hours. After the reaction mixture was cooled to 0° C., 25 mg of sodium borohydride was added thereto, and the mixture was stirred at room temperature for 1 hour. Saturated brine was added thereto, and then the mixture was extracted with ethyl acetate. The ethyl acetate layer was dried over anhydrous magnesium sulfate, and the solvent was evaporated under reduced pressure to give a crude product. The resulting crude product was purified by column chromatography on silica gel using stepwise elution with eluting solvents of hexane/acetone=3/1~2/1~1/1, and acetone and then methanol to give 16 mg of Compound 14 in a 10% yield.

HR-FAB-MS: Calculated; $C_{56}H_{89}NO_{13}Si[M+Na]^+$ 1034.5983, Found; 1034.5956 IR(KBr) $\lambda_{max}cm^{-1}$: 3482, 2962, 2931, 1735, 1716, 1457, 1380, 1160, 1124, 1083, 991 $^1$H NMR (270 MHz, CDCl$_3$, partial data) δ (ppm): 5.73 (5H, m), 5.54 (1H, dd, J=2.3, 9.9 Hz), 5.32 (3H, m), 4.98 (1H, m), 4.77 (1H, br.s), 4.68 (1H, d, J=15.8 Hz), 4.57 (1H, d, J=14.2 Hz), 4.39 (2H, m), 4.27 (1H, br.s), 3.44 (3H, s), 3.38 (3H, s), 1.78 (3H, s), 1.33 (3H, d, J=6.3 Hz), 1.14 (3H, d, J=6.9 Hz), 0.13 (6H, s)

Example 13

Preparation of Compounds 15 and 29

To 150 μl of a 1.0 mol/L tetrahydrofuran solution of lithium hexamethyldisilazane, 30 μl of diethylphosphonocyanomethyl was added, and the resulting mixture was stirred under ice-cooling (0° C.) for 30 minutes. Then, a solution of 109 mg of 5-O-tert-butyldimethylsilyl-4"-oxoavermectin B1a dissolved in 0.5 ml of tetrahydrofuran was added to the mixture, and the mixture was stirred at room temperature for 2 hours. The mixture was then treated and purified in the manners similar to those in Example 1 to give 90 mg of a mixture of Compounds 15 and 29 in a 80% yield.

Compounds 15 and 29 are isomers based on the 4"-exomethylene moiety. The mixture was separated by thin-layer chromatography using a developing solvent of toluene/ethyl acetate=4/1 to give 16 mg of Compound 15 having the Rf value of 0.59, and 57 mg of Compound 29 having the Rf value of 0.54.

Compound 29:

HR-FAB-MS: Calculated; $C_{56}H_{85}NO_{13}Si[M+Na]^+$ 1030.5670, Found; 1030.5688 IR(KBr) $\lambda_{max}cm^{-1}$: 3482, 2962, 2935, 2221, 1735, 1712, 1463, 1378, 1160, 1124, 1010, 991 $^1$H NMR (270 MHz, CDCl$_3$, partial data) δ (ppm): 5.73 (4H, m), 5.54 (1H, dd, J=2.6, 9.9 Hz), 5.45 (1H, t, J=4.3 Hz), 5.35 (3H, m), 4.98 (1H, m), 4.77 (1H, d, J=3.3 Hz), 4.68 (1H, d, J=14.9 Hz), 4.57 (1H, d, J=14.5 Hz), 4.45 (2H, m), 4.30 (1H, m), 3.48 (3H, s), 3.44 (3H, s), 1.78 (3H, s), 1.35 (3H, d, J=6.3 Hz), 1.14 (3H, d, J=6.9 Hz), 0.13 (6H, s)

Example 14

Preparation of Compound 16

In 0.5 ml of methylene chloride, 102 mg of Compound 3 obtained in Example 3 was dissolved, 0.2 ml of pyridine, 55 mg of nicotinoyl chloride hydrochloride and 13 mg of 4-dimethylaminopyridine were added thereto, and the mixture was stirred for 5 days. To the reaction solution was added an aqueous sodium hydrogencarbonate solution and the mixture was extracted with ethyl acetate. The ethyl acetate layer was dried over anhydrous sodium sulfate, and the solvent was evaporated under reduced pressure to give a crude product. The resulting crude product was purified by column chromatography on silica gel using stepwise elution with eluting solvents of hexane/ethyl acetate=10/1~6/1~2/1 to give 70 mg of Compound 16 in a 62% yield.

HR-FAB-MS: Calculated; $C_{62}H_{91}NO_{15}Si[M+Na]^+$ 1140.6055, Found; 1140.6058 IR(KBr) $\lambda_{max}cm^{-1}$: 3438, 2962, 2929, 1727, 1280, 1124, 987 $^1$H NMR (270 MHz, CDCl$_3$, partial data) δ (ppm): 9.21 (1H, d, J=1.6 Hz), 8.76 (1H, dd, J=1.6, 4.6 Hz), 8.28 (1H, dt, J=2.0, 8.2 Hz), 7.37 (1H, m), 5.72 (5H, m), 5.52 (1H, dd, J=2.5, 9.9 Hz), 5.39 (3H, m), 5.15 (1H, dd, J=7.6, 13.2 Hz), 5.01 (2H, m), 4.75 (1H, d, J=3.0 Hz), 4.66 (1H, d, J=16.2 Hz), 4.55 (1H, d, J=16.8 Hz), 4.32 (1H, br.s), 3.44 (3H, s), 3.36 (3H, s), 1.76 (3H, s), 1.35 (3H, d, J=6.6 Hz), 1.12 (3H, d, J=6.6 Hz), 0.11 (6H, s)

Example 15

Preparation of Compound 17

In 0.5 ml of methylene chloride, 102 mg of Compound 3 obtained in Example 3 was dissolved, 0.2 ml of pyridine, 52 mg of isonicotinoyl chloride hydrochloride and 12 mg of 4-dimethylaminopyridine were added thereto, and the mixture was stirred for 5 days. The reaction mixture was subjected to post-treatment and purified in the manners similar to those in Example 14 to give 51 mg of Compound 17 in a 46% yield.

HR-FAB-MS: Calculated; $C_{62}H_{91}NO_{15}Si[M+Na]^+$ 1140.6055, Found; 1140.6049 IR(KBr) $\lambda_{max}cm^{-1}$: 3450, 2962, 2933, 1731, 1461, 1378, 1276, 1160, 1124, 993 $^1$H NMR (270 MHz, CDCl$_3$, partial data) δ (ppm): 8.78 (2H, dd, J=1.7, 4.4 Hz), 7.85 (2H, dd, J=1.7, 4.4 Hz), 5.73 (5H, m), 5.55 (1H, dd, J=2.3, 9.9 Hz), 5.41 (2H, s), 5.14 (1H, dd, J=7.6, 13.2 Hz), 5.02 (2H, m), 4.77 (1H, d, J=3.0 Hz), 4.67 (1H, d, J=16.2 Hz), 4.57 (1H, d, J=16.2 Hz), 4.33 (1H, br.s), 4.12 (1H, s), 3.46 (3H, s), 3.38 (3H, s), 1.78 (3H, s), 1.37 (3H, d, J=6.6 Hz), 1.26 (3H, d, J=6.6 Hz), 1.14 (3H, d, J=6.9 Hz), 0.92 (9H, s), 0.13 (6H, s) $^{13}$C-NMR (67.8 MHz, CDCl$_3$) δ (ppm): 173.9, 164.9, 150.5, 150.5, 142.9, 140.1, 137.4, 137.3, 136.2, 135.1, 127.7, 124.7, 122.8, 122.8, 120.1, 119.3, 118.3, 117.3, 96.8, 95.7, 95.0, 82.0, 80.2, 80.1, 80.0, 79.0, 74.8, 73.4, 69.4, 68.4, 68.3, 67.9, 67.4, 67.3, 62.0, 56.9, 56.0, 45.7, 40.4, 39.6, 36.5, 35.1, 34.7, 34.2, 30.5, 27.4, 25.8, 25.8, 25.8, 20.2, 20.0, 18.4, 18.3, 18.0, 16.3, 15.1, 12.9, 12.0, −4.6, −4.9 (two peaks were not observed because of overlappings with other peaks.)

Example 16

Preparation of Compounds 18 and 19

To 150 μl of a 1.0 mol/L tetrahydrofuran solution of lithium hexamethyldisilazane, 40 μl of allyl diethylphosphonoacetate was added, and the resulting mixture was stirred under ice-cooling (0° C.) for 30 minutes. Then, a solution of 109 mg of 5-O-tert-butyldimethylsilyl-4"-oxoavermectin B1a dissolved in 0.5 ml of tetrahydrofuran was added to the mixture, and the mixture was stirred at room temperature for 3 hours. The mixture was then treated and purified in the manners similar to those in Example 1 to give 100 mg of a mixture of Compounds 18 and 19 in a 86% yield.

Compounds 18 and 19 are isomers based on the 4"-exomethylene moiety. The mixture was separated by thin-layer chromatography using an eluting solvent of toluene/ethyl acetate=6/1 to give 14 mg of Compound 18 having the Rf value of 0.49, and 69 mg of Compound 19 having the Rf value of 0.40.

Compound 18:

HR-FAB-MS: Calculated; $C_{59}H_{90}NO_{15}Si[M+Na]^+$ 1089.5946, Found; 1089.5914 IR(KBr) $\lambda_{max}cm^{-1}$: 3482, 2962, 2933, 1720, 1654, 1457, 1388, 1159, 1124, 1085, 989 $^1H$ NMR (270 MHz, CDCl$_3$, partial data) δ (ppm): 5.93 (2H, m), 5.74 (4H, m), 5.51 (2H, m), 5.32 (3H, m), 4.98 (1H, m), 4.76 (1H, d, J=3.0 Hz), 4.62 (2H, m), 4.43 (1H, br.s), 4.08 (1H, s), 3.92 (1H, br.s), 3.45 (3H, s), 3.24 (3H, s), 1.78 (3H, s), 1.24 (3H, d, J=5.9 Hz), 1.12 (3H, d, J=6.9 Hz), 0.92 (9H, s), 0.12 (6H, s)

Compound 19:

HR-FAB-MS: Calculated; $C_{59}H_{90}NO_{15}Si[M+Na]^+$ 1089.5946, Found; 1089.5908 IR(KBr) $\lambda_{max}cm^{-1}$: 3453, 2962, 2933, 1724, 1652, 1457, 1386, 1159, 1124, 1006, 991 $^1H$ NMR (270 MHz, CDCl$_3$, partial data) δ (ppm): 5.93 (1H, m), 5.87 (1H, s), 5.73 (4H, m), 5.54 (1H, d, J=2.3, 9.9 Hz), 5.46 (1H, m), 5.26 (4H, m), 5.15 (1H, s), 5.01 (1H, m), 4.77 (1H, br.s), 4.62 (3H, m), 4.52 (1H, m), 4.43(1H, br.s), 3.46 (3H, s), 3.37 (3H, s), 1.79 (3H, s), 1.42 (3H, d, J=6.6 Hz), 1.25 (3H, d, J=6.0 Hz), 1.14 (3H, d, J=6.9 Hz), 0.13 (6H, s)

Example 17

Preparation of Compound 20

In 2.0 ml of tetrahydrofuran, 213 mg of Compound 19 obtained in Example 16 was dissolved, 0.3 ml of the solution A was added thereto, and the mixture was stirred at room temperature for a night. Then, the reaction mixture was treated and purified in the manners similar to those in Example 2 to give 178 mg of Compound 20 in a 93% yield.

HR-FAB-MS: Calculated; $C_{53}H_{76}O_{15}[M+Na]^+$ 975.5081, Found; 975.5082 IR(KBr) $\lambda_{max}cm^{-1}$: 3475, 2967, 2933, 1722, 1652, 1456, 1382, 1159, 1120, 1010, 989 $^1H$ NMR (270 MHz, CDCl$_3$, partial data) δ (ppm): 5.95 (1H, m), 5.86 (2H, m), 5.73 (3H, m), 5.54 (1H, dd, J=2.3, 9.9 Hz), 5.41 (3H, m), 5.29 (2H, m), 5.13 (1H, s), 4.97 (1H, m), 4.76 (1H, d, J=3.0 Hz), 4.67 (1H, s), 4.62 (1H, d, J=6.0 Hz), 4.50 (1H, q, J=6.6 Hz), 4.28 (1H, d, J=5.0 Hz), 3.45 (3H, s), 3.36 (3H, s), 1.86 (3H, s), 1.41 (3H, d, J=6.6 Hz), 1.24 (3H, d, J=6.0 Hz), 1.13 (3H, d, J=6.9 Hz) $^{13}C$-NMR (67.8 MHz, CDCl$_3$) δ (ppm): 173.5, 165.2, 157.0, 139.5, 137.9, 137.8, 136.1, 135.0, 132.0, 127.7, 124.6, 120.3, 118.3, 118.2, 117.9, 116.6, 96.1, 95.7, 94.9, 81.8, 80.3, 80.2, 79.1, 78.8, 74.8, 70.0, 68.2, 68.1, 67.6, 67.3, 64.9, 60.3, 57.0, 56.4, 45.5, 39.7, 36.5, 35.0, 34.1, 33.3, 30.5, 27.4, 25.2, 20.9, 20.0, 19.8, 19.3, 17.8, 16.3, 15.0, 14.1, 12.9, 11.9

Example 18

Preparation of Compound 21

In 1.5 ml of tetrahydrofuran, 58 mg of Compound 16 obtained in Example 14 was dissolved, 0.3 ml of the solution A was added thereto, and the mixture was stirred at room temperature for a night. Then, the reaction mixture was treated and purified in the manners similar to those in Example 2 to give 52 mg of Compound 21 in an approximately 100% yield.

HR-FAB-MS: Calculated; $C_{56}H_{77}O_{15}[M+Na]^+$ 1026.5190, Found; 1026.5197 IR(KBr) $\lambda_{max}cm^{-1}$: 3475, 2967, 2933, 1727, 1591, 1456, 1280, 1118, 989 $^1H$ NMR (270 MHz, CDCl$_3$, partial data) δ (ppm): 9.23 (1H, d, J=1.6 Hz), 8.78 (1H, dd, J=1.6, 4.9 Hz), 8.30 (1H, dt, J=2.0, 7.9 Hz), 7.40 (1H, dd, J=4.9, 7.9 Hz), 5.74 (5H, m), 5.55 (1H, dd, J=2.3, 9.9 Hz), 5.41 (3H, m), 5.15 (1H, dd, J=7.6, 12.5 Hz), 5.02 (2H, m), 4.77 (1H, d, J=3.3 Hz), 4.68 (2H, s), 3.46 (3H, s), 3.38 (3H, s), 1.87 (3H, s), 1.37 (3H, d, J=6.6 Hz), 1.26 (3H, d, J=5.9 Hz), 1.20 (3H, d, J=6.9 Hz), 1.15 (3H, d, J=6.9 Hz) $^{13}C$-NMR (67.8 MHz, CDCl$_3$) δ (ppm): 173.6, 165.1, 156.4, 150.8, 142.7, 139.6, 138.0, 137.9, 137.1, 136.2, 135.1, 127.7, 126.0, 124.7, 123.3, 120.4, 120.3, 118.2, 118.0, 96.7, 95.7, 95.0, 81.9, 80.3, 80.1, 79.1, 79.0, 74.8, 73.3, 68.3, 68.3, 67.7, 67.4, 67.3, 61.6, 56.9, 56.0, 53.4, 45.6, 40.4, 39.7, 36.6, 35.1, 34.7, 34.2, 34.1, 30.5, 27.4, 20.1, 19.9, 18.3, 18.0, 16.3, 15.0, 12.9, 12.0

Example 19

Preparation of Compound 22

To a solution of 38 mg of Compound 5 obtained in Example 5 dissolved in 0.1 ml of ethanol, 12 mg of semicarbazide hydrochloride and 0.2 ml of pyridine were added, and the resulting mixture was stirred at room temperature for a night. To the reaction solution was added an aqueous sodium hydrogencarbonate solution and the mixture was extracted with ethyl acetate. The ethyl acetate layer was dried over anhydrous magnesium sulfate, and the solvent was evaporated under reduced pressure to give a crude product.

The resulting crude product was dissolved in 0.8 ml of tetrahydrofuran, 0.4 ml of the solution A was added thereto, and the mixture was stirred at room temperature for 4 hours. After pyridine and an aqueous sodium hydrogencarbonate solution were added to the mixture, the mixture was extracted with ethyl acetate. The ethyl acetate layer was dried over anhydrous magnesium sulfate, and the solvent was evaporated to give a crude product. The resulting crude product was purified by thin-layer chromatography on silica gel of 0.5 mm thickness using an eluting solvent of methylene chloride/methanol=15/1 to give 8 mg of Compound 22 in a 25% yield.

HR-FAB-MS: Calculated; $C_{51}H_{75}N_3O_{14}[M+Na]^+$ 976.5146, Found; 976.5147 IR(KBr) $\lambda_{max}cm^{-1}$: 3488, 2967, 2933, 1695, 1577, 1457, 1160, 1118, 989 $^1H$ NMR (270 MHz, CDCl$_3$, partial data) δ (ppm): 8.64 (1H, br.s), 8.02 (1H, d, J=9.3 Hz), 6.08 (1H, d, J=9.3 Hz), 5.85 (1H, m), 5.74 (3H, m), 5.55 (1H, dd, J=2.3, 9.9 Hz), 5.40 (3H, m), 4.99 (1H, m), 4.77 (1H, d, J=3.0 Hz), 4.67 (1H, s), 3.45 (3H, s), 3.38 (3H, s), 1.86 (3H, s), 1.37 (3H, d, J=6.2 Hz), 1.25 (3H, d, J=6.3 Hz), 1.15 (3H, d, J=6.9 Hz)

Example 20

Preparation of Compound 23

In 1 ml of tetrahydrofuran, 100 mg of Compound 29 obtained in Example 13 was dissolved, 0.4 ml of the solution A was added thereto, and the mixture was stirred at room temperature for a night. Then, the reaction mixture was treated and purified in the manners similar to those in Example 2 to give 82 mg of Compound 23 in a 92% yield.

HR-FAB-MS: Calculated; $C_{50}H_{71}N_3O_{13}[M+Na]^+$ 916.4882, Found; 916.4813 IR(KBr) $\lambda_{max}cm^{-1}$: 3463, 2933, 2931, 2221, 1735, 1716, 1657, 1378, 1118, 1052, 1010 $^1$H NMR (270 MHz, CDCl$_3$, partial data) δ (ppm): 5.81 (1H, m), 5.71 (3H, m), 5.51 (1H, d, J=9.9 Hz), 5.34 (4H, m), 4.95 (1H, m), 4.74 (1H, d, J=3.3 Hz), 4.63 (2H, s), 4.43 (1H, m), 4.25 (2H, m), 4.08 (1H, br.s), 3.44 (3H, s), 3.40 (3H, s), 1.82 (3H, s), 1.32 (3H, d, J=6.3 Hz) $^{13}$C-NMR (67.8 MHz, CDCl$_3$) δ (ppm): 173.5, 163.3, 139.5, 137.7, 136.2, 135.0, 127.6, 124.7, 120.2, 118.2, 117.9, 115.9, 97.0, 95.7, 94.9, 93.9, 81.9, 80.6, 80.3, 79.1, 78.9, 75.3, 74.8, 68.2, 68.2, 67.6, 67.0, 66.6, 64.1, 57.7, 56.6, 45.6, 40.4, 39.6, 36.8, 36.4, 35.0, 34.5, 34.1, 30.4, 27.4, 20.1, 19.8, 18.0, 17.5, 16.2, 15.0, 12.8, 11.9

Example 21

Preparation of Compound 24

In 2 ml of ethanol, 120 mg of Compound 18 obtained in Example 16 was dissolved, 30 mg of sodium borohydride and 1 mg of tetrakis(triphenylphosphono)palladium were added thereto, and the mixture was stirred at room temperature for 20 minutes. Saturated brine was added thereto, and then the mixture was extracted with ethyl acetate. The ethyl acetate layer was dried over anhydrous magnesium sulfate, and the solvent was evaporated under reduced pressure to give a crude product. The resulting crude product was purified by column chromatography on silica gel using an eluting solvent of hexane/2-propanol=85/15 to give 75 mg of Compound 24 in a 63% yield.

HR-FAB-MS: Calculated; C$_{56}$H$_{86}$O$_{15}$Si[M+Na]$^+$ 1049.5633, Found; 1049.5634 IR(KBr) λ$_{max}$cm$^{-1}$: 3482, 2962, 2933, 1716, 1654, 1459, 1380, 1159, 1124, 1085, 1006 $^1$H NMR (270 MHz, CDCl$_3$, partial data) δ (ppm): 5.86 (1H, s), 5.70 (4H, m), 5.53 (1H, dd, J=2.3, 9.9 Hz), 5.45 (1H, m), 5.31 (3H, m), 5.06 (1H, m), 4.98 (1H, m), 4.75 (1H, s), 4.67 (1H, d, J=15.0 Hz), 4.55 (1H, d, J=15.0 Hz), 4.48 (1H, m), 4.43 (1H, br.s), 3.44 (3H, s), 3.37 (3H, s), 1.77 (3H, s), 1.40 (3H, d, J=6.6 Hz), 1.11 (3H, d, J=6.9 Hz), 0.13 (6H, s)

Example 22

Preparation of Compound 25

In 1.5 ml of tetrahydrofuran, 183 mg of Compound 24 obtained in Example 21 was dissolved, 0.2 ml of the solution A was added thereto, and the mixture was stirred at room temperature for a night. Then, the reaction mixture was treated and purified in the manners similar to those in Example 2 to give 62 mg of Compound 25 in a 38% yield.

HR-FAB-MS: Calculated; C$_{50}$H$_{72}$O$_{15}$[M+Na$_2$—H]$^+$ 957.4588, Found; 957.4670 IR(KBr) λ$_{max}$cm$^{-1}$: 3469, 2967, 2933, 1716, 1654, 1456, 1378, 1160, 1120, 1008, 991 $^1$H NMR (270 MHz, CDCl$_3$, partial data) δ (ppm): 5.95 (1H, m), 5.85 (3H, m), 5.62 (1H, dd, J=2.3, 9.9 Hz), 5.57 (1H, m), 5.40 (2H, m), 5.07 (1H, m), 4.86 (1H, s), 4.77 (2H, s), 4.38 (1H, d, J=6.0 Hz), 3.55 (3H, s), 3.33 (3H, s), 1.95 (3H, s), 1.34 (3H, d, J=6.3 Hz), 1.22 (3H, d, J=6.6 Hz)

Example 23

Preparation of Compound 26

In 1.5 ml of tetrahydrofuran, 46 mg of Compound 17 obtained in Example 15 was dissolved, 0.2 ml of the solution A was added thereto, and the mixture was stirred at room temperature for a night. The reaction mixture was treated and purified in the manners similar to those in Example 2 to give 42 mg of Compound 26 in an approximately 100% yield.

HR-FAB-MS: Calculated; C$_{56}$H$_{77}$O$_{15}$[M+Na$_2$—H]$^+$ 1026.5190, Found; 1026.5225 IR(KBr) λ$_{max}$cm$^{-1}$: 3477, 2967, 2933, 1731, 1457, 1278, 1120, 989 $^1$H NMR (270 MHz, CDCl$_3$, partial data) δ (ppm): 8.77 (2H, dd, J=1.6, 4.2 Hz), 7.86 (2H, dd, J=1.6, 4.2 Hz), 5.83 (1H, m), 5.73 (4H, m), 5.54 (1H, dd, J=2.3, 9.9 Hz), 5.41 (3H, m), 5.13 (1H, dd, J=7.2, 13.2 Hz), 5.03 (2H, m), 4.76 (1H, d, J=3.0 Hz), 4.66 (2H, s), 3.45 (3H, s), 3.37 (3H, s), 1.85 (3H, s), 1.35 (3H, d, J=6.6 Hz), 1.25 (3H, d, J=5.9 Hz), 1.14 (3H, d, J=6.9 Hz) $^{13}$C-NMR (67.8 MHz, CDCl$_3$) δ (ppm): 173.4, 164.8, 150.3, 150.3, 142.8, 139.5, 137.8, 137.6, 137.3, 136.1, 135.0, 137.6, 124.6, 122.8, 122.8, 120.2, 120.1, 118.1, 117.9, 96.7, 95.6, 95.0, 81.8, 80.2, 80.1, 79.1, 78.9, 74.7, 73.3, 68.2, 68.2, 67.6, 67.2, 64.0, 62.0, 56.8, 55.9, 45.5, 40.3, 39.6, 36.4, 35.0, 34.6, 34.1, 34.0, 30.4, 27.3, 20.1, 19.8, 18.2, 17.9, 16.2, 15.0, 12.8, 12.0 (one peak was not observed because of overlapping with another one.)

Example 24

Preparation of Compound 27

In 0.25 ml of methylene chloride, 21 mg of Compound 3 obtained in Example 3 was dissolved, 5 mg of pyrrole-2-carboxylic acid, 6 mg of 4-dimethylaminopyridine and 10 mg of 1-ethyl-3-(3-dimethylaminopropyl)carbodiimide hydrochloride (WSCI hydrochloride) were added thereto, and then the mixture was stirred at room temperature for a night. The reaction mixture was subjected to post-treatment and purified in the manners similar to those in Example 14. The resulting crude product was dissolved in 0.5 ml of tetrahydrofuran, 0.2 ml of the solution A was added thereto, and the mixture was stirred at room temperature for 5 hours. The mixture was then treated and purified in the manners similar to those in Example 2 to give 8 mg of Compound 27 in a 62% yield.

HR-FAB-MS: Calculated; C$_{55}$H$_{77}$O$_{15}$[M+Na$_2$—H]$^+$ 1014.5190, Found; 1014.5156 IR(KBr) λ$_{max}$cm$^{-1}$: 3469, 2967, 2933, 1706, 1556, 1452, 1413, 1378, 1309, 1160, 1120 $^1$H NMR (270 MHz, CDCl$_3$, partial data) δ (ppm): 9.45 (1H, br.s), 6.93 (2H, m), 6.25 (1H, m), 5.72 (5H, m), 5.53 (1H, dd, J=2.6, 9.3 Hz), 5.40 (3H, m), 4.75 (1H, d, J=3.3 Hz), 4.66 (2H, s), 3.94 (1H, d, J=6.3 Hz), 3.45 (3H, s), 3.34 (3H, s), 1.85 (3H, s), 1.35 (3H, d, J=6.6 Hz), 1.24 (3H, d, J=6.2 Hz), 1.13 (3H, d, J=6.5 Hz) $^{13}$C-NMR (67.8 MHz, CDCl$_3$) δ (ppm): 173.6, 161.0, 142.0, 139.5, 138.1, 137.8, 136.2, 135.1, 127.7, 124.6, 123.1, 122.5, 121.4, 120.4, 118.2, 118.0, 115.5, 110.4, 96.6, 95.7, 95.0, 81.9, 80.3, 80.0, 79.1, 79.0, 74.8, 73.0, 68.3, 68.2, 67.7, 67.5, 60.4, 57.0, 55.9, 50.7, 45.7, 40.4, 39.7, 36.5, 35.1, 34.7, 34.2, 33.9, 30.5, 27.4, 20.1, 19.9, 18.5, 18.0, 16.3, 15.0, 12.9, 12.0

Example 25

Preparation of Compound 28

In 0.4 ml of methylene chloride, 36 mg of Compound 3 obtained in Example 3 was dissolved, 15 mg of N-(tert-butoxycarbonyl)proline, 8 mg of 4-dimethylaminopyridine and 17 mg of 1-ethyl-3-(3-dimethylaminopropyl) carbodiimide hydrochloride (WSCI hydrochloride) were added thereto, and then the mixture was stirred at room temperature for a night. The reaction mixture was subjected to post-treatment and purified in the manners similar to those in Example 14 to give 42 mg of Compound 28 in a 98% yield.

HR-FAB-MS: Calculated; C$_{66}$H$_{103}$NO$_{17}$Si[M+Na]$^+$ 1232.6892, Found; 1232.6901 IR(KBr) λ$_{max}$cm$^{-1}$: 3453, 1962, 1745, 1706, 1457, 1396, 1160, 1124, 1085, 989 $^1$H NMR (270 MHz, CDCl$_3$, partial data) δ (ppm): 5.72 (4H, m), 5.54 (1H, dd, J=2.3, 9.9 Hz), 5.52 (1H, m), 5.34 (3H, m), 4.76 (1H, br.s), 4.67 (1H, dd, J=2.0, 14.5 Hz), 4.57 (1H, dd, J=2.0, 14.5 Hz), 4.10 (1H, s), 3.92 (1H, br.s), 3.45 (3H, s), 3.32 (3H, d, J=4.3 Hz), 1.78 (3H, s), 1.42 (3H, s), 1.40 (6H, s), 1.33 (3H, d, J=6.6 Hz), 1.24 (3H, d, J=6.3 Hz), 1.13 (3H, d, J=6.9 Hz), 0.12 (6H, s)

Example 26

Preparation of Compound 30

In 1.0 ml of tetrahydrofuran, 10 mg of Compound 28 obtained in Example 25 was dissolved, 0.1 ml of the solution A was added thereto, and the mixture was stirred at room temperature for a night. Then, the reaction mixture was treated and purified in the manners similar to those in Example 2 to give 7 mg of Compound 30 in a 79% yield.

HR-FAB-MS: Calculated; $C_{60}H_{89}NO_{17}[M+Na]^+$ 1118.6027, Found; 1118.6050 IR(KBr) $\lambda_{max}cm^{-1}$: 3475, 2971, 1743, 1706, 1454, 1396, 1160, 1120, 989 $^1$H NMR (270 MHz, CDCl$_3$, partial data) δ (ppm): 5.72 (4H, m), 5.54 (1H, dd, J=2.3, 9.9 Hz), 5.52 (1H, m), 5.40 (3H, m), 5.06 (1H, m), 4.75 (1H, br.s), 4.66 (2H, s), 4.37 (1H, m), 3.94 (1H, d, J=6.3 Hz), 3.92 (1H, s), 3.43 (3H, s), 3.31 (3H, d, J=4.3 Hz), 1.85 (3H, s), 1.47 (3H, s), 1.43 (3H, s), 1.39 (3H, s), 1.32 (3H, d, J=6.3 Hz), 1.23 (3H, d, J=6.3 Hz), 1.13 (3H, d, J=6.9 Hz)

Example 27

Preparation of Compounds 38 and 39

In 3 ml of methylene chloride, 240 mg of Compound 4 obtained in Example 4 was dissolved, 0.4 g of manganese dioxide was added thereto, and the mixture was stirred for 2 days. The reaction solution was diluted with ethyl acetate and passed through a dry silica gel column, and the silica gel column was washed with ethyl acetate. The solution obtained was concentrated under reduced pressure to give a crude product. The resulting crude product was purified by column chromatography on silica gel using stepwise elution with eluting solvents of hexane/ethyl acetate=2/1 to 1/1 to give 12 mg of Compound 38 in a 5% yield and 20 mg of Compound 39 in a 8% yield.
Compound 38:

HR-FAB-MS: Calculated; $C_{50}H_{70}NO_{14}[M+Na]^+$ 917.4662, Found; 917.4709 IR(KBr) $\lambda_{max}cm^{-1}$: 3475, 2966, 2933, 1737, 1681, 1456, 1378, 1160, 1116, 991 $^1$H NMR (270 MHz, CDCl$_3$, partial data) δ (ppm): 10.32 (1H, d, J=7.3 Hz), 6.57 (1H, s), 5.91 (2H, m), 5.75 (3H, m), 5.56 (1H, dd, J=2.6, 9.9 Hz), 5.47 (2H, m), 5.00 (1H, m), 4.79 (1H, s), 4.74 (1H, s), 4.54 (1H, m), 3.96 (1H, d, J=9.2 Hz), 3.45 (3H, s), 3.43 (3H, s), 1.88 (3H, s), 1.36 (3H, d, J=6.3 Hz)
Compound 39:

HR-FAB-MS: Calculated; $C_{50}H_{72}NO_{14}[M+Na]^+$ 919.4819, Found; 919.4816 IR(KBr) $\lambda_{max}cm^{-1}$: 3475, 2968, 2933, 1737, 1681, 1454, 1380, 1160, 1120, 991 $^1$H NMR (270 MHz, CDCl$_3$, partial data) δ (ppm): 6.57 (1H, s), 5.94 (1H, m), 5.76 (3H, m), 5.55 (1H, dd, J=2.3, 9.9 Hz), 5.43 (2H, m), 4.99 (1H, m), 4.74 (3H, m), 3.44 (3H, s), 3.39 (3H, s), 1.89 (3H, s)

Example 28

Preparation of Compound 40

To 0.85 ml of a 1.0 mol/L tetrahydrofuran solution of lithium hexamethyldisilazane, 0.2 ml of methyl diethylphosphonoacetate was added, and the resulting mixture was stirred under ice-cooling (0° C.) for 30 minutes. Then, a solution of 400 mg of the compound [a] obtained in Reference Example 1 dissolved in 1.5 ml of tetrahydrofuran was added thereto, and the mixture was stirred at room temperature for 3 hours. The mixture was then subjected to post-treatment and purified in the manners similar to those in Example 1 to give 325 mg of Compound 40 in a 77% yield.

HR-FAB-MS: Calculated; $C_{57}H_{88}O_{16}Si[M+Na]^+$ 1079.5738, Found; 1079.5693 IR(KBr) $\lambda_{max}cm^{-1}$: 3473, 2962, 2935, 1724, 1458, 1384, 1245, 1124, 1012, 987 $^1$H NMR (270 MHz, CDCl$_3$, partial data) δ (ppm): 5.81 (1H, s), 5.76 (1H, m), 5.69 (2H, m), 5.41 (1H, m), 5.30 (1H, s), 5.26 (1H, m), 5.10 (1H, br.s), 4.90 (1H, br.t, J=7.1 Hz), 4.71 (1H, d, J=3.0 Hz), 4.64 (1H, d, J=16.2 Hz), 4.53 (1H, d, J=16.2 Hz), 4.39 (1H, m), 3.95 (1H, s), 3.89 (1H, br.s), 3.78 (1H, d, J=6.6 Hz), 3.69 (3H, s), 3.41 (3H, s), 3.33 (3H, s), 1.66 (3H, s), 1.38 (3H, d, J=6.3 Hz), 1.09 (3H, d, J=6.9 Hz), 0.10 (6H, s) $^{13}$C-NMR (67.8 MHz, CDCl$_3$) δ (ppm): 206.9, 173.7, 166.1, 156.7, 140.0, 137.5, 137.5, 135.5, 124.7, 119.3, 117.6, 117.1, 116.6, 100.5, 96.0, 94.8, 81.6, 80.2, 80.2, 80.1, 80.0, 78.8, 76.4, 70.1,69. 3, 68.1, 68.1, 67.8, 67.7, 67.3, 60.3, 57.0, 56.4, 51.3, 46.4, 45.6, 40.4, 39.5, 35.9, 35.8, 34.7, 33.7, 33.4, 27.1, 25.8, 25.8, 25.8, 20.0, 19.3, 18.3, 17.8, 15.0, 12.3, 11.5, 8.7, −4.7, −5.0

Example 29

Preparation of Compound 41

In 2.5 ml of tetrahydrofuran, 208 mg of Compound 40 obtained in Example 28 was dissolved, 1.5 ml of the solution A was added thereto, and the mixture was stirred at room temperature for a night. The reaction mixture was then treated and purified in the manners similar to those in Example 2 to give 137 mg of Compound 41 in a 73% yield.

HR-FAB-MS: Calculated; $C_{51}H_{74}O_{16}[M+Na]^+$ 965.4874, Found; 965.4835 IR(KBr) $\lambda_{max}cm^{-1}$: 3477, 2971, 2935, 1724, 1459, 1387, 1340, 1240, 1197, 1164, 1122, 1060, 1012, 987 $^1$H NMR (270 MHz, CDCl$_3$, partial data) δ (ppm): 5.83 (2H, s), 5.71 (2H, m), 5.43 (2H, s), 5.33 (1H, m), 5.13 (1H, m), 4.93 (1H, m), 4.74 (1H, d, J=3.0 Hz), 4.66 (2H, s), 4.49(1H, q, J=6.6 Hz), 4.28 (1H, m), 3.71 (3H, s), 3.43 (3H, s), 3.35 (3H, s), 1.86 (3H, s), 1.40 (3H, d, J=6.6 Hz), 1.23 (3H, d, J=5.9 Hz),1.13 (3H, d, J=6.9 Hz) $^{13}$C-NMR (67.8 MHz, CDCl$_3$) δ (ppm): 207.0, 173.5, 166.2, 156.7, 139.5, 138.1, 135.5, 125.2, 124.6, 120.4, 117.9, 117.6, 116.6, 100.5, 96.1, 94.8,8 1.6, 80.4, 80.4, 80.2, 79.1, 78.9, 70.1,68.3, 68.2, 68.2, 67.6, 67.6, 67.4, 57.0, 56.5, 51.3, 46.5, 45.6, 40.4, 39.7, 36.0, 35.9, 34.8, 33.7, 33.4, 27.2, 20.1, 19.9, 19.4, 17.9, 15.1, 12.3, 11.6, 8.7

Example 30

Preparation of Compound 31

In 0.6 ml of methylene chloride, 61 mg of Compound 3 obtained in Example 3 was dissolved, 10 μl of 3,4-dihydro-2H-pyran and 5 mg of pyridinium p-toluene-sulfonate were added thereto, and the mixture was stirred at room temperature for 45 minutes. The reaction mixture was then subjected to post-treatment and purified in the manners similar to those in Example 14. The resulting 5-O-tert-butyldimethylsilyl-4"-[(2-tetrahydropyranyloxy)ethylidene]avermectin B1a was dissolved in 2 ml of tetrahydrofuran, 0.2 ml of the solution A was added thereto, and the mixture was stirred at room temperature for a night. Then, the mixture was treated and purified in the manners similar to those in Example 2 to give 35 mg of Compound 31 in a 59% yield.

HR-FAB-MS: Calculated; $C_{55}H_{82}O_{15}[M+Na]^+$ 1005.5550, Found; 1005.5517 IR(KBr) $\lambda_{max}cm^{-1}$: 3473, 2966, 2933, 1737, 1716, 1456, 1380, 1159, 1118, 991 $^1H$ NMR (270 MHz, CDCl$_3$, partial data) δ (ppm): 5.85 (1H, m), 5.73 (3H, m), 5.54 (1H, dd, J=2.6, 9.9 Hz), 5.37 (3H, m), 4.98 (1H, m), 4.75 (1H, d, J=3.0 Hz), 4.67 (1H, s), 4.61 (1H, m), 4.42 (1H, m), 4.02 (1H, s), 3.95 (1H, d, J=7.3 Hz), 3.45 (3H, s), 3.30 (3H, d, J=4.3 Hz), 1.96 (3H, s), 1.36 (3H, d, J=6.3 Hz), 1.25 (3H, d, J=5.9 Hz), 1.13 (3H, d, J=6.9 Hz)

Example 31

Preparation of Compound 32

In 10 drops of pyridine, 27 mg of Compound 3 obtained in Example 3 was dissolved, 3 drops of acetic anhydride was added thereto, and the mixture was stirred at room temperature for a night. Toluene was added to the mixture, and the solvent was evaporated under reduce pressure to give a crude product. The resulting crude product was purified by thin-layer chromatography on silica gel of 0.5 mm thickness using a developing solvent of hexane/2-propanol=85/15 to give 23 mg of Compound 32 in a 98% yield.

IR(KBr) $\lambda_{max}cm^{-1}$: 3467, 2962, 2933, 1741, 1718, 1459, 1376, 1234, 1124, 1085, 995 $^1H$ NMR (270 MHz, CDCl$_3$, partial data) δ (ppm): 5.73 (4H, m), 5.55 (2H, m), 5.34 (3H, m), 4.99 (1H, m), 4.83 (1H, dd, J=7.3, 13.5 Hz), 4.66 (1H, d, J=14.8 Hz), 4.58 (1H, d, J=14.5 Hz), 4.42 (2H, m), 4.25 (1H, br.s), 4.02 (1H, br.s), 3.45 (3H, s), 3.33 (3H, s), 2.06 (3H, s), 1.78 (3H, s), 1.35 (3H, d, J=6.6 Hz), 1.14 (3H, d, J=6.9 Hz), 0.12 (6H, s) $^{13}$C-NMR (67.8 MHz, CDCl$_3$) δ (ppm): 174.1, 170.9, 142.1, 140.2, 137.6, 137.5, 136.2, 135.2, 127.8, 124.8, 121.2, 119.3, 118.3, 117.2, 96.7, 95.8, 95.1, 80.2, 80.1, 80.0, 79.0, 74.8, 73.0, 69.5, 68.4, 68.3, 67.9, 67.5, 60.7, 57.0, 56.0, 45.8, 40.5, 39.7, 36.6, 35.2, 34.3, 34.0, 30.6, 27.5, 25.9, 25.3, 21.0, 20.2, 20.0, 18.5, 18.4, 18.0, 16.4, 15.1, 13.0, 12.0, −4.6, −4.9

Example 32

Preparation of Compound 33

In 0.3 ml of methylene chloride, 77 mg of Compound 3 obtained in Example 3 was dissolved, 0.1 mg of pyridine, 42 mg of 6-chloronicotinoyl chloride and 9 mg of 4-dimethylaminopyridine were added thereto, and the mixture was stirred for 2 days. After the reaction was finished, an aqueous sodium hydrogencarbonate solution was added thereto, and the mixture was extracted with ethyl acetate. The ethyl acetate layer was dried over anhydrous sodium sulfate, and the solvent was evaporated under reduce pressure to give a crude product. The resulting crude product was purified by column chromatography on silica gel using stepwise elution with eluting solvents of hexane/ethyl acetate=4/1 to 1/1 to give 82 mg of Compound 33 in a 95% yield.

HR-FAB-MS: Calculated; $C_{61}H_{90}ClNO_{15}Si[M+Na]^+$ 1174.5665, Found; 1174.5669 $^1H$ NMR (270 MHz, CDCl$_3$, partial data) δ (ppm): 8.98 (1H, d, J=2.3 Hz), 8.22 (1H, dd, J=2.3, 8.2 Hz), 7.39 (1H, d, J=8.2 Hz), 5.75 (4H, m), 5.62 (1H, t, J=6.6 Hz), 5.52 (1H, dd, J=2.3, 9.9 Hz), 5.35 (3H, m), 5.12 (1H, dd, J=7.3, 13.7 Hz), 4.98 (2H, m), 4.74 (1H, d, J=3.0 Hz), 4.65 (1H, d, J=16.1 Hz), 4.55 (1H, d, J=16.1 Hz), 4.40 (1H, br.d, J=5.6 Hz), 4.30 (1H, br.s), 3.90 (1H, s), 3.79 (1H, d, J=5.6 Hz), 3.43 (3H, s), 3.35 (3H, s), 1.75 (3H, s), 1.34 (3H, d, J=6.6 Hz), 1.12 (3H, d, J=6.9 Hz), 0.10 (6H, s)

Example 33

Preparation of Compound 34

In 1 ml of tetrahydrofuran, 75 mg of Compound 33 obtained in Example 32 was dissolved, 0.2 ml of the solution A was added thereto, and the mixture was stirred at room temperature for a night. Then, the reaction mixture was treated and purified in the manners similar to those in Example 2 to give 54 mg of Compound 34 in a 80% yield.

HR-FAB-MS: Calculated; $C_{56}H_{76}ClNO_{15}[M+Na]^+$ 1060.4800, Found; 1060.4824 $^1H$ NMR (270 MHz, CDCl$_3$, partial data) δ (ppm): 8.97 (1H, d, J=2.3 Hz), 8.22 (1H, dd, J=2.3, 8.2 Hz), 7.39 (1H, d, J=8.2 Hz), 5.76 (4H, m), 5.63 (1H, t, J=6.3 Hz), 5.53 (1H, dd, J=2.3, 9.9 Hz), 5.39 (3H, m), 5.12 (1H, dd, J=7.3, 13.2 Hz), 4.99 (2H, m), 4.75 (1H, d, J=3.0 Hz), 4.66 (2H, s), 4.41 (1H, q, J=6.3 Hz), 4.20 (2H, m), 4.02 (1H, s), 3.94 (1H, d, J=6.3 Hz), 3.44 (3H, s), 3.36 (3H, s), 1.85 (3H, s), 1.34 (3H, d, J=6.6 Hz), 1.13 (3H, d, J=6.9 Hz) $^{13}$C-NMR (67.8 MHz, CDCl$_3$) δ (ppm): 173.6, 164.2, 155.6, 151.1, 142.9, 139.6, 139.5, 138.0, 137.9, 136.2, 135.1, 127.7, 125.0, 124.6, 124.1, 120.3, 120.1, 118.2, 118.0, 96.8, 95.7, 95.0, 81.9, 80.3, 80.0, 79.1, 79.0, 74.8, 73.4, 68.4, 68.3, 68.3, 67.6, 67.4, 67.3, 61.9, 56.9, 56.0, 45.6, 40.4, 39.7, 36.5, 35.1, 34.7, 34.2, 30.5, 27.4, 20.1, 19.9, 18.3, 18.0, 16.3, 15.0, 12.9, 12.0 (one peak was not observed because of overlapping with another peak.)

Example 34

Preparation of Compound 35

In 0.2 ml of chloroform, 30 mg of Compound 24 obtained in Example 21 was dissolved, 4 μl of morpholine, 3.6 mg of 4-dimethylaminopyridine and 7.5 mg of 1,3-dicyclohexylcarbodiimide were added thereto, and then the mixture was stirred under nitrogen atmosphere at room temperature for 4 hours. Water was added thereto, and then the mixture was extracted with chloroform. The chloroform layer was dried over anhydrous sodium sulfate, and the solvent was evaporated under reduced pressure to give a crude product. The resulting crude product was purified by column chromatography on silica gel using stepwise elution with eluting solvents of toluene/2-propanol=100/1~50/1~25/1~12.5/1 to give 24 mg of Compound 35 in a 72% yield.

IR(KBr) $\lambda_{max}cm^{-1}$: 3446, 2960, 2929, 1735, 1637, 1461, 1120, 995 $^1H$ NMR (270 MHz, CDCl$_3$, partial data) δ (ppm): 5.73 (4H, m), 5.54 (1H, dd, J=2.3, 9.9 Hz), 5.45 (1H, m), 5.33 (2H, m), 4.99 (1H, m), 4.76 (1H, br.s), 4.68 (1H, d, J=14.2 Hz), 4.58 (1H, d, J=15.5 Hz), 4.43 (2H, m), 4.29 (1H, m), 3.44 (3H, s), 3.36 (3H, s), 1.79 (3H, s), 1.35 (3H, d, J=6.6 Hz), 1.15 (3H, d, J=6.9 Hz), 0.13 (6H, s)

Example 35

Preparation of Compound 36

In 1.5 ml of tetrahydrofuran, 47 mg of Compound 35 obtained in Example 34 was dissolved, 0.2 ml of the solution A was added thereto, and the mixture was stirred at room temperature for a night. The reaction mixture was then treated and purified in the manners similar to those in Example 2 to give 24 mg of Compound 36 in a 57% yield.

HR-FAB-MS: Calculated; $C_{54}H_{79}NO_{15}Na\ [M+Na]^+$ 1004.5349, Found; 1004.5352 $^1H$ NMR (270 MHz, CDCl$_3$, partial data) δ (ppm): 5.85 (5H, m), 5.54 (1H, dd, J=2.6, 9.9 Hz), 5.41 (3H, m), 4.98 (1H, m), 4.76 (1H, br.s), 4.67 (2H, s), 3.44 (3H, s), 3.35 (3H, s), 1.86 (3H, s), 1.35 (3H, d, J=6.3

Hz), 1.23 (3H, d, J=6.3 Hz), 1.18 (3H, d, J=6.9 Hz) $^{13}$C-NMR (67.8 MHz, CDCl$_3$) δ (ppm): 173.7, 168.1, 145.6, 139.6, 138.0, 137.9, 136.3, 135.1, 127.7, 124.7, 120.4, 118.3, 118.0, 116.8, 97.5, 95.7, 95.0, 81.9, 80.4, 80.3, 79.2, 79.1, 74.9, 74.4, 68.4, 68.3, 67.7, 67.2, 66.6, 66.3, 57.3, 56.7, 47.0, 45.7, 41.5, 40.4, 39.7, 36.6, 35.8, 35.1, 34.6, 34.2, 30.6, 27.5, 20.2, 19.9, 18.2, 17.5, 16.3, 15.1, 12.9, 12.0 (two peaks were not observed because of overlappings with the other ones.)

Example 36

Preparation of Compound 37

In 0.2 ml of methylene chloride, 30 mg of Compound 24 obtained in Example 21 was dissolved, 2 drops of furfuryl alcohol, 10 mg of 4-dimethylaminopyridine and 11 mg of WSCI hydrochloride were added thereto, and then the mixture was stirred at room temperature for a night. The reaction mixture was subjected to post-treatment and purified in the manners similar to those in Example 14 to give 5-O-tert-butyldimethylsilyl-4"-furfuryloxycarbonylmethylideneavermectin B1a. The 5-O-tert-butyldimethylsilyl-4"-furfuryloxycarbonylmethylideneavermectin B1a obtained was dissolved in 1.0 ml of tetrahydrofuran, 0.2 ml of the solution A was added thereto, and the mixture was stirred at room temperature for a night. Then, the mixture was treated and purified in the manners similar to those in Example 2 to give 8 mg of Compound 37 in a 62% yield.

HR-FAB-MS: Calculated; $C_{55}H_{76}O_{16}Na$ [M+Na]$^+$ 1015.5032, Found; 1015.5031 $^1$H NMR (270 MHz, CDCl$_3$, partial data) δ (ppm): 7.42 (1H, d, J=1.0 Hz), 6.41 (1H, d, J=3.3 Hz), 6.36 (1H, m), 5.85 (2H, m), 5.73 (3H, m), 5.54 (1H, dd, J=2.6, 9.9 Hz), 5.41 (3H, m), 4.99 (1H, m), 4.75 (1H, d, J=3.9 Hz), 4.67 (2H, s), 4.48 (1H, dq, J=1.7, 6.6 Hz), 4.29 (1H, m), 3.45 (3H, s), 3.33 (3H, s), 1.86 (3H, s), 1.39 (3H, d, J=6.6 Hz), 1.13 (3H, d, J=6.9 Hz) $^{13}$C-NMR (67.8 MHz, CDCl$_3$) δ (ppm): 173.7, 165.3, 157.5, 149.3, 143.3, 139.6, 138.1, 138.0, 136.3, 135.1, 127.7, 124.7, 120.4, 118.3, 118.0, 116.5, 110.8, 110.6, 96.2, 95.8, 95.0, 81.9, 80.4, 80.3, 79.1, 78.9, 74.9, 70.2, 68.4, 68.3, 68.0, 67.7, 67.4, 57.9, 57.1, 56.5, 45.7, 40.5, 39.8, 36.6, 35.2, 34.8, 34.2, 33.3, 30.6, 27.5, 25.3, 20.1, 20.0, 19.3, 18.0, 16.4, 15.1, 13.0, 12.0

Example 37

Preparation of Compound 42

To 123 mg of 5-O-tert-butyldimethylsilylavermectin B2a, 0.2 ml of triethylamine, 0.6 ml of DMSO and 130 mg of sulfur trioxide/pyridine complex were added, and the mixture was stirred for 1 hour. To the reaction solution was added water and then the mixture was extracted with ethyl acetate. The organic layers were combined, washed with a saturated aqueous sodium hydrogencarbonate solution, and then dried over anhydrous sodium sulfate. The solvent was evaporated under reduced pressure to give a crude product. This crude product was purified by column chromatography on silica gel using an eluting solvent of hexane/ethyl acetate=2/1 to give 97 mg of Compound 42 in a 79% yield.

HR-FAB-MS: Calculated; $C_{54}H_{86}O_{15}Si$ [M+Na]$^+$ 1025.5634, Found; 1025.5641 IR(KBr) $\lambda_{max}$cm$^{-1}$: 3527, 2962, 2933, 1739, 1456, 1382, 1191, 1170, 1124, 1006, 987 $^1$H NMR (270 MHz, CDCl$_3$, partial data) δ (ppm): 5.74 (3H, m), 5.50 (1H, s), 5.28 (1H, s), 5.24 (1H, m), 4.95 (1H, m), 4.75 (1H, s), 4.65 (1H, d, J=14.5 Hz), 4.54 (1H, d, J=14.5 Hz), 4.17 (1H, dd, J=6.3, 11.6 Hz), 3.79 (1H, d, J=5.6 Hz), 3.48 (3H, s), 3.41 (3H, s), 1.76 (3H, s), 1.25 (3H, d, J=6.3 Hz), 0.90 (9H, s), 0.10 (6H, s) $^{13}$C NMR (67.8 MHz, CDCl$_3$) δ (ppm): 205.9, 173.9, 140.3, 137.6, 137.3, 135.6, 124.9, 119.3, 117.6, 117.1, 99.6, 98.0, 94.8, 81.8, 81.1, 80.2, 80.1, 79.1, 78.0, 77.7, 70.7, 69.9, 69.4, 68.2, 67.9, 67.6, 60.4, 58.3, 56.4, 45.7, 41.1, 40.7, 39.6, 39.4, 36.4, 35.7, 35.1, 34.5, 34.2, 27.2, 25.8(*3), 20.3, 20.0, 18.4, 18.3, 15.2, 14.2, 13.9, 12.4, 11.8, −4.6, −4.9

Example 38

Preparation of Compound 43

In 3.5 ml of isopropyl acetate, 1.12 g of 5-O-tert-butyldimethylsilylavermectin B2a was dissolved, and 0.65 ml of DMSO and 1.5 ml of triethylamine were added thereto at −30° C. under nitrogen gas atmosphere. To the resulting mixture, a solution of 0.6 ml of phenyl dichlorophosphate dissolved in 1.5 ml of isopropyl acetate was added slowly and dropwise. The mixture was stirred under nitrogen gas atmosphere below −20° C. for 1 hour and 30 minutes. Then, a 1% aqueous phosphoric acid solution was added thereto, and the mixture was extracted with ethyl acetate. The organic layers were combined, washed with a saturated aqueous sodium hydrogencarbonate solution, and then dried over anhydrous sodium sulfate. The solvent was evaporated under reduced pressure to give a crude product. The crude product was purified by column chromatography on silica gel with eluting solvents of hexane/ethyl acetate=4/1 to 2/1 to give 610 mg of Compound 43 in a 55% yield.

HR-FAB-MS: Calculated; $C_{54}H_{84}O_{15}Si$ [M+Na]$^+$ 1023.5477 Found; 1023.5507 IR(KBr) $\lambda_{max}$cm$^{-1}$: 3469, 2962, 2933, 1739, 1724, 1452, 1124, 1054, 1006, 989 $^1$H NMR (270 MHz, CDCl$_3$, partial data) δ (ppm): 5.76 (1H, m), 5.70 (2H, m), 5.48 (1H, s), 5.30 (1H, s), 5.26 (1H, m), 4.90 (1H, t, J=7.3 Hz), 4.73 (1H, d, J=3.3 Hz), 4.64 (1H, d, J=15.8 Hz), 4.53 (1H, d, J=16.1 Hz), 4.38 (2H, m), 4.15 (1H, m), 3.98 (1H, s), 3.89 (1H, br.s), 3.77 (1H, d, J=5.6 Hz), 3.46 (3H, s), 3.39 (3H, s), 3.28 (1H, t, J=8.9 Hz), 1.76 (3H, s), 1.11 (3H, d, J=6.9 Hz), 0.09 (6H, s) $^{13}$C NMR (67.8 MHz, CDCl$_3$) δ (ppm): 206.9, 205.8, 173.7, 140.1, 137.5, 137.3, 135.4, 124.8, 119.2, 117.6, 117.1, 100.5, 97.9, 94.7, 81.7, 81.0, 80.2, 80.0, 79.0, 77.9, 76.4, 70.6, 69.3, 68.1, 67.7, 67.6, 66.8, 60.3, 58.2, 56.3, 51.3, 46.3, 45.6, 40.3, 39.4, 39.3, 35.9, 35.8, 34.4, 33.7, 27.2, 25.7(*3), 20.2, 19.9, 18.3, 15.0, 13.8, 12.3, 11.5, 8.6, −4.7, −5.0

Example 39

Preparation of Compound 44

To 0.85 ml of a 1.0 mol/L tetrahydrofuran solution of lithium hexamethyldisilazane, 0.2 ml of methyl diethylphosphonoacetate was added, and the resulting mixture was stirred under ice-cooling (0° C.) for 30 minutes. Then, a solution of 400 mg of 5-O-tert-butyldimethylsilyl-23,4"-dioxoavarmectin B2a (Compound 43) dissolved in 1.5 ml of tetrahydrofuran was added to the mixture, and the mixture was stirred at room temperature for 3 hours. To the reaction solution was added a saturated aqueous ammonium chloride solution and the mixture was extracted with ethyl acetate. The ethyl acetate layer was dried over anhydrous sodium sulfate, and the solvent was evaporated under reduced pressure to give a crude product. The crude product was purified by column chromatography on silica gel using stepwise elution with eluting solvents of hexane/ethyl acetate=8/1~4/1~2/1~1/1 to give 325 mg of the desired compound in a 77% yield.

HR-FAB-MS: Calculated; $C_{57}H_{88}O_{16}Si$ $[M+Na]^+$ 1079.5738 Found; 1079.5693 IR(KBr) $\lambda_{max}cm^{-1}$: 3473, 2962, 2935, 1724, 1458, 1384, 1245, 1124, 1012, 987 $^1$H NMR (270 MHz, CDCl$_3$, partial data) δ (ppm): 5.81 (1H, s), 5.76 (1H, m), 5.69 (2H, m), 5.41 (1H, m), 5.30 (1H, s), 5.26 (1H, m), 5.10 (1H, br.s), 4.90 (1H, br.t, J=7.1 Hz), 4.71 (1H, d, J=3.0 Hz), 4.64 (1H, d, J=16.2 Hz), 4.53 (1H, d, J=16.2 Hz), 4.39 (1H, m), 3.95 (1H, s), 3.89 (1H, br.s), 3.78 (1H, d, J=6.6 Hz), 3.69 (3H, s), 3.41 (3H, s), 3.33 (3H, s), 1.66 (3H, s), 1.38 (3H, d, J=6.3 Hz), 1.09 (3H, d, J=6.9 Hz), 0.10 (6H, s) $^{13}$C NMR (67.8 MHz, CDCl$_3$) δ (ppm): 206.9, 173.7, 166.1, 156.7, 140.0, 137.5(*2), 135.5, 124.7, 119.3, 117.6, 117.1, 116.6, 100.5, 96.0, 94.8, 81.6, 80.2(*2), 80.1, 80.0, 78.8, 76.4, 70.1, 69.3, 68.1(*2), 67.8, 67.7, 67.3, 60.3, 57.0, 56.4, 51.3, 46.4, 45.6, 40.4, 39.5, 35.9, 35.8, 34.7, 33.7, 33.4, 27.1, 25.8(*3), 20.0, 19.3, 18.3, 17.8, 15.0, 12.3, 11.5, 8.7, −4.7, −5.0

Example 40

Preparation of Compound 45

In 2.5 ml of tetrahydrofuran, 208 mg of 5-O-tert-butyldimethylsilyl-23-oxo-4"-methoxycarbonylmethylideneavermectin B2a (Compound 44) obtained in Example 39 was dissolved, 1.5 ml of the solution A was added thereto, and the mixture was stirred at room temperature for a night. Pyridine was added thereto on an ice bath, an aqueous sodium hydrogencarbonate solution was further added for neutralization, and then the mixture was extracted with ethyl acetate. The ethyl acetate layer was dried over anhydrous magnesium sulfate, and the solvent was evaporated under reduced pressure to give a crude product. The crude product was purified by column chromatography on silica gel using stepwise elution with eluting solvents of hexane/2-propanol=85/15~4/1~3/1 to give 137 mg of the desired compound in a 73% yield.

HR-FAB-MS: Calculated; $C_{51}H_{74}O_{16}[M+Na]^+$ 965.4874 Found; 965.4835 IR(KBr) $\lambda_{max}cm^{-1}$: 3477, 2971, 2935, 1724, 1459, 1387, 1340, 1240, 1197, 1164, 1122, 1060, 1012, 987 $^1$H NMR (270 MHz, CDCl$_3$, partial data) δ (ppm): 5.83 (2H, s), 5.71 (2H, m), 5.43 (2H, s), 5.33 (1H, m), 5.13 (1H, m), 4.93 (1H, m), 4.74 (1H, d, J=3.0 Hz), 4.66 (2H, s), 4.49 (1H, q, J=6.6 Hz), 4.28 (1H, m), 3.71 (3H, s), 3.43 (3H, s), 3.35 (3H, s), 1.86 (3H, s), 1.40 (3H, d, J=6.6 Hz), 1.23 (3H, d, J=5.9 Hz), 1.13 (3H, d, J=6.9 Hz), $^{13}$C NMR (67.8 MHz, CDCl$_3$) δ (ppm): 207.0, 173.5, 166.2, 156.7, 139.5, 138.1, 135.5, 125.2, 124.6, 120.4, 117.9, 117.6, 116.6, 100.5, 96.1, 94.8, 81.6, 80.4(*2), 80.2, 79.1, 78.9, 70.1, 68.3, 68.2(*2), 67.6(*2), 67.4, 57.0, 56.5, 51.3, 46.5, 45.6, 40.4, 39.7, 36.0, 35.9, 34.8, 33.7, 33.4, 27.2, 20.1, 19.9, 19.4, 17.9, 15.1, 12.3, 11.6, 8.7

Example 41

Preparation of Compound 46

To 0.65 ml of a 1.0 mol/L tetrahydrofuran solution of lithium hexamethyldisilazane, 175 μl of allyl diethylphosphonoacetate was added, and the resulting mixture was stirred under ice-cooling (0° C.) for 1 hour. Then, a solution of 460 mg of 5-O-tert-butyldimethylsilyl-23,4"-dioxoavarmectin B2a (Compound 43) dissolved in 2.5 ml of tetrahydrofuran was added to the mixture, and then the mixture was stirred at room temperature for 5 hours. To the reaction solution was added a saturated aqueous ammonium chloride solution and the mixture was extracted with ethyl acetate. The ethyl acetate layer was dried over anhydrous sodium sulfate, and the solvent was evaporated under reduced pressure to give a crude product. The crude product was purified by column chromatography on silica gel using stepwise elution with eluting solvents of toluene/ethyl acetate=9/1~6/1~3/1 to give 390 mg of the desired compound in a 78% yield.

HR-FAB-MS: Calculated; $C_{59}H_{90}O_{16}Si$ $[M+Na]^+$ 1105.5898 Found; 1105.5885 IR(KBr) $\lambda_{max}cm^{-1}$: 3457, 2962, 2933, 1724, 1456, 1386, 1195, 1124, 1087, 1010, 987 $^1$H NMR (270 MHz, CDCl$_3$, partial data) δ (ppm): 5.92 (1H, m), 5.86 (1H, s), 5.70 (2H, m), 5.42 (1H, m), 5.30 (5H, m), 5.12 (1H, br.s), 4.92 (1H, m), 4.73 (1H, d, J=3.3 Hz), 3.96 (1H, s), 3.90 (1H, br.s), 3.43 (3H, s), 3.34 (3H, s), 1.78 (3H, s), 1.40 (3H, d, J=6.6 Hz), 1.22 (3H, d, J=6.9 Hz), 1.11 (3H, d, J=6.9 Hz), 0.91 (9H, s), 0.12 (6H, s) $^{13}$C NMR (67.8 MHz, CDCl$_3$) δ (ppm): 207.0, 173.8, 165.3, 157.1, 140.1, 137.6, 135.5, 132.0, 124.7, 119.3, 118.45, 117.6, 117.1, 116.7, 100.5, 96.1, 94.8, 81.6, 80.23, 80.18, 80.0, 78.8, 76.3, 70.1, 69.4, 68.14, 68.05, 67.8, 67.7, 67.4, 65.0, 57.0, 56.5, 51.4, 46.5, 45.7, 40.4, 39.6, 36.0, 35.9, 34.8, 33.7, 33.4, 27.2, 25.8(*3), 25.7, 20.2, 20.0, 19.3, 18.4, 17.9, 15.1, 12.3, 11.6, 8.7, −4.7, −4.9

Example 42

Preparation of Compound 47

In 2.0 ml of tetrahydrofuran, 37 mg of 5-O-tert-butyldimethylsilyl-4"-carboxymethylideneavermectin B2a (Compound 51) was dissolved, 0.3 ml of the solution A was added thereto, and the mixture was stirred at room temperature for 1 day. The mixture was subjected to post-treatment in a manner similar to that in Example 40, and then the resulting crude product was purified by column chromatography on silica gel with eluting solvents of dichloromethane/methanol=9/1 to 6/1 to give 27 mg of the desired compound in a 84% yield.

IR(KBr) $\lambda_{max}cm^{-1}$: 3457, 2966, 2933, 1718, 1656, 1454, 1382, 1122, 1008, 989 $^1$H NMR (270 MHz, CDCl$_3$, partial data) δ (ppm): 5.86 (1H, s), 5.44 (3H, m), 5.30 (1H, m), 5.06 (1H, s), 4.96 (1H, m), 4.75 (1H, d, J=2.3 Hz), 4.66 (2H, s), 4.49 (1H, q, J=6.0 Hz), 4.29 (1H, d, J=5.5 Hz), 3.44 (3H, s), 3.37 (3H, s), 1.85 (3H, s), 1.41 (3H, d, J=6.3 Hz), 1.24 (3H, d, J=5.9 Hz), 1.14 (3H, d, J=6.6 Hz) $^{13}$C NMR (67.8 MHz, CDCl$_3$) δ (ppm): 173.6, 168.9, 157.6, 139.5, 138.0, 137.9, 135.9, 124.7, 120.4, 117.9, 117.4, 116.8, 99.6, 96.2, 94.9, 81.6, 80.3, 80.1, 79.1, 78.9, 77.7, 70.8, 70.7, 69.9, 68.4, 68.2, 68.1, 67.6, 67.4, 57.0, 56.5, 45.7, 41.1, 40.7, 39.7, 36.4, 35.6, 35.1, 34.7, 34.1, 33.5, 27.2, 20.1, 19.9, 19.1, 17.9, 15.1, 13.7, 12.4, 11.8

Example 43

Preparation of Compound 48

To 135 μl of a 1.0 mol/L tetrahydrofuran solution of lithium hexamethyldisilazane, 30 μl of diethylphosphonocyanomethyl was added, and the resulting mixture was stirred under ice-cooling (0° C.) for 30 minutes. Then, a solution of 124 mg of 5-O-tert-butyldimethylsilyl-4"-oxoavarmectin B2a (Compound 42) dissolved in 0.4 ml of tetrahydrofuran was added to the mixture, and the mixture was stirred at room temperature for 3 hours. To the reaction solution was added a saturated aqueous ammonium chloride solution and the mixture was extracted with ethyl acetate. The ethyl acetate layer was dried over anhydrous sodium sulfate, and the solvent was evaporated under reduced pressure to give a crude product. The crude product was dissolved in 1.2 ml or tetrahydrofuran, 0.5 ml of the solution A was added thereto, and the mixture was stirred at room temperature for a night. The mixture was subjected to post-treatment in a manner similar to that in Example 40, and the resulting crude product was purified by column chromatography on silica gel with eluting solvents of toluene/ethyl acetate=4/1~3/1~2/1~1/1 to give 43 mg of the desired compound in a 37% yield.

HR-FAB-MS: Calculated; $C_{50}H_{73}NO_{14}$ [M+Na]$^+$ 934.4929 Found; 934.4921 IR(KBr) $\lambda_{max}$cm$^{-1}$: 3515, 2967, 2933, 2221, 1733, 1456, 1382, 1191, 1120, 1054 $^1$H NMR (270 MHz, CDCl$_3$, partial data) δ (ppm): 5.92 (1H, m), 5.80 (2H, m), 5.50 (2H, m), 5.41 (1H, s), 5.37 (1H, m), 5.03 (1H, m), 4.82 (1H, d, J=3.0 Hz), 4.73 (2H, s), 4.68 (1H, m), 4.53 (2H, m), 3.53 (3H, s), 3.49 (3H, s), 1.93 (3H, s), 1.42 (3H, d, J=6.6 Hz), 1.30 (3H, d, J=6.3 Hz), 1.21 (3H, d, J=6.9 Hz)

Example 44

Preparation of Compound 49

To 0.85 ml of a 1.0 mol/L tetrahydrofuran solution of lithium hexamethyldisilazane, 25 μl of diethylphosphonocyanomethyl was added, and the resulting mixture was stirred under ice-cooling (0° C.) for 30 minutes. Then, a solution of 105 mg of 5-O-tert-butyldimethylsilyl-4"-oxoavermectin B2a (Compound 42) in 0.3 ml of tetrahydrofuran was added to the mixture, and the mixture was stirred at room temperature for 4 hours. To the reaction solution was added a saturated aqueous ammonium chloride solution and the mixture was extracted with ethyl acetate. The ethyl acetate layer was dried over anhydrous sodium sulfate, and the solvent was evaporated under reduced pressure. The residue was purified by column chromatography on silica gel using stepwise elution with eluting solvents of hexane/ethyl acetate=6/1 to 4/1. The main product was dissolved in 0.15 ml of pyridine, 12 mg of dimethylaminopyridine and 0.08 ml of acetic anhydride were added thereto, and the mixture was stirred at room temperature for a night. A saturated aqueous sodium hydrogencarbonate solution was added thereto, and then the mixture was extracted with dichloromethane The organic layer was dried over anhydrous sodium sulfate, and the solvent was evaporated under reduced pressure to give a crude product. The crude product was further dissolved in 1.5 ml of tetrahydrofuran, 0.4 ml of the solution A was added thereto, and the mixture was stirred at room temperature for a night. The mixture was subjected to post-treatment in a manner similar to that in Example 40, and the resulting crude product was purified by column chromatography on silica gel with an eluting solvent of hexane/2-propanol=85/15 to give 49 mg of the desired compound in a 51% yield.

HR-FAB-MS: Calculated; $C_{52}H_{75}NO_{15}$ [M+Na]$^+$ 976.5034 Found; 976.5025 $^1$H NMR (270 MHz, CDCl$_3$, partial data) δ (ppm): 5.85 (1H, m), 5.72 (2H, m), 5.41 (3H, m), 5.32 (1H, m), 4.99 (1H, br.d, J=7.0 Hz), 4.86 (1H, d, J=2.6 Hz), 4.76 (1H, d, J=3.0 Hz), 4.67 (2H, s), 3.95 (1H, d, J=6.3 Hz), 3.47 (3H, s), 3.44 (3H, s), 2.02 (3H, s), 1.86 (3H, s), 1.35 (3H, d, J=6.6 Hz), 1.24 (3H, d, J=6.2 Hz), 1.15 (3H, d, J=6.6 Hz) $^{13}$C NMR (67.8 MHz, CDCl$_3$) δ (ppm): 173.8, 163.4, 139.7, 138.0, 137.8, 135.1, 124.8, 120.3, 118.2, 118.0, 116.1, 97.4, 97.1, 94.9, 94.1, 81.9, 80.7, 80.4, 79.0, 75.4, 71.7, 70.5, 68.4, 68.2, 67.7, 67.4, 66.7, 57.8, 56.8, 45.7, 41.0, 39.7, 38.5, 36.9, 36.5, 35.2, 34.6, 34.1, 27.3, 21.3, 20.2, 19.9, 18.2, 17.7, 15.1, 13.2, 12.4, 11.6

Example 45

Preparation of Compound 50

To 1.6 ml of a 1.0 mol/L tetrahydrofuran solution of lithium hexamethyldisilazane, 415 μl of allyl diethylphosphonoacetate was added, and the resulting mixture was stirred under ice-cooling (0° C.) for 30 minutes. Then, a solution of 1.06 g of 5-O-tert-butyldimethylsilyl-4"-oxoavermectin B2a (Compound 42) dissolved in 2 ml of tetrahydrofuran was added to the mixture, and the mixture was stirred at room temperature for 4 hours. To the reaction solution was added a saturated aqueous ammonium chloride solution and the mixture was extracted with ethyl acetate. The ethyl acetate layer was dried over anhydrous sodium sulfate, and the solvent was evaporated under reduced pressure to give a crude product. The crude product was purified by column chromatography on silica gel using stepwise elution with eluting solvents of hexane/ethyl acetate=12/1~8/1~4/1 to give 671 mg of the desired compound in a 59% yield.

$^1$H NMR (270 MHz, CDCl$_3$, partial data) δ (ppm): 5.94 (1H, m), 5.85 (1H, s), 5.49–5.10 (5H, m), 5.12 (1H, br.s), 4.95 (1H, m), 3.91(1H, s), 3.80(1H, d, J=5.3 Hz), 3.42 (3H, s), 3.34 (3H, s), 1.76 (1H, s), 1.48 (1H, s), 1.40 (3H, d, J=6.3 Hz), 1.11 (3H, d, J=6.9 Hz), 0.90 (9H, s), 0.11(6H, s) $^{13}$C NMR (67.8 MHz, CDCl$_3$) δ (ppm): 173.8, 165.3, 157.0, 140.1, 137.5(*2), 135.6, 132.0, 124.7, 119.3, 118.4, 117.4, 117.1, 116.6, 99.6, 96.1, 94.9, 81.6, 80.2(*2), 80.0, 78.8, 70.7, 70.0, 69.8, 69.4, 68.2, 68.1, 67.8, 67.6, 67.4, 64.9, 60.3, 57.0, 56.4, 45.6, 41.1, 40.6, 39.6, 36.3, 35.6, 35.0, 34.7, 34.1, 33.3, 27.2, 25.8(*3), 20.2, 19.3, 18.3, 17.9, 15.1, 13.7, 12.4, 11.7, −4.7, −4.9

Example 46

Preparation of Compound 51

In 2.0 ml of ethanol, 671 mg of 5-O-tert-butyldimethylsilyl-4"-allyloxycarbonylmethylideneavermectin B2a (Compound 50) was dissolved, 12 mg of tetrakis(triphenylphosphine)palladium(O) and 92 mg of sodium borohydride were added thereto, and then the mixture was stirred at 0° C. to room temperature for 1 hour. Saturated brine was added thereto, and then the mixture was extracted with ethyl acetate. The organic layer was washed with water and dried over anhydrous magnesium sulfate. The solvent was evaporated under reduced pressure to give a crude product. The crude product was purified by column chromatography on silica gel using stepwise elution with eluting solvents of dichloromethane/ethyl acetate=2/1~1/1~1/2~0/1 to give 600 mg of the desired compound in a 92% yield.

$^1$H NMR (270 MHz, CDCl$_3$, partial data) δ (ppm): 5.87 (1H, s), 5.78 (1H, m), 5.71 (2H, m), 5.44 (1H, m), 5.31 (1H, s), 5.26 (1H, m), 5.05 (1H, br.s), 4.96 (1H, m), 4.74 (1H, br.s), 4.67 (1H, d, J=15.5 Hz), 4.57 (1H, d, J=15.5 Hz), 4.49 (1H, d, J=5.6 Hz), 4.42 (1H, br.s), 3.93 (1H, s), 3.81 (1H, d, J=5.6 Hz), 3.43 (3H, s), 3.38 (3H, s), 1.78 (3H, s), 1.41 (3H, d, J=6.3 Hz), 1.12 (3H, d, J=6.6 Hz), 0.91 (9H, s), 0.12 (6H, s)

Example 47

Preparation of Compound 52

In 0.15 ml of pyridine, 333 mg of 5-O-tert-butyldimethylsilyl-4"-carboxymethylideneavermectin B2a (Compound 51) was dissolved, 12 mg of dimethylaminopyridine and 0.08 ml of acetic anhydride were added thereto, and then the mixture was stirred at room temperature for a night. A saturated aqueous sodium hydrogencarbonate solution was added thereto, and then mixture was extracted with dichloromethane. The organic layer was dried over anhydrous sodium sulfate. The solvent was evaporated under reduced pressure to give a crude product. The crude product was dissolved in 2.1 ml of tetrahydrofuran, 0.7 ml of the solution A was added thereto, and the mixture was stirred at room temperature for a night. The mixture was subjected to post-treatment in a manner similar to that in Example 40, and the resulting crude product was purified by thin-layer chromatography on silica gel of 0.5 mm thickness using a developing solvent of dichloromethane/methanol=10/1 to give 19 mg of the desired compound in a 6% yield.

HR-FAB-MS: Calculated; $C_{52}H_{76}O_{17}$ [M—H+2Na]$^+$ 1017.4800 Found; 1017.4872 IR(KBr) $\lambda_{max}cm^{-1}$: 3450, 2967, 2933, 1731, 1718, 1378, 1251, 1187, 1122, 1008, 991 $^1$H NMR (270 MHz, CDCl$_3$, partial data) δ (ppm): 5.85 (1H, m), 5.71 (2H, m), 5.56 (1H, d, J=6.6 Hz), 5.47 (1H, m), 5.41 (1H, s), 5.31 (1H, m), 4.98 (1H, br.d, J=3.3 Hz), 4.86 (1H, d, J=2.3 Hz), 4.76 (1H, d, J=3.3 Hz), 4.67 (1H, s), 4.29 (1H, d, J=5.9 Hz), 3.96 (1H, d, J=7.3 Hz), 3.46 (3H, s), 3.24 (3H, s), 2.03 (3H, s), 1.86(3H, s), 1.13 (3H, d, J=6.9 Hz), 0.97 (3H, t, J=6.9 Hz) $^{13}$C NMR (67.8 MHz, CDCl$_3$) δ (ppm): 173.7, 171.3, 168.9, 156.8, 139.5, 138.0, 137.9, 135.2, 124.7,120.4, 118.1, 118.0, 117.8, 97.4, 94.9, 94.1, 81.8, 80.8, 80.5, 80.4, 79.1, 78.9, 71.7, 70.5, 68.5, 68.3, 67.7, 67.5, 57.1, 56.1, 45.7, 41.0, 39.8, 38.5, 38.2, 36.4, 35.2, 34.8, 34.1, 27.3, 21.3, 20.1, 19.9, 19.6, 18.0, 15.0, 13.2, 12.4, 11.6 (three peaks were overlapped with other peaks.)

Example 48

Preparation of Compound 53

In 0.9 ml of dichloromethane, 45.4 mg of Compound 26 was dissolved, 39.0 mg of manganese dioxide was added thereto, and the mixture was stirred at room temperature for 3.5 hours. The mixture was diluted with dichloromethane and then passed through a celite column, and the column was further washed with dichloromethane. The resulting dichloromethane solution was concentrated under reduced pressure to give 45.4 mg of the desired compound in a 100% yield.

HR-FAB-MS: Calculated; $C_{56}H_{75}O_{15}N$ [M+Na]$^+$ 1024.5044 Found; 1024.5026 IR(KBr) $\lambda_{max}cm^{-1}$: 3450, 2969, 2879, 1734, 1682, 1456, 1378,1279,1120,1045, 987 $^1$H NMR (270 MHz, CDCl$_3$, partial data) δ (ppm): 8.78 (2H, br.s), 7.86 (2H, br.s), 6.58 (1H, s), 5.94 (1H, m), 5.71 (4H, m), 5.55 (1H, dd, J=2.6, 9.9 Hz), 5.44 (2H, m), 5.14 (1H, dd, J=7.2, 13.2 Hz), 4.98 (3H, m), 4.75 (3H, m), 4.43 (1H, d, J=6.3 Hz), 3.46 (3H, s), 3.38 (3H, s), 1.88 (3H, s), 1.49 (3H, s), 1.37 (3H, d, J=6.3 Hz), 1.26 (3H, d, J=6.3 Hz), 1.15 (3H, d, J=6.9 Hz) $^{13}$C NMR (67.8 MHz, CDCl$_3$) δ (ppm): 192.1, 172.1, 165.0, 150.5 (*2), 143.0, 139.1, 138.1, 137.9, 137.4, 136.7, 136.4, 135.3, 127.7, 124.7, 122.9 (*2), 121.9, 120.2, 118.3, 96.8, 95.8, 95.0, 82.0, 81.8, 81.3, 80.3, 79.0, 74.9, 73.4, 69.8, 69.1, 68.4, 67.5, 67.4, 62.1, 56.9, 55.9, 46.6, 40.5, 39.9, 36.5, 35.2, 34.8, 34.2 (*2), 30.6, 27.5, 20.1, 18.4, 18.1, 16.4, 15.5, 15.1,13.0, 12.1

Example 49

Preparation of Compound 54

In 0.9 ml of dichloromethane, 41.4 mg of Compound 23 was dissolved, 120 mg of manganese dioxide was added thereto, and the mixture was stirred at room temperature for 1 hour. The mixture was diluted with dichloromethane and then passed through a celite column, and the column was further washed with dichloromethane. The resulting dichloromethane solution was concentrated under reduced pressure to give 39.6 mg of the desired compound in a 96% yield.

HR-FAB-MS: Calculated; $C_{50}H_{69}O_{13}N$ [M+Na]$^+$ 914.4667 Found; 914.4677 IR(KBr) $\lambda_{max}cm^{-1}$: 3452, 2966, 2931,2222, 1738, 1682, 1456, 1381, 1187, 1118, 1045, $^1$H NMR (270 MHz, CDCl$_3$, partial data) δ (ppm): 6.57 (1H, s), 5.93 (1H, m), 5.75 (3H, m), 5.57 (1H, dd, J=2.1, 10.1 Hz), 5.43 (3H, m), 4.98 (1H, m), 4.76 (3H, m), 4.47 (1H, d, J=6.2 Hz), 4.31 (1H, m), 3.48 (3H, s), 3.45 (3H, s), 1.89 (3H, s), 1.49 (3H, s), 1.36 (3H, d, J=6.6 Hz), 1.23 (3H, d, J=6.3 Hz), 1.15 (3H, d, J=6.9 Hz) $^{13}$C NMR (67.8 MHz, CDCl$_3$) δ (ppm): 192.1, 172.2, 163.3, 138.9, 137.9, 137.8, 136.8, 136.4, 135.1, 127.6, 124.7, 121.7, 118.2, 116.0, 97.1, 95.7, 94.9, 94.0, 81.9, 81.8, 80.7 (*2), 79.0, 75.4, 74.9, 69.8, 69.0, 68.3, 67.1, 66.7, 57.8, 56.7, 46.5, 40.4, 39.8, 36.9, 36.5, 35.1, 34.5, 34.1, 30.5, 27.5, 20.0, 18.1, 17.6, 16.3, 15.4, 15.1,12.9, 12.1

Example 50

Preparation of Compound 55

To a solution of 36.4 mg of Compound 53 in 120 μl of ethanol, 8.0 mg of hydroxylamine hydrochloride and 180 μl of pyridine were added, and the mixture was stirred at room temperature for 1 hour. An aqueous sodium hydrogencarbonate solution was added thereto, and then the mixture was extracted with ethyl acetate. The ethyl acetate layer was dried over anhydrous magnesium sulfate, and the solvent was evaporated under reduced pressure to give a crude product. The crude product was purified by column chromatography on silica gel using stepwise elution with eluting solvents of hexane/2-propanol=50/1~40/1~30/1~10/1 to give 31.0 mg of the desired compound in a 83% yield.

HR-FAB-MS: Calculated; $C_{56}H_{75}O_{15}N$ [M+Na]$^+$ 1039.5143 Found; 1039.5203 IR(KBr) $\lambda_{max}cm^{-1}$: 3375, 2968, 2933, 1732, 1456, 1379, 1329, 1279, 1120, 1041, 989 $^1$H NMR (270 MHz, CDCl$_3$, partial data) δ (ppm): 8.77 (2H, br.s), 7.87 (2H, br.s), 5.91 (1H, m), 5.69 (4H, m), 5.55 (1H, dd, J=2.5, 9.7 Hz), 5.40 (2H, m), 5.14 (1H, dd, J=7.6, 13.2 Hz), 5.02(1H, dd, J=5.6, 13.2 Hz), 4.93 (1H, dd, J=6.3, 13.2 Hz), 4.75 (1H, d, J=4.3 Hz), 4.64 (2H, m), 4.43 (1H, d, J=6.3 Hz), 3.46(3H, s), 3.38 (3H, s), 1.98 (3H, s), 1.48 (3H, s), 1.36 (3H, d, J=6.6 Hz), 1.26 (3H, d, J=6.3 Hz), 1.15 (3H, d, J=6.9 Hz) $^{13}$C NMR (67.8 MHz, CDCl$_3$) δ (ppm): 173.1, 164.7, 151.2, 150.4 (*2), 143.0, 138.4, 138.2, 137.5, 136.5, 135.1, 132.2, 127.7, 124.8, 122.9 (*2), 121.3, 120.1, 118.2, 118.0, 96.9, 95.7, 95.0, 82.0, 80.3, 80.1, 79.0, 78.6, 74.8, 73.3, 68.7, 68.4, 68.2, 67.3, 64.4, 62.1, 57.0, 56.0, 46.4, 40.4, 39.9, 36.5, 35.1, 34.7, 34.4, 34.1, 30.6, 27.4, 20.1, 18.3, 18.0, 17.5, 16.3, 15.1,12.9, 12.0

Example 51

Preparation of Compound 56

To a solution of 94.6 mg of Compound 54 in 350 μl of ethanol, 14.7 mg of hydroxylamine hydrochloride and 550 μl of pyridine were added, and the mixture was stirred at room temperature for a night. An aqueous sodium hydrogencarbonate solution was added thereto, and then the mixture was extracted with ethyl acetate. The ethyl acetate layer was dried over anhydrous magnesium sulfate, and the solvent was evaporated under reduced pressure to give a crude product. The crude product was purified by column chromatography on silica gel using stepwise elution with eluting solvents of hexane/ethyl acetate=4/1~2/1~1/1 to give 64.0 mg of the desired compound in a 66% yield.

HR-FAB-MS: Calculated; $C_{50}H_{70}O_{13}N_2Na$ [M+Na]$^+$ 929.4776 Found; 929.4778 IR(KBr) $\lambda_{max}cm^{-1}$: 3462, 2968, 2933, 2224, 1714, 1456, 1381, 1340, 1160, 1119, 1043, 989 $^1$H NMR (270 MHz, CDCl$_3$, partial data) δ (ppm): 8.77 (2H, br.s), 7.87 (2H, br.s), 5.91 (1H, m), 5.69 (4H, m), 5.55 (1H, dd, J=2.5, 9.7 Hz), 5.40 (2H, m), 5.14 (1H, dd, J=7.6, 13.2 Hz), 5.02 (1H, dd, J=5.6, 13.2 Hz), 4.93 (1H, dd, J=6.3, 13.2 Hz), 4.75 (1H, d, J=4.3 Hz), 4.64 (2H, m), 4.43 (1H, d, J=6.3 Hz), 3.46 (3H, s), 3.38 (3H, s), 1.98 (3H, s), 1.48 (3H, s), 1.36 (3H, d, J=6.6 Hz), 1.26 (3H, d, J=6.3 Hz), 1.15 (3H, d, J=6.9 Hz) $^{13}$C NMR (67.8 MHz, CDCl$_3$) δ (ppm): 173.6, 164.8, 151.6, 138.6 (*2), 136.7, 135.5, 132.5, 128.1, 125.6, 125.3, 121.8, 118.7, 116.4, 97.6, 96.1, 95.4, 94.4, 82.4, 81.2, 79.4, 79.1, 78.3, 75.9, 75.3, 73.4, 69.2, 68.9, 67.5, 67.1, 58.2, 57.0, 46.8, 40.9, 40.3, 37.3, 36.9, 35.5, 35.0, 34.6, 31.0, 27.9, 20.6, 18.5, 18.0, 16.7, 15.7, 15.5, 13.4, 12.4

Example 52

Preparation of Compound 57

In 1.2 ml of dichloromethane, 107 mg of Compound 25 was dissolved, 510 mg of manganese dioxide was added thereto, and the mixture was stirred at room temperature for a night. The mixture was diluted with dichloromethane and then passed through a celite column, and the column was further washed with dichloromethane. The resulting dichloromethane solution was concentrated under reduced pressure to give 68.0 mg of the desired compound in a 64% yield.

HR-FAB-MS: Calculated; C$_{50}$H$_{70}$O$_{15}$ [M+2Na—H]$^+$ 955.4432 Found; 955.4415 IR(KBr) $\lambda_{max}$cm$^{-1}$: 3425, 2964, 2931, 1722, 1657, 1458, 1380, 1259, 1161, 1117, 1065, 1041, 1005 $^1$H NMR (270 MHz, CDCl$_3$, partial data) δ (ppm): 6.57 (1H, s), 5.83 (5H, m), 5.55 (1H, dd, J=2.0, 9.9 Hz), 5.44 (2H, m), 5.06 (1H, br.s), 4.99 (1H, m), 4.76 (1H, m), 4.73 (2H, s), 4.50 (1H, d, J=6.3 Hz), 3.45 (3H, s), 3.38 (3H, s), 1.87 (3H, s), 1.48 (3H, s), 1.41 (3H, d, J=6.6 Hz), 1.13 (3H, d, J=6.9 Hz) $^{13}$C NMR (67.8 MHz, CDCl$_3$) δ (ppm): 192.1, 172.2, 169.5, 158.0, 139.1, 138.0, 137.7, 136.8, 136.4, 135.2, 127.6, 124.6, 121.8, 118.2, 116.8, 96.2, 95.7, 95.0, 81.9, 81.7, 80.8, 80.2, 78.9, 74.9, 70.7, 69.8, 69.1, 68.3, 68.0, 67.4, 57.0, 56.5, 46.6, 40.5, 39.8, 36.5, 35.1, 34.7, 34.1, 33.5, 30.6, 27.5, 20.0, 19.1, 18.0, 16.3, 15.5, 15.1,13.0, 12.0

Example 53

Preparation of Compound 58

To a solution of 43.0 mg of Compound 57 in 150 μl of ethanol, 7.0 mg of hydroxylamine hydrochloride and 100 μl of pyridine were added, and the mixture was stirred at room temperature for 5 hours. An aqueous sodium hydrogencarbonate solution was added thereto, and then the mixture was extracted with ethyl acetate. The ethyl acetate layer was dried over anhydrous magnesium sulfate, and the solvent was evaporated under reduced pressure to give a crude product. The crude product was purified by column chromatography on silica gel using stepwise elution with eluting solvents of dichloromethane/methanol=30/1~20/1~10/1 to give 24.1 mg of the desired compound in a 56% yield.

HR-FAB-MS: Calculated; C$_{50}$H$_{71}$O$_{15}$N [M+2Na—H]$^+$ 970.4541 Found; 970.4550 IR(KBr) $\lambda_{max}$cm$^{-1}$: 3425, 2991, 2964, 1726, 1657, 1458, 1381, 1259, 1161, 1117, 1064, 1041, 1005 $^1$H NMR (270 MHz, CDCl$_3$, partial data) δ (ppm): 5.79 (5H, m), 5.52 (1H, dd, J=2.1, 9.9 Hz), 5.43 (2H, m), 5.06 (1H, br.s), 4.96 (1H, m), 4.75 (1H, br.s), 4.70 (2H, m), 4.51 (1H, d, J=6.3 Hz), 3.45 (3H, s), 3.38 (3H, s), 1.92 (3H, s), 1.48 (3H, s), 1.41 (3H, d, J=6.6 Hz), 1.14 (3H, d, J=6.6 Hz) $^{13}$C NMR (67.8 MHz, CDCl$_3$) δ (ppm): 173.1, 169.4, 158.0, 151.2, 138.4, 137.9, 136.3, 135.1, 131.7, 127.7, 126.0, 124.8, 121.5, 118.2, 116.7, 96.3, 95.7, 95.0, 81.9, 80.3, 78.9 (*2), 78.7, 74.9, 73.1, 70.7, 68.6, 68.4, 68.0, 67.4, 57.0, 56.6, 46.4, 40.5, 39.9, 36.5, 35.1, 34.7, 33.5, 30.6, 29.7, 27.5, 20.1, 19.2, 18.0, 17.5, 16.4, 15.1,13.0, 12.0

Example 54

Preparation of Compounds 59 and 60

To 740 μl of a 1.0 mol/L tetrahydrofuran solution of lithium hexamethyldisilazane, 130 μl of diethyl-1-cyanoethyl phophonate was added, and the resulting mixture was stirred under ice-cooling at 0° C. for 30 minutes. Then, a solution of 100 mg of 5-O-tert-butyldimethylsilyl-4"-oxoavermectin B1a dissolved in 1.0 ml of tetrahydrofuran was added to the mixture, and the mixture was stirred at room temperature for a night. The reaction mixture was then treated and purified in the manners similar to those in Example 1 to give 393 mg of the desired compound in a 87% yield.

Compounds 59 and 60, which are isomers based on the 4"-exomethylene moiety, were found to have the Rf values of 0.48 and 0.59, respectively, on thin-layer chromatography with a developing solvent of hexane/ethyl acetate=2/1.

Compound 59:

HR-FAB-MS: Calculated; C$_{57}$H$_{87}$O$_{13}$NSi [M+Na]$^+$ 1044.5844 Found; 1044.5818 IR(KBr) $\lambda_{max}$cm$^{-1}$: 3435, 2962, 2934, 2403, 1736, 1716, 1624, 1456, 1379, 1161, 1120, 1086 $^1$H NMR (270 MHz, CDCl$_3$, partial data) δ (ppm): 5.73 (4H, m), 5.54 (1H, dd, J=2.3, 9.9 Hz), 5.44 (1H, dd, J=4.0, 6.9 Hz), 5.34 (2H, m), 4.98 (1H, m), 4.83 (1H, dd, J=6.9, 13.9 Hz), 4.77 (1H, d, J=3.0 Hz), 4.68 (1H, d, J=16.8 Hz), 4.57 (1H, d, J=16.8 Hz), 4.50 (1H, t, J=3.3 Hz), 4.42 (1H, m), 3.46 (3H, s), 3.33 (3H, s), 1.95 (3H, s), 1.79 (3H, s), 1.49 (3H, s), 1.43 (3H, d, J=6.9 Hz), 1.23 (3H, d, J=6.6 Hz), 1.13 (3H, d, J=6.9 Hz), 0.93 (9H, s), 0.13 (6H, s) $^{13}$C NMR (67.8 MHz, CDCl$_3$) δ (ppm) 174.0, 152.5, 140.1, 137.5 (*2), 136.2, 135.1, 127.7, 124.7, 119.3, 118.2 (*2), 117.1, 107.2, 95.7, 94.9, 94.2, 82.0, 81.0, 80.2, 80.0, 78.8, 76.5, 74.8, 69.4, 68.4, 68.3, 68.0, 67.9, 67.2, 57.0, 56.3, 45.7, 40.4, 39.6, 37.3, 36.5, 35.1, 34.7, 34.2, 30.5, 27.5, 25.8 (*3), 20.2, 20.0, 19.2, 18.4, 18.0, 16.3, 16.0, 15.1,12.9, 12.0, -4.6, -4.9

Compound 60:

HR-FAB-MS: Calculated; C$_{57}$H$_{87}$O$_{13}$NSi [M+Na]$^+$ 1044.5844 Found; 1044.5859 IR(KBr) $\lambda_{max}$cm$^{-1}$: 3445, 2964, 2931, 2372, 1736, 1716, 1624, 1454, 1381, 1160, 1122, 1086 $^1$H NMR (270 MHz, CDCl$_3$, partial data) δ (ppm): 5.74 (4H, m), 5.55 (1H, dd, J=2.5, 9.9 Hz), 5.47 (1H, dd, J=3.5, 6.7 Hz), 5.35 (2H, m), 5.02 (2H, m), 4.76 (1H, d, J=3.0 Hz), 4.68 (1H, d, J=15.8 Hz), 4.57 (1H, d, J=15.8 Hz), 4.42 (1H, t, J=3.3 Hz), 4.42 (1H, m), 3.46 (3H, s), 3.28 (3H, s), 2.02 (3H, s), 1.79 (3H, s), 1.62 (3H, s), 1.52 (3H, d, J=6.9 Hz), 1.24 (3H, d, J=5.9 Hz), 1.13 (3H, d, J=6.6 Hz), 0.93 (9H, s), 0.13 (6H, s) $^{13}$C NMR (67.8 MHz, CDCl$_3$) δ (ppm): 174.0, 152.8, 140.1, 137.6 (*2), 136.2, 135.2, 127.8, 124.8, 119.3, 118.3 (*2), 117.2, 106.9, 95.8, 95.0, 94.3, 82.0, 80.8, 80.2, 80.1, 78.9, 74.9, 71.6, 71.5, 69.5, 68.4, 68.3, 67.9, 67.3, 56.9, 56.1, 45.8, 40.4, 39.6, 36.6, 36.3, 35.2, 34.7, 34.3, 30.6, 27.5, 25.9 (*3), 20.4, 20.2, 20.0, 18.4, 18.0, 16.5, 16.0, 15.1,12.9, 12.0, -4.6, -4.9

Example 55

Preparation of Compound 61

In 80 μl of tert-butanol, 39.2 mg of Compound 24 was dissolved, 2.0 mg of 4-dimethylaminopyridine and 15 μl of di-tert-butyl dicarbonate were added thereto, and the mixture was stirred for 2 hours. After the reaction was completed, the reaction solution was concentrated under reduced pressure to give a desired crude product. The crude product was purified by column chromatography on silica gel using stepwise elution with eluting solvents of hexane/ethyl acetate=30/1~20/1~10/1 to give 41.5 mg of the desired compound in a 73% yield.

HR-FAB-MS: Calculated; $C_{60}H_{94}O_{15}Si$ [M+Na]$^+$ 1105.6260 Found; 1105.6260 IR(KBr) $\lambda_{max}cm^{-1}$: 3449, 2968, 2931, 2372, 1714, 1658, 1450, 1383, 1254, 1160, 1124, 1082, 1006 $^1$H NMR (270 MHz, CDCl$_3$, partial data) δ (ppm): 5.74 (5H, m), 5.54 (1H, dd, J=2.3, 9.9 Hz), 5.38 (2H, m), 5.14 (1H, m), 4.99 (1H, m), 4.76 (1H, d, J=3.3 Hz), 4.68 (1H, d, J=16.2 Hz), 4.57 (1H, d, J=16.2 Hz), 4.47 (2H, m), 3.45 (3H, s), 3.36 (3H, s), 1.79 (3H, s), 1.61 (3H, s), 1.41 (3H, d, J=6.6 Hz), 1.24 (3H, d, J=6.3 Hz), 1.13 (3H, d, J=6.9 Hz), 0.93 (9H, s), 0.91 (9H, s), 0.13 (6H, s) $^{13}$C NMR (67.8 MHz, CDCl$_3$) δ (ppm): 174.0, 165.2, 154.3, 140.1, 137.5, 136.2, 135.1, 128.3, 127.7, 124.7, 119.3, 118.9, 118.2, 117.2, 96.1, 95.7, 95.0, 81.9, 80.6, 80.2(*2), 80.0, 78.9, 74.8, 69.8, 69.4, 68.4, 68.3, 68.2, 67.9, 57.1, 56.3, 45.7, 40.4, 39.6, 36.5, 35.1, 34.8, 34.2, 33.6, 30.5, 28.1 (*3), 27.5, 25.8 (*3), 20.2, 20.0, 19.4, 18.4, 17.9, 16.3, 16.0, 15.1, 12.9, 12.0, −4.6, −4.9

Example 56

Preparation of Compound 62

In 500 μl of tetrahydrofuran, 55.5 mg of Compound 59 was dissolved, 200 μl of the solution A was added thereto, and the mixture was stirred at room temperature for a night. Then, the mixture was treated and purified in the manners similar to those in Example 2 to give 38.0 mg of the desired compound in a 77% yield.

HR-FAB-MS: Calculated; $C_{51}H_{73}O_{13}NSi$ [M+Na]$^+$ 930.4980 Found; 930.5007 IR(KBr) $\lambda_{max}cm^{-1}$: 3439, 2966, 2931, 2372, 1714, 1635, 1456, 1381, 1161, 1120, 1072, 991 $^1$H NMR (270 MHz, CDCl$_3$, partial data) δ (ppm): 5.85 (1H, m), 5.73 (3H, m), 5.53 (1H, dd, J=2.6, 9.9 Hz), 5.47 (1H, dd, J=4.0, 6.9 Hz), 5.35 (2H, m), 4.97 (1H, m), 4.82 (1H, dd, J=6.8, 14.0 Hz), 4.75 (1H, d, J=3.0 Hz), 4.66 (2H, s), 4.61 (1H, m), 3.45 (3H, s), 3.31 (3H, s), 1.94 (3H, s), 1.86 (3H, s), 1.47 (3H, s), 1.41 (3H, d, J=6.9 Hz), 1.22 (3H, d, J=5.9 Hz), 1.12 (3H, d, J=6.9 Hz) $^{13}$C NMR (67.8 MHz, CDCl$_3$) δ (ppm): 173.7, 152.5, 139.5, 138.0, 137.9, 136.2, 135.0, 127.7, 124.7, 120.3, 118.2 (*2), 118.0, 107.2, 95.7, 94.9, 94.2, 81.9, 80.9, 80.3, 79.0, 78.8, 76.5, 74.8, 68.4 (*2), 68.3, 68.0, 67.6, 67.2, 57.0, 56.3, 45.6, 40.4, 39.7, 37.3, 36.5, 35.1, 34.7, 34.2, 30.5, 27.5, 20.1, 19.9, 19.1, 18.0, 16.3, 16.0, 15.0, 12.9, 12.0,

Example 57

Preparation of Compound 63

In 620 μl of tetrahydrofuran, 66.7 mg of Compound 61 was dissolved, 200 μl of the solution A was added thereto, and the mixture was stirred at room temperature for 19.5 nights. Then, the mixture was treated and purified in the manners similar to those in Example 2 to give 41.3 mg of the desired compound in a 69% yield.

HR-FAB-MS: Calculated; $C_{60}H_{94}O_{15}Si$ [M+Na]$^+$ 1105.6260 Found; 1105.6260 IR(KBr) $\lambda_{max}cm^{-1}$: 3435, 2970, 2931, 1714, 1647, 1454, 1385, 1248, 1155, 1118, 1063, 1003 $^1$H NMR (270 MHz, CDCl$_3$, partial data) δ (ppm): 5.84 (1H, m), 5.74 (4H, m), 5.54 (1H, dd, J=2.5, 9.9 Hz), 5.36 (2H, m), 5.13 (1H, m), 4.99 (1H, m), 4.76 (1H, d, J=3.0 Hz), 4.67 (2H, s), 4.47 (1H, d, J=5.3 Hz), 3.45 (3H, s), 3.35 (3H, s), 1.86 (3H, s), 1.48 (12H, s), 1.40 (3H, d, J=6.6 Hz), 1.24 (3H, d, J=6.3 Hz), 1.14 (3H, d, J=6.9 Hz) $^{13}$C NMR (67.8 MHz, CDCl$_3$) δ (ppm): 173.7, 165.2, 154.3, 139.5, 138.1, 137.9, 136.2, 135.1, 127.7, 124.6, 120.4, 118.9, 118.2, 118.0, 96.1, 95.7, 95.0, 81.9, 80.6, 80.3, 80.2, 79.0, 78.9, 74.8, 69.8, 69.4, 68.4, 68.3 (*2), 68.2, 67.7, 67.4, 57.1, 56.3, 53.4, 45.6, 40.4, 39.7, 36.6, 35.1, 34.8, 34.2, 33.6, 30.5, 28.1 (*3), 27.4, 20.1, 19.9, 19.4, 17.9, 16.3, 15.0, 12.9, 12.0, −4.6, −4.9

Example 58

Preparation of Compound 64

In 320 μl of tetrahydrofuran, 32.2 mg of Compound 60 was dissolved, 150 μl of the solution A was added thereto, and the mixture was stirred at room temperature for a night. Then, the mixture was treated and purified in the manners similar to those in Example 2 to give 21.1 mg of the desired compound in a 74% yield.

HR-FAB-MS: Calculated; $C_{51}H_{73}O_{13}NSi$ [M+Na]$^+$ 930.4980 Found; 930.4973 IR(KBr) $\lambda_{max}cm^{-1}$: 3448, 2968, 2931, 1733, 1638, 1456,1383,1161,1120,1068, 991 $^1$H NMR (270 MHz, CDCl$_3$, partial data) δ (ppm): 5.85 (1H, m), 5.74 (3H, m), 5.54 (1H, dd, J=2.6, 9.9 Hz), 5.46 (1H, dd, J=3.7, 6.9 Hz), 5.25 (2H, m), 5.00 (2H, m), 4.76 (1H, d, J=3.3 Hz), 4.67 (2H, s), 4.36 (1H, m), 3.46 (3H, s), 3.28 (3H, s), 2.01 (3H, s), 1.87 (3H, s), 1.52 (3H, d, J=6.9 Hz), 1.48 (3H, s), 1.24 (3H, d, J=6.3 Hz), 1.13 (3H, d, J=6.9 Hz) $^{13}$C NMR (67.8 MHz, CDCl$_3$) δ (ppm): 173.7, 152.8, 139.5, 138.1, 137.9, 136.2, 135.1, 127.7, 124.7, 120.4, 118.2, 118.0, 117.6, 106.9, 95.7, 94.9, 94.3, 81.9, 80.8, 80.4, 79.0 (*2), 74.9, 71.6, 71.4, 68.4, 68.3 (*2), 67.7, 67.3, 57.0, 56.1, 45.7, 40.4, 39.7, 36.6, 36.2, 35.1, 34.7, 34.2, 30.6, 27.5, 20.4, 20.1, 19.9, 18.0, 16.4, 16.0, 15.1,12.9, 12.0,

Example 59

Preparation of Compound 79

In 25 ml of N,N-dimethylformamide, 2.2 g of ivermectin was dissolved, 680 mg of imidazole and 750 mg of tert-butyldimethylchlorosilane were added thereto, and then the mixture was stirred at room temperature for 3 hours. An aqueous sodium hydrogencarbonate solution was added thereto, and then the mixture was extracted with dichloromethane, and the organic layer was then washed with a large quantity of purified water. The organic layer was dried over anhydrous magnesium sulfate, and the solvent was evaporated under reduced pressure to give a crude product. The crude product was purified by column chromatography on silica gel using an eluting solvent of dichloromethane/tetrahydrofuran=20/1 to give 1.6 g of the desired compound in a 63% yield and 0.4 g of the starting material in a 77% recovery.

HR-FAB-MS: Calculated; $C_{54}H_{88}O_{14}Si$ [M+Na]$^+$ 1011.5841 Found; 1011.5873 IR(KBr) $\lambda_{max}cm^{-1}$: 3450, 2963, 2931, 1714, 1635, 1456, 1381, 1254, 1120, 987 $^1$H NMR (270 MHz, CDCl$_3$, partial data) δ (ppm): 5.80 (1H, m), 5.71 (2H, m), 5.39 (1H, d, J=3.3 Hz), 5.31 (2H, m), 4.98 (1H, m), 4.77 (1H, d, J=3.0 Hz), 4.68 (1H, d, J=16.2 Hz), 4.52 (1H, d, J=16.2 Hz), 4.22 (1H, m), 3.42 (6H, s), 1.78 (3H, s), 1.50 (3H, s), 1.27 (3H, d, J=6.3 Hz), 1.25 (3H, d, J=6.0 Hz), 1.15 (3H, d, J=6.9 Hz), 0.92 (9H, s), 0.13 (6H, s) $^{13}$C NMR (67.8 MHz, CDCl$_3$) δ (ppm): 174.1, 141.2, 137.2 (*2), 135.0, 124.8, 119.3, 118.3, 117.2, 98.5, 97.5, 94.8, 81.8, 80.4, 80.2, 80.0, 79.3, 78.2, 77.5–76.5 (*1), 76.0, 69.5, 68.7, 68.1, 67.9, 67.2 (*2), 56.5, 56.4, 45.7, 41.1, 39.6, 36.8, 35.7, 35.4, 34.5, 34.1 (*2), 31.2, 28.1, 27.3, 25.8 (*3), 20.3, 20.0, 18.4, 17.6, 17.4, 15.2 (*2), 12.4, 12.1, −4.6, −4.9

Example 60

Preparation of Compound 80

Under nitrogen atmosphere, 510 mg of Compound 79 was dissolved in 1.6 ml of dimethylsulfoxide, and 720 μl of triethylamine was added thereto. Then, a solution of 670 mg of sulfur trioxide/pyridine complex dissolved in 1.0 ml of dimethylsulfoxide was added slowly and dropwise to the mixture, and the mixture was stirred at room temperature for 10 minutes.

Purified water was added thereto, and then the mixture was extracted with dichloromethane. The combined organic layer was washed with purified water and then dried over anhydrous sodium sulfate. The solvent was evaporated under reduced pressure to give a crude product. The crude product was purified by column chromatography on silica gel with an eluting solvent of hexane/ethyl acetate=4/1 to give 426 mg of the desired compound in a 84% yield.

HR-FAB-MS: Calculated; $C_{54}H_{86}O_{14}Si$ $[M+Na]^+$ 1009.5685 Found; 1009.5673 IR(KBr) $\lambda_{max}cm^{-1}$: 3455, 2960, 2860, 1740, 1635, 1456, 1379, 1253, 1174, 1122, 988 $^1H$ NMR (270 MHz, $CDCl_3$, partial data) δ (ppm): 5.80 (1H, m), 5.67 (2H, m), 5.52 (1H, br.s), 5.29 (2H, m), 4.98 (1H, m), 4.79 (1H, d, J=3.3 Hz), 4.67 (1H, d, J=14.5 Hz), 4.56 (1H, d, J=14.5 Hz), 4.40 (2H, m), 3.50 (3H, s), 3.44 (3H, s), 1.78 (3H, s), 1.51 (3H, s), 1.27 (3H, d, J=6.3 Hz), 1.27 (3H, d, J=5.9 Hz), 1.15 (3H, d, J=6.6 Hz), 0.92 (9H, s), 0.12 (6H, s) $^{13}C$ NMR (67.8 MHz, $CDCl_3$) δ (ppm): 206.0, 174.1, 140.4, 137.5, 137.3, 135.0, 124.9, 119.2, 118.4, 117.2, 98.9, 97.5, 94.8, 82.0, 81.2, 80.2, 80.0, 79.1, 78.0, 77.5−76.5 (*1), 70.8, 69.5, 68.7, 67.9, 67.2, 67.0, 58.3, 56.5, 45.8, 41.2, 39.6, 39.4, 36.9, 35.7, 35.5, 34.5, 34.1, 31.1, 28.1, 27.3, 25.9 (*3), 20.3, 20.0, 18.4, 18.3, 17.4, 15.2, 12.9, 12.4, 12.1, −4.6, −4.9

Example 61

Preparation of Compound 65

Under nitrogen atmosphere, 35 μl of allyl diethylphosphonoacetate was added to 170 μl of a 1.0 ml/L tetrahydrofuran solution of lithium hexamethyldisilazane, and the resulting mixture was stirred under ice-cooling at 0° C. for 30 minutes. Then, a solution of 98.5 mg of Compound 5 dissolved in 1.0 ml of tetrahydrofuran was added to the mixture, and the mixture was stirred at room temperature for 3 hours. The mixture was then subjected to treatment and purification in the manners similar to those in Example 1 to give 81.5 mg of the desired compound in a 78% yield.

HR-FAB-MS: Calculated; $C_{61}H_{92}O_{15}Si$ $[M+Na]^+$ 1115.6103 Found; 1115.6024 IR(KBr) $\lambda_{max}cm^{-1}$: 3425, 2964, 2929, 1718, 1649, 1456, 1377, 1161, 1120, 1076, 997 $^1H$ NMR (270 MHz, $CDCl_3$, partial data) δ (ppm): 7.77 (1H, dd, J=11.6, 15.2 Hz), 6.18 (1H, d, J=11.6 Hz), 5.96 (1H, d, J=15.2 Hz), 5.94 (1H, m), 5.74 (4H, m), 5.54 (1H, dd, J=2.3, 9.9 Hz), 5.34 (5H, m), 4.99 (1H, m), 4.77 (1H, d, J=3.3 Hz), 4.68 (3H, m), 4.57 (1H, d, J=14.8 Hz), 4.48 (2H, m), 3.47 (3H, s), 3.34 (3H, s), 1.79 (3H, s), 1.49 (3H, s), 1.40 (3H, d, J=6.3 Hz), 1.24 (3H, d, J=6.9 Hz), 1.14 (3H, d, J=6.9 Hz), 0.93 (9H, s), 0.13 (6H, s) $^{13}C$ NMR (67.8 MHz, $CDCl_3$) δ (ppm): 173.9, 166.4, 147.9, 144.1, 139.4, 137.4, 136.1, 135.1, 132.1, 127.7, 124.5, 123.7, 122.7, 119.2, 118.2, 118.0 (*2), 117.2, 96.3, 95.7, 95.0, 81.2, 80.2 (*2), 80.1, 80.0, 78.9, 74.7, 72.6, 69.4, 68.4, 68.3, 67.8, 67.3, 65.0, 56.9, 56.1, 45.7, 40.4, 39.6, 36.4, 35.1, 34.7, 34.2, 30.5, 27.4, 26.0, 25.8 (*3), 20.2, 19.9, 18.9, 18.3, 17.9, 16.3, 15.0, 12.9, 12.0, −4.7 (*2)

Example 62

Preparation of Compounds 81 and 82

Under nitrogen atmosphere, 92 μl of allyl diethylphosphonoacetate was added to 436 μl of a 1.0 ml/L tetrahydrofuran solution of lithium hexamethyldisilazane, and the mixture was stirred under ice-cooling at 0° C. for 30 minutes. Then, a solution of 254 mg of Compound 80 in 2.6 ml of tetrahydrofuran was added to the mixture, and the mixture was stirred at room temperature for 50 minutes. The mixture was then subjected to treatment and purification in the manners similar to those in Example 1 to give 234 mg of the desired compound in a 85% yield.

Compounds 81 and 82, which are isomers based on the 4"-exomethylene moiety, gave the Rf values of 0.56 and 0.52, respectively, on thin-layer chromatography using a developing solvent of toluene/ethyl acetate=7/1, and the production ratio of Compound 81 (Z): Compound 82 (E)= 1:7.

Compound 81:

HR-FAB-MS: Calculated; $C_{59}H_{92}O_{15}Si$ $[M+Na]^+$ 1091.6103 Found; 1091.6099 IR(KBr) $\lambda_{max}cm^{-1}$: 3458, 2960, 2934, 1720, 1649, 1456, 1385, 1252, 1161, 1120, 1083, 998 $^1H$ NMR (270 MHz, $CDCl_3$, partial data) δ (ppm): 5.98 (1H, m), 5.79 (1H, m), 5.70 (2H, m), 5.52 (2H, m), 5.30 (4H, m), 4.98 (1H, m), 4.70 (1H, d, J=3.0 Hz), 4.67 (1H, d, J=16.8 Hz), 4.61 (2H, d, J=5.9 Hz), 4.60 (1H, d, J=16.8 Hz), 4.42 (1H, m), 3.45 (3H, s), 3.24 (3H, s), 1.78 (3H, s), 1.50 (3H, s), 1.48 (3H, d, J=6.6 Hz), 1.24 (3H, d, J=6.3 Hz), 1.11 (3H, d, J=6.9 Hz), 0.92 (9H, s), 0.85 (3H, d, J=6.6 Hz), 0.12 (6H, s) $^{13}C$ NMR (67.8 MHz, $CDCl_3$) δ (ppm): 174.1, 164.6, 155.5, 140.1, 137.6, 137.5, 135.1, 132.0, 124.7, 119.4, 118.6, 118.3, 117.8, 117.3, 97.5, 94.8, 94.2, 81.8, 80.7, 80.4, 80.2, 80.0, 78.9, 77.5−76.5 (*1), 69.5, 68.7, 68.4, 67.9, 67.4, 67.2, 65.1, 57.1, 56.1, 45.8, 41.1, 39.7, 38.2, 36.8, 35.7, 35.5, 34.8, 34.1, 31.2, 28.1, 27.3, 25.9 (*3), 20.2, 20.0, 19.7, 18.4, 18.0, 17.4, 15.2, 12.4, 12.1, −4.6, −4.9

Compound 82:

HR-FAB-MS: Calculated; $C_{59}H_{92}O_{15}Si$ $[M+Na]^+$ 1091.6103 Found; 1091.6068 IR(KBr) $\lambda_{max}cm^{-1}$: 3450, 2960, 2933, 1724, 1651, 1458, 1385, 1250, 1163, 1122, 1087, 991 $^1H$ NMR (270 MHz, $CDCl_3$, partial data) δ (ppm): 5.95 (1H, m), 5.87 (1H, s), 5.80 (1H, m), 5.74 (2H, m), 5.45 (1H, m), 5.30 (4H, m), 5.14 (1H, m), 4.99 (1H, m), 4.77 (1H, d, J=2.6 Hz), 4.68 (1H, d, J=16.2 Hz), 4.63 (2H, d, J=5.9 Hz), 4.54 (1H, d, J=16.2 Hz), 4.50 (1H, d, J=6.6 Hz), 3.45 (3H, s), 3.37 (3H, s), 1.60 (3H, s), 1.50 (3H, s), 1.41 (3H, d, J=6.6 Hz), 1.25 (3H, d, J=6.3 Hz), 1.13 (3H, d, J=6.9 Hz), 0.93 (9H, s), 0.85 (3H, d, J=6.6 Hz), 0.13 (6H, s) $^{13}C$ NMR (67.8 MHz, $CDCl_3$) δ (ppm): 174.1, 165.4, 157.1, 140.2, 137.6, 137.5, 135.0, 132.0, 124.7, 119.3, 118.5, 118.3, 117.2, 116.7, 97.5, 96.2, 94.9, 81.8, 80.3, 80.0, 80.2, 78.9, 77.5−76.5 (*1), 70.1, 69.5, 68.7, 68.1, 67.9, 67.4, 67.2, 65.0, 57.1, 56.5, 45.7, 41.2, 39.6, 36.8, 35.7, 35.4, 34.8, 34.1, 33.4, 31.2, 28.1, 27.3, 25.9 (*3), 20.2, 20.0, 19.4, 18.4, 18.0, 17.4, 15.2, 12.4, 12.1, −4.6, −4.9

Example 63

Preparation of Compounds 83 and 84

Under nitrogen atmosphere, 37 μl of diethyl cyanomethylphosphonate was added to 232 μl of a 1.0 ml/L tetrahydrofuran solution of lithium hexamethyldisilazane, and the mixture was stirred under ice-cooling at 0° C. for 30 minutes. Then, a solution of 135 mg of Compound 80 dissolved in 1.4 ml of tetrahydrofuran was added to the mixture, and the mixture was stirred at room temperature for 1 hour. The mixture was subjected to treatment and purification in the manners similar to those in Example 1 to give 137 mg of the desired compound in a 100% yield.

Compounds 83 and 84, which are isomers based on the 4"-exomethylene moiety, gave the Rf values of 0.55 and 0.50, respectively, on thin-layer chromatography using a developing solvent of toluene/ethyl acetate=7/1, and the production ratio of Compound 83 (Z): Compound 84 (E)= 1:2.7.

Compound 83:

HR-FAB-MS: Calculated; $C_{56}H_{87}O_{13}NSi$ [M+Na]$^+$ 1032.5844 Found; 1032.5846 IR(KBr) $\lambda_{max}cm^{-1}$: 3471, 2960, 2933, 2222, 1713, 1456, 1379, 1254, 1120, 1085, 991 $^1$H NMR (270 MHz, CDCl$_3$, partial data) δ (ppm): 5.79 (1H, m), 5.72 (2H, m), 5.51 (1H, s), 5.45 (1H, m), 5.31 (2H, m), 4.98 (1H, m), 4.77 (1H, d, J=3.0 Hz), 4.68 (1H, d, J=3.0 Hz), 4.67 (1H, d, J=16.2 Hz), 4.56 (1H, d, J=16.2 Hz), 4.42 (1H, m), 3.43 (3H, s), 3.36 (3H, s), 1.79 (3H, s), 1.64 (3H, d, J=6.9 Hz), 1.50 (3H, s), 1.25 (3H, d, J=6.3 Hz), 1.14 (3H, d, J=6.9 Hz), 0.92 (9H, s), 0.85 (3H, d, J=6.6 Hz), 0.13 (6H, s) $^{13}$C NMR (67.8 MHz, CDCl$_3$) δ (ppm): 174.1, 161.8, 140.3, 137.5, 137.4, 135.0, 124.8, 119.3, 118.3, 117.2, 116.0, 97.5, 96.9, 94.8, 92.8, 81.9, 81.0, 80.2 (*2), 80.0, 79.1, 77.5–76.5 (*1), 69.5, 68.7, 67.9, 67.4, 67.2, 67.1, 56.9, 56.6, 45.7, 41.1, 39.6, 38.6, 36.8, 35.7, 35.4, 34.6, 34.1, 31.2, 28.1, 27.3, 25.8 (*3), 20.3, 20.0, 18.4 (*2), 18.2, 17.4, 15.2, 12.4, 12.1, –4.6, –4.9

Compound 84:

HR-FAB-MS: Calculated; $C_{56}H_{87}O_{13}NSi$ [M+Na]$^+$ 1032.5844 Found; 1032.5846 IR(KBr) $\lambda_{max}cm^{-1}$: 3469, 2960, 2931, 2223, 1714, 1458, 1388, 1257, 1120, 1088, 991 $^1$H NMR (270 MHz, CDCl$_3$, partial data) δ (ppm): 5.80 (1H, m), 5.70 (2H, m), 5.45 (1H, t, J=4.3 Hz), 5.36 (1H, s), 5.29 (2H, m), 4.99 (1H, m), 4.78 (1H, d, J=3.0 Hz), 4.68 (1H, d, J=14.4 Hz), 4.57 (1H, d, J=14.4 Hz), 4.35 (2H, m), 3.48 (3H, s), 3.44 (3H, s), 1.79 (3H, s), 1.51 (3H, s), 1.36 (3H, d, J=6.3 Hz), 1.24 (3H, d, J=6.6 Hz), 1.15 (3H, d, J=6.9 Hz), 0.93 (9H, s), 0.85 (3H, d, J=6.6 Hz), 0.13 (6H, s) $^{13}$C NMR (67.8 MHz, CDCl$_3$) δ (ppm): 174.1, 163.4, 140.3, 137.5, 137.4, 135.0, 124.8, 119.3, 118.3, 117.2, 116.0, 97.5, 97.0, 94.8, 94.0, 81.9, 80.7, 80.2 (*2), 80.0, 79.0, 77.5–76.5 (*1), 75.4, 69.4, 67.9, 67.2, 67.1, 67.0, 66.7, 57.8, 56.7, 45.7, 41.1, 39.6, 36.9, 36.8, 35.7, 35.4, 34.6, 31.2, 28.1, 27.3, 25.9 (*3), 20.3, 20.0, 18.4, 18.2, 17.6, 17.4, 15.2, 12.1, 12.1, –4.6, –4.9

Example 64

Preparation of Compound 66

In 1.0 ml of ethanol, 81.5 mg of Compound 65 was dissolved, 9.0 mg of sodium borohydride and 1.0 mg of tetrakis(triphenylphosphono)palladium were added thereto, and the mixture was stirred at room temperature for 2 hours. Then, the mixture was treated in a manner similar to that in Example 21. The crude product concentrated under reduced pressure was dissolved in 1.5 ml of tetrahydrofuran, 200 μl of the solution A was added thereto, and the mixture was stirred at room temperature for 4.5 hours. The mixture was then subjected to treatment and purification in the manners similar to those in Example 2 to give 25.0 mg of the desired compound in a 35% yield.

HR-FAB-MS: Calculated; $C_{52}H_{74}O_{15}$ [M+2Na—H]$^+$ 983.4745 Found; 983.4743 IR(KBr) $\lambda_{max}cm^{-1}$: 3464, 2972, 2935, 1716, 1639, 1456, 1379, 1161, 1119, 993 $^1$H NMR (270 MHz, CDCl$_3$, partial data) δ (ppm): 7.82 (1H, dd, J=11.6, 15.2 Hz), 6.19 (1H, d, J=11.6 Hz), 5.92 (1H, d, J=15.2 Hz), 5.84 (1H, m), 5.74 (3H, m), 5.54 (1H, dd, J=2.5, 9.9 Hz), 5.42 (3H, m), 4.99 (1H, m), 4.77 (1H, d, J=3.0 Hz), 4.67 (2H, s), 4.48 (1H, m), 4.29 (1H, d, J=5.9 Hz), 3.46 (3H, s), 3.35 (3H, s), 1.86 (3H, s), 1.48 (3H, s), 1.40 (3H, d, J=6.6 Hz), 1.25 (3H, d, J=5.9 Hz), 1.14 (3H, d, J=6.9 Hz) $^{13}$C NMR (67.8 MHz, CDCl$_3$) δ (ppm): 173.7, 171.2, 148.9, 141.2, 139.4, 138.1, 137.9, 136.3, 135.1, 127.7, 124.7, 123.5, 122.3, 120.4, 118.2, 118.0, 96.4, 95.7, 95.0, 81.9, 80.3 (*3), 79.1, 79.0, 74.9, 72.7, 68.4 (*3), 67.7, 67.4, 57.0, 56.2, 45.7, 40.3, 39.7, 36.6, 35.1, 34.7, 34.2, 30.9, 29.2, 27.3, 20.2, 19.9, 18.8, 18.0, 16.4, 15.1, 12.9, 12.0

Example 65

Preparation of Compound 85

In 2 ml of ethanol, 205 mg of Compound 82 was dissolved, 22.0 mg of sodium borohydride and 1.0 mg of tetrakis(triphenylphosphono)palladium were added thereto, and the mixture was stirred at room temperature for 1 hour. Then, the mixture was treated in a manner similar to that in Example 21. The crude product concentrated under reduced pressure was dissolved in 2.0 ml of tetrahydrofuran, 0.8 ml of the solution A was added thereto, and the mixture was stirred at room temperature for 5 hours. The mixture was then subjected to treatment and purification in the manners similar to those in Example 2 to give 105 mg of the desired compound in a 60% yield.

HR-FAB-MS: Calculated; $C_{50}H_{74}O_{15}$ [M+2Na—H]$^+$ 959.4745 Found; 959.4793 IR(KBr) $\lambda_{max}cm^{-1}$: 3463, 2966, 2933, 1718, 1456, 1385, 1245, 1119, 989 $^1$H NMR (270 MHz, CDCl$_3$, partial data) δ (ppm): 5.87 (1H, s), 5.84 (1H, m), 5.73 (2H, m), 5.39 (2H, m), 5.05 (1H, m), 4.97 (1H, m), 4.77 (1H, d, J=2.6 Hz), 4.67 (2H, s), 4.50 (1H, d, J=5.3 Hz), 4.29 (1H, d, J=5.9 Hz), 3.44 (3H, s), 3.38 (3H, s), 1.86 (3H, s), 1.48 (3H, s), 1.41 (3H, d, J=6.6 Hz), 1.24 (3H, d, J=6.3 Hz), 1.13 (3H, d, J=6.6 Hz), 0.92 (3H, t, J=7.3 Hz), 0.84 (3H, d, J=6.6 Hz) $^{13}$C NMR (67.8 MHz, CDCl$_3$) δ (ppm): 173.8, 169.2, 157.9, 139.4, 138.1, 137.8, 135.6, 124.7, 120.5, 118.3, 118.1, 116.8, 97.5, 96.2, 94.9, 81.7, 80.3 (*2), 79.1, 78.9, 77.5–76.5 (*1), 70.8, 68.7, 68.4, 68.0, 67.7, 67.3, 67.1, 57.0, 56.5, 45.7, 41.1, 39.7, 36.9, 35.7, 35.4, 34.7, 34.1, 33.5, 31.2, 28.0, 27.3, 20.2, 19.9, 19.1, 18.0, 17.4, 15.1, 12.4, 12.0

Example 66

Preparation of Compound 86

In 1 ml of tetrahydrofuran, 89.1 mg of Compound 84 was dissolved, 500 μl of the solution A was added thereto, and the mixture was stirred at room temperature for 4 hours. The mixture was then subjected to treatment and purification in the manners similar to those in Example 2 to give 75.0 mg of the desired compound in a 94% yield.

HR-FAB-MS: Calculated; $C_{50}H_{74}O_{15}$ [M+2Na—H]$^+$ 918.4980 Found; 918.4984 IR(KBr) $\lambda_{max}cm^{-1}$: 3438, 2966, 2935, 2362, 1718, 1450, 1381, 1178, 1119, 1059, 1012, 991 $^1$H NMR (270 MHz, CDCl$_3$, partial data) δ (ppm): 5.85 (1H, m), 5.71 (2H, m), 5.37 (3H, m), 5.35 (1H, s), 4.84 (1H, d, J=3.3 Hz), 4.66 (2H, s), 4.55 (1H, d, J=5.9 Hz), 4.43 (2H, m), 3.47 (3H, s), 3.43 (3H, s), 1.86 (3H, s), 1.49 (3H, s), 1.35 (3H, d, J=6.6 Hz), 1.23 (3H, d, J=6.3 Hz), 1.14 (3H, d, J=6.9 Hz), 0.92 (3H, t, J=7.3 Hz), 0.84 (3H, d, J=6.6 Hz) $^{13}$C NMR (67.8 MHz, CDCl$_3$) δ (ppm): 174.2, 163.8, 140.1, 138.4 (*2), 135.4, 125.2, 120.8, 118.7, 118.5, 116.5, 97.9, 97.6, 95.3, 94.4, 82.2, 81.2, 80.8, 79.5 (*2), 77.1, 75.9, 69.0, 68.9, 68.1, 67.6, 67.5, 67.1, 58.3, 57.2, 46.1, 41.6, 40.1, 37.4, 36.2, 36.0, 35.9, 35.0, 34.5, 31.6, 28.5, 27.7, 20.6, 20.4, 18.6, 18.1, 17.9, 15.6, 12.9, 12.5

Example 67

Preparation of Compound 67

In 870 ml of dichloromethane, 89.4 mg of Compound 24 was dissolved, 11.0 μl of N-acetylcysteamine, 5.0 mg of 4-dimethylaminopyridine, and 68.0 mg of benzotriazol-1-yloxytripyrrolidinophosphonium hexafluorophosphate were added thereto, and the mixture was stirred for 3 hours. A saturated aqueous ammonium chloride solution was added thereto, and then the mixture was extracted with dichloromethane. The organic layer was then washed with purified water. The organic layer was dried over anhydrous magnesium sulfate, and then the solvent was evaporated under reduced pressure to give a crude product. The crude product was purified by column chromatography on silica gel using stepwise elution with eluting solvents of dichloromethane/methanol=100/1 to 50/1 to give 80.2 mg of the desired compound in a 82% yield.

HR-FAB-MS: Calculated; $C_{60}H_{93}O_{15}NSSi$ [M+Na]$^+$ 1150.5933 Found; 1150.5890 IR(KBr) $\lambda_{max}cm^{-1}$: 3378, 2964, 2933, 1732, 1673, 1543, 1456, 1380, 1161, 1120, 1081, 981 $^1$H NMR (270 MHz, CDCl$_3$, partial data) δ (ppm): 6.08 (1H, s), 5.76 (4H, m), 5.54 (1H, dd, J=2.3, 9.9 Hz), 5.45 (1H, m), 5.34 (1H, m), 4.96 (2H, m), 4.76 (1H, d, J=3.0 Hz), 4.65 (2H, s), 4.45 (1H, d, J=5.6 Hz), 3.45 (3H, s), 3.35 (3H, s), 1.96 (3H, s), 1.79 (3H, s), 1.49 (3H, s), 1.42 (3H, d, J=6.6 Hz), 1.24 (3H, d, J=6.3 Hz), 1.13 (3H, d, J=6.9 Hz), 0.92 (9H, s), 0.13 (6H, s) $^{13}$C NMR (67.8 MHz, CDCl$_3$) δ (ppm): 189.5, 174.0, 170.3, 154.3, 140.1, 137.5 (*2), 136.2, 135.1, 127.8, 124.8, 122.8, 119.3, 118.3, 117.2, 96.1, 95.7, 95.0, 82.0, 80.3, 80.2, 80.0, 78.9, 74.8, 71.0, 69.4, 68.4, 68.3, 67.9, 67.8, 67.3, 57.0, 56.6, 45.7, 40.4, 39.6, 39.5, 36.6, 35.1, 34.7, 34.3, 33.3, 30.5, 28.9, 27.5, 25.8 (*3), 23.2, 20.2, 20.0, 19.2, 18.4, 17.9, 16.3, 15.1, 13.0, 12.0, −4.6, −4.9

Example 68

Preparation of Compound 68

In 750 μl of tetrahydrofuran, 80.2 mg of Compound 67 was dissolved, 200 μl of the solution A was added thereto, and the mixture was stirred at room temperature for a night. The mixture was then subjected to treatment and purification in the manners similar to those in Example 2 to give 47.3 mg of the desired compound in a 67% yield.

HR-FAB-MS: Calculated; $C_{54}H_{79}O_{15}NS$ [M+Na]$^+$ 1036.5068 Found; 1036.5059 IR(KBr) $\lambda_{max}cm^{-1}$: 3400, 2968, 2933, 1732, 1670, 1547, 1454, 1380, 1161, 1117, 1061, 995 $^1$H NMR (270 MHz, CDCl$_3$, partial data) δ (ppm): 6.06 (1H, s), 5.97 (1H, m), 5.82 (1H, m), 5.72 (2H, m), 5.41 (2H, m), 5.23 (1H, dd, J=2.6, 9.9 Hz), 4.94 (2H, m), 4.74 (1H, d, J=3.3 Hz), 4.68 (1H, d, J=14.5 Hz), 4.57 (1H, d, J=14.5 Hz), 4.46 (2H, m), 3.45 (3H, s), 3.33 (3H, s), 1.94 (3H, s), 1.84 (3H, s), 1.47 (3H, s), 1.39 (3H, d, J=6.6 Hz), 1.22 (3H, d, J=6.3 Hz), 1.12 (3H, d, J=6.9 Hz) $^{13}$C NMR (67.8 MHz, CDCl$_3$) δ (ppm): 189.5, 173.6, 170.3, 154.2, 139.6, 138.0, 137.8, 136.2, 135.1, 127.7, 124.6, 122.7, 120.3, 118.2, 118.0, 96.1, 95.7, 95.0, 81.9, 80.3, 80.2, 79.1, 78.9, 74.8, 70.9, 68.4, 68.3, 67.7, 67.6, 67.3 (*2), 57.0, 56.6, 45.6, 40.4, 39.7, 39.4, 36.6, 35.1, 34.7, 34.2, 33.3, 30.5, 28.4, 27.4, 23.1, 19.9, 19.2, 18.4, 17.9, 16.3, 15.0, 12.9, 12.3

Example 69

Preparation of Compound 69

Under nitrogen atmosphere, 0.10 g of Compound 13 was dissolved in 1.0 ml of dichloromethane, 1.1 ml of a n-hexane solution of diisobutylaluminium hydride was added thereto under −78° C., and the mixture was stirred for 2 hours. The reaction mixture was diluted with dichloromethane, and then the reaction was quenched by adding methanol. Celite and sodium sulfate decahydrate were added thereto, and the mixture was stirred for 1 hour. The reaction solution was filtered with suction, and the solvent was evaporated under reduced pressure to give a crude product. The crude product was purified by column chromatography on silica gel using an eluting solvent of dichloromethane/methanol=50/1 to give 63 mg of the desired compound in a 63% yield.

HR-FAB-MS: Calculated; $C_{51}H_{77}O_{14}NNa$ [M+Na]$^+$ 950.5242 Found; 950.5246 IR(KBr) $\lambda_{max}cm^{-1}$: 3450, 2966, 2931, 1732, 1458, 1383, 1188, 1119, 1049, 993 $^1$H NMR (270 MHz, CDCl$_3$, partial data) δ (ppm): 5.84 (1H, m), 5.73 (3H, m), 5.61 (1H, t, J=6.9 Hz), 5.53 (1H, dd, J=2.3, 9.9 Hz), 5.37 (3H, m), 4.97 (1H, m), 4.75 (1H, d, J=3.3 Hz), 4.66 (2H, s), 4.40 (1H, d, J=6.6 Hz), 3.52 (3H, s), 3.45 (3H, s), 3.32 (3H, s), 1.85 (3H, s), 1.47 (3H, s), 1.34 (3H, d, J=6.3 Hz), 1.24 (3H, d, J=6.3 Hz), 1.13 (3H, d, J=6.9 Hz) $^{13}$C NMR (67.8 MHz, CDCl$_3$) δ (ppm): 173.7, 141.5, 139.5, 138.1, 137.9, 136.2, 135.1, 127.7, 124.6, 123.1, 120.4, 118.2, 118.0, 96.4, 95.7, 95.0, 81.9, 80.3, 80.0, 79.1, 78.9, 74.8, 72.5, 68.4, 68.3 (*2), 67.7 (*2), 67.5, 61.7, 57.0, 55.7, 48.7, 45.6, 40.4, 39.7, 36.6, 35.1, 34.8, 34.2, 33.3, 30.5, 27.4, 20.1, 19.9, 18.7, 17.9, 16.3, 15.0, 12.9, 12.0

Example 70

Preparation of Compound 70

In 1.0 ml of dichloromethane, 0.10 g of Compound 3 was dissolved, 67 μl of N-ethyldiisopropylamine, 18 mg of 4-dimethylaminopyridine and 74 mg of p-toluenesulfonyl chloride were successively added thereto, and the mixture was stirred for 2 hours. After the reaction was completed, the solvent was evaporated under reduced pressure to give a crude product. The crude product was purified by column chromatography on silica gel with an eluting solvent of hexane/ethyl acetate=8/1 to give 0.10 g of the desired compound in a 100% yield.

IR(KBr) $\lambda_{max}cm^{-1}$: 3478, 2964, 2933, 1714, 1458, 1383, 1328, 1255, 1188, 1161, 1120, 1084, 993 $^1$H NMR (270 MHz, CDCl$_3$, partial data) δ (ppm): 5.71 (5H, m), 5.54 (1H, dd, J=2.6, 9.9 Hz), 5.36 (3H, m), 4.97 (1H, m), 4.76 (1H, d, J=3.3 Hz), 4.67 (1H, d, J=14.5 Hz), 4.46 (1H, d, J=14.5 Hz), 4.42 (2H, m), 3.45 (3H, s), 3.35 (3H, s), 1.78 (3H, s), 1.49 (3H, s), 1.35 (3H, d, J=6.3 Hz), 1.25 (3H, d, J=6.3 Hz), 1.14 (3H, d, J=6.9 Hz), 0.92 (9H, s), 0.13 (6H, s) $^{13}$C NMR (67.8 MHz, CDCl$_3$) δ (ppm): 174.0, 142.2, 140.2, 137.5 (*2), 136.1, 135.1, 127.8, 124.7, 122.7, 119.3, 118.3, 117.2, 96.6, 95.7, 95.0, 82.0, 80.2, 80.1 (*2), 79.6, 74.8, 72.8, 69.5, 68.4, 68.3, 67.9, 67.6, 67.4, 56.9, 56.1, 45.8, 40.4, 39.7 (*2), 36.5, 35.2, 34.7, 34.2 (*2), 30.5, 27.5, 25.8 (*3), 20.2, 20.0, 18.5, 18.4, 18.0, 16.3, 15.1, 12.9, 12.0, −4.6, −4.9

Example 71

Preparation of Compound 71

In 0.75 ml of tetrahydrofuran, 80 mg of Compound 70 was dissolved, 0.20 ml of the solution A was added thereto, and the mixture was stirred at room temperature for a night. The mixture was then subjected to treatment and purification in the manners similar to those in Example 2 to give 75 mg of the desired compound in a 67% yield.

HR-FAB-MS: Calculated; $C_{50}H_{73}O_{13}ClNa$ [M+Na]$^+$ 939.4637 Found; 939.4626 IR(KBr) $\lambda_{max}cm^{-1}$: 3475, 2966, 2931, 1716, 1454, 1379, 1338, 1309, 1186, 1161, 1117, 1052, 993 $^1$H NMR (270 MHz, CDCl$_3$, partial data) δ (ppm): 5.86 (1H, m), 5.70 (4H, m), 5.54 (1H, dd, J=2.6, 9.9 Hz), 5.39 (3H, m), 4.97 (1H, m), 4.76 (1H, d, J=3.0 Hz), 4.67 (2H, s), 4.41 (1H, d, J=6.3 Hz), 3.45 (3H, s), 3.35 (3H, s), 1.86 (3H, s), 1.48 (3H, s), 1.35 (3H, d, J=6.3 Hz), 1.25 (3H, d, J=5.9 Hz), 1.14 (3H, d, J=6.9 Hz) $^{13}$C NMR (67.8 MHz, CDCl$_3$) δ (ppm): 173.1, 142.2, 139.5, 138.1, 137.9, 136.3, 135.1, 127.7, 124.7, 122.8, 120.4, 118.3, 118.0, 96.6, 95.7, 95.0, 81.9, 80.4, 80.1, 79.1, 79.0, 74.9, 72.8, 68.4, 68.3 (*2), 67.7, 67.6, 67.4, 57.0, 56.1, 45.7, 40.4, 39.8 (*2), 36.6, 35.1, 34.7, 34.2, 34.1, 30.6, 27.5, 20.1, 19.9, 18.5, 18.0, 16.3, 15.1, 12.9, 12.0

Example 72

Preparation of Compound 87

In 4.9 ml of benzene, 0.10 g of Compound 24 was dissolved, 40 mg of tris(triphenylphosphine)rhodium chloride was added thereto, and then the mixture was vigorously stirred under hydrogen atmosphere at room temperature for 48 hours. After the reaction was finished, the solvent was evaporated under reduced pressure to give a crude product. The crude product was dissolved in 0.80 ml of tetrahydrofuran, 0.40 ml of the solution A was added thereto, and the mixture was stirred at room temperature for a night. The mixture was then subjected to treatment and purification in the manners similar to those in Example 2 to give 34 mg of the desired compound in a 40% yield.

HR-FAB-MS: Calculated; C$_{50}$H$_{76}$O$_{15}$Na [M+Na]$^+$ 939.5082 Found; 939.5087 IR(KBr) λ$_{max}$cm$^{-1}$: 3443, 2966, 2931, 1716, 1456, 1379, 1342, 1301, 1196, 1173, 1117, 1053, 987 $^1$H NMR (270 MHz, CDCl$_3$, partial data) δ (ppm): 5.86 (1H, m), 5.75 (2H, m), 5.40 (3H, m), 4.98 (1H, m), 4.76 (1H, d, J=3.0 Hz), 4.67 (2H, s), 4.11 (1H, d, J=6.3 Hz), 3.96 (1H, d, J=6.3 Hz), 3.42 (3H, s), 3.34 (3H, s), 1.86 (3H, s), 1.49 (3H, s), 1.23 (3H, d, J=6.6 Hz), 1.20 (3H, d, J=5.9 Hz), 1.16 (3H, d, J=6.9 Hz), 0.92 (3H, t, J=7.3 Hz), 0.84 (3H, d, J=6.3 Hz), 0.78 (3H, d, J=4.3 Hz) $^{13}$C NMR (67.8 MHz, CDCl$_3$) δ (ppm): 177.3, 173.8, 139.5, 138.0, 137.8, 135.0, 124.7, 120.4, 118.3, 118.0, 98.5, 97.5, 94.8, 81.8, 80.3, 80.0, 79.3, 79.1, 77.5–76.5 (*1), 76.1, 68.6, 68.4, 68.0, 67.7, 67.2 (*2), 56.5, 56.1, 45.7, 45.4, 41.2, 39.7, 36.9, 35.7, 35.4, 35.0, 34.5, 34.1, 33.5, 31.2, 28.0, 27.2, 20.2, 19.9, 18.9, 18.3, 17.4, 15.1, 12.4, 12.1

Example 73

Preparation of Compound 88

In 5.6 ml of benzene, 0.10 g of Compound 23 was dissolved, 52 mg of tris(triphenylphosphine)rhodium chloride was added thereto, and then the mixture was vigorously stirred under hydrogen atmosphere at room temperature for 23 hours. After the reaction was finished, the solvent was evaporated under reduced pressure to give a crude product. The crude product was purified by column chromatography on silica gel using an eluting solvent of dichloromethane/methanol=15/1 to give 44 mg of the desired compound in a 44% yield.

HR-FAB-MS: Calculated; C$_{50}$H$_{75}$O$_{13}$NNa [M+Na]$^+$ 920.5136 Found; 920.5136 IR(KBr) λ$_{max}$cm$^{-1}$: 3458, 2966, 2931, 2328, 1713, 1456, 1377, 1340, 1304, 1171, 1115, 1045, 991 $^1$H NMR (270 MHz, CDCl$_3$, partial data) δ (ppm): 5.86 (1H, m), 5.72 (2H, m), 5.38 (3H, m), 4.97 (1H, m), 4.76 (1H, d, J=3.0 Hz), 3.41 (3H, s), 3.37 (3H, s), 1.87 (3H, s), 1.51 (3H, s), 1.31 (3H, d, J=6.6 Hz), 1.23 (3H, d, J=6.3 Hz), 1.15 (3H, d, J=6.9 Hz), 0.93 (3H, t, J=7.3 Hz), 0.85 (3H, d, J=6.6 Hz), 0.78 (3H, d, J=4.3 Hz) $^{13}$C NMR (67.8 MHz, CDCl$_3$) δ (ppm): 173.8, 139.7, 137.9 (*2), 134.9, 124.7, 120.8, 120.4, 118.3, 118.0, 98.5, 97.5, 94.8, 81.8, 80.8, 80.3, 79.2, 79.0, 76.6, 73.8, 68.6, 68.4, 67.7, 67.2, 67.0, 65.1, 56.6, 55.5, 45.7, 41.1, 39.7, 39.6, 36.9, 35.7, 35.4, 34.5, 34.1, 31.2, 31.1, 28.0, 27.3, 20.2, 19.9, 18.3, 18.2, 17.4, 15.1, 12.4, 12.1, 8.4

Example 74

Preparation of Compound 72

In 1.0 ml of dimethylsulfoxide, 0.10 g of Compound 70 was dissolved, 7.5 mg of sodium azide was added thereto, and the mixture was stirred under 40° C. for 1 hour. Purified water was added thereto, and then the mixture was extracted with dichloromethane, and the organic layer was washed with purified water. The solvent was evaporated under reduced pressure to give a crude product. The resulting crude product was dissolved in 0.80 ml of tetrahydrofuran, 31 mg of tristriphenylphosphine was added thereto, and the mixture was stirred under 40° C. for 4 hours. A 30% aqueous ammonia solution was added thereto, and then the mixture was extracted with ethyl acetate. Then, the organic layer was washed with a saturated aqueous sodium hydrogencarbonate solution. The organic layer was dried over anhydrous magnesium sulfate, and then the solvent was evaporated under reduced pressure to give a crude product. The crude product was purified by column chromatography on silica gel using an eluting solvent of dichloromethane/methanol=20/1 to give 0.10 g of the desired compound in a 72% yield.

HR-FAB-MS: Calculated; C$_{56}$H$_{89}$O$_{13}$NSiNa [M+Na]$^+$ 1034.6001 Found; 1034.5950 IR(KBr) λ$_{max}$cm$^{-1}$: 3468, 2964, 2931, 1730, 1460, 1383, 1342, 1259, 1190, 1161, 1122, 1074, 995 $^1$H NMR (270 MHz, CDCl$_3$, partial data) δ (ppm) 5.80 (1H, m), 5.71 (3H, m), 5.59 (1H, t, J=6.9 Hz), 5.52 (1H, dd, J=2.3, 9.9 Hz), 5.34 (3H, m), 4.97 (1H, m), 4.74 (1H, d, J=3.3 Hz), 4.66 (1H, d, J=14.2 Hz), 4.56 (1H, d, J=14.2 Hz), 4.38 (2H, m), 3.44 (3H, s), 3.32 (3H, s), 1.77 (3H, s), 1.47 (3H, s), 1.33 (3H, d, J=6.3 Hz), 1.24 (3H, d, J=5.9 Hz), 1.12 (3H, d, J=6.9 Hz), 0.91 (9H, s), 0.11 (6H, s) $^{13}$C NMR (67.8 MHz, CDCl$_3$) δ (ppm): 173.9, 140.3, 140.1, 137.5, 137.4, 136.1, 135.1, 127.7, 126.1, 124.7, 119.3, 118.2, 117.3, 96.5, 95.7, 95.0, 81.9, 80.2, 80.0 (*2), 78.9, 74.8, 72.7, 69.4, 68.4, 68.3, 67.8, 67.5, 67.4, 56.9, 55.7, 45.7, 40.4, 39.6, 38.3, 36.4, 35.1, 34.7, 34.2, 33.3, 30.5, 27.4, 25.8 (*3), 20.2, 20.0, 18.5, 18.3, 17.9, 16.3, 15.0, 12.9, 12.0, −4.8, −4.9

Example 75

Preparation of Compound 73

In 1.0 ml of tetrahydrofuran, 71 mg of Compound 72 was dissolved, 0.30 ml of the solution A was added thereto, and the mixture was stirred at room temperature for a night. The mixture was then subjected to treatment and purification in the same manners as those in Example 2 to give 49 mg of the desired compound in a 78% yield.

HR-FAB-MS: Calculated; C$_{50}$H$_{75}$O$_{13}$NNa [M+Na]$^+$ 920.5136 Found; 920.5140 IR(KBr) λ$_{max}$cm$^{-1}$: 3495, 2968, 2931, 1734, 1456, 1381, 1340, 1309, 1190, 1161, 1119, 1066, 991 $^1$H NMR (270 MHz, CDCl$_3$, partial data) δ (ppm): 5.85 (1H, m), 5.73 (3H, m), 5.58 (1H, t, J=6.6 Hz), 5.53 (1H, dd, J=2.3, 9.9 Hz), 5.37 (3H, m), 4.98 (1H, m), 4.75 (1H, d, J=3.0 Hz), 4.65 (2H, s), 4.38 (1H, d, J=6.8 Hz), 3.44 (3H, s), 3.32 (3H, s), 1.85 (3H, s), 1.47 (3H, s), 1.33

(3H, d, J=6.3 Hz), 1.24 (3H, d, J=5.9 Hz), 1.13 (3H, d, J=6.9 Hz) $^{13}$C NMR (67.8 MHz, CDCl$_3$) δ (ppm): 173.6, 139.8, 139.5, 138.0, 137.8, 136.2, 135.1, 127.7, 127.0, 124.6, 120.3, 118.2, 118.0, 96.4, 95.7, 95.0, 81.9, 80.3, 80.0, 79.1, 79.0, 74.8, 72.5, 68.3 (*3), 67.6 (*2), 67.5, 57.0, 55.7, 45.7, 40.4, 39.7, 38.5, 36.5, 35.1, 34.8, 34.2, 33.2, 30.5, 27.4, 20.1, 19.9, 18.6, 17.9, 16.3, 15.0, 12.9, 12.0

Example 76

Preparation of Compound 74

In 0.80 ml of ethanol, 40 mg of Compound 70 was dissolved, 6.7 mg of piperazine was added thereto, and the mixture was stirred at 65° C. for 5 hours. After the reaction was completed, the solvent was evaporated under reduced pressure to give a crude product. The resulting crude product was dissolved in 2.0 ml of tetrahydrofuran, 0.30 ml of the solution A was added thereto, and the mixture was stirred at room temperature for 6 hours. The mixture was then subjected to treatment and purification in the manners similar to those in Example 2 to give 27 mg of the desired compound in a 71% yield.

HR-FAB-MS: Calculated; $C_{54}H_{82}O_{13}N_2Na$ [M+Na]$^+$ 989.5715 Found; 989.5710 IR(KBr) $\lambda_{max}$cm$^{-1}$: 3448, 2966, 2931, 1734, 1643, 1454, 1381, 1340, 1311, 1161, 1119, 1065, 993 $^1$H NMR (270 MHz, CDCl$_3$, partial data) δ (ppm): 5.81 (1H, m), 5.71 (4H, m), 5.54 (1H, dd, J=2.3, 9.9 Hz), 5.38 (3H, m), 4.97 (1H, m), 4.75 (1H, d, J=3.0 Hz), 4.67 (2H, s), 4.40 (1H, d, J=6.6 Hz), 3.45 (3H, s), 3.31 (3H, s), 1.86 (3H, s), 1.47 (3H, s), 1.35 (3H, d, J=6.3 Hz), 1.25 (3H, d, J=5.9 Hz), 1.13 (3H, d, J=6.6 Hz) $^{13}$C NMR (67.8 MHz, CDCl$_3$) δ (ppm): 173.7, 140.6, 139.6, 138.1, 138.0, 136.3, 135.2, 127.8, 124.9, 124.7, 120.4, 118.3, 118.1, 96.3, 95.8, 95.1, 81.9, 80.4, 80.2, 79.1, 78.4, 74.9, 72.2, 68.4 (*4), 67.7, 67.6, 57.1, 55.9, 55.8, 54.6 (*2), 46.0 (*2), 45.7, 40.5, 39.8, 36.6, 35.2, 34.8, 34.2, 33.4, 30.6, 27.5, 20.1, 19.9, 19.2, 18.0, 16.4, 15.1, 13.0, 12.0

Example 77

Preparation of Compound 75

In 0.50 ml of ethanol, 50 mg of Compound 70 was dissolved, and 90 μl of morpholine was added thereto, and the mixture was stirred at 65? for 4 hours. After the reaction was completed, the solvent was evaporated under reduced pressure to give a crude product. The resulting crude product was dissolved in 1.0 ml of tetrahydrofuran, 0.30 ml of the solution A was added thereto, and the mixture was stirred at room temperature for 14 hours. The mixture was then subjected to treatment and purification in the manners similar to those in Example 2 to give 47 mg of the desired compound in a 100% yield.

HR-FAB-MS: Calculated; $C_{54}H_{82}O_{14}NNa$ [M+Na]$^+$ 990.5555 Found; 990.5545 IR(KBr) $\lambda_{max}$cm$^{-1}$: 3463, 2968, 2931, 1736, 1718, 1456, 1381, 1340, 1271, 1190, 1161, 1119, 1068, 993 $^1$H NMR (270 MHz, CDCl$_3$, partial data) δ (ppm): 5.84 (1H, m), 5.72 (3H, m), 5.56 (1H, t, J=6.6 Hz), 5.53 (1H, dd, J=2.3, 9.9 Hz), 5.37 (3H, m), 4.96 (1H, m), 4.74 (1H, d, J=3.3 Hz), 4.65 (2H, s), 4.40 (1H, d, J=6.3 Hz), 3.70 (4H, m), 3.44 (3H, s), 3.30 (3H, s), 2.45 (4H, br), 1.85 (3H, s), 1.46 (3H, s), 1.34 (3H, d, J=6.3 Hz), 1.24 (3H, d, J=5.9 Hz), 1.12 (3H, d, J=6.6 Hz) $^{13}$C NMR (67.8 MHz, CDCl$_3$) δ (ppm): 173.7, 141.0, 139.5, 138.1, 137.9, 136.2, 135.1, 127.7, 124.6, 124.3, 120.3, 118.2, 118.0, 96.3, 95.7, 95.0, 81.9, 80.3, 80.1, 79.1, 78.9, 74.8, 72.2, 68.3 (*3), 68.1, 67.6, 67.5, 66.8 (*2), 57.0, 55.7, 55.6, 53.7 (*2), 45.6, 40.4, 39.7, 36.6, 35.1, 34.8, 34.2, 33.3, 30.5, 27.4, 20.1, 19.9, 19.0, 17.9, 16.3, 15.0, 12.9, 12.0

Example 78

Preparation of Compound 76

In 1.0 ml of ethanol, 50 mg of Compound 70 was dissolved, 6.0 μl of piperidine was added thereto, and the mixture was stirred at 65° C. for 3 hours. After the reaction was completed, the solvent was evaporated under reduced pressure to give a crude product. The crude product obtained was dissolved in 0.50 ml of tetrahydrofuran, 0.20 ml of the solution A was added thereto, and the mixture was stirred at room temperature for a night. The mixture was then subjected to treatment and purification in the manners similar to those in Example 2 to give 38 mg of the desired compound in a 81% yield.

HR-FAB-MS: Calculated; $C_{55}H_{84}O_{13}NNa$ [M+Na]$^+$ 988.5762 Found; 988.5768 IR(KBr) $\lambda_{max}$cm$^{-1}$: 3435, 2966, 2931, 1734, 1641, 1456, 1388, 1338, 1306, 1271, 1159, 1119, 1063, 995 $^1$H NMR (270 MHz, CDCl$_3$, partial data) δ (ppm): 5.85 (1H, m), 5.72 (3H, m), 5.56 (1H, t, J=6.6 Hz), 5.53 (1H, dd, J=2.3, 9.9 Hz), 5.37 (3H, m), 4.96 (1H, m), 4.74 (1H, d, J=3.3 Hz), 4.65 (2H, s), 4.40 (1H, d, J=6.3 Hz), 3.70 (4H, m), 3.44 (3H, s), 3.30 (3H, s), 2.45 (4H, br), 1.85 (3H, s), 1.46 (3H, s), 1.34 (3H, d, J=6.3 Hz), 1.24 (3H, d, J=5.9 Hz), 1.12 (3H, d, J=6.6 Hz) $^{13}$C NMR (67.8 MHz, CDCl$_3$) δ (ppm): 173.7, 141.0, 139.5, 138.1, 137.9, 136.2, 135.1, 127.7, 124.6, 124.3, 120.3, 118.2, 118.0, 96.3, 95.7, 95.0, 81.9, 80.3, 80.1, 79.1, 78.9, 74.8, 72.2, 68.3 (*3), 68.1, 67.6, 67.5, 66.8 (*2), 57.0, 55.7, 55.6, 53.7 (*2), 45.6, 40.4, 39.7, 36.6, 35.1, 34.8, 34.2, 33.3, 30.5, 27.4, 20.1, 19.9, 19.0, 17.9, 16.3, 15.0, 12.9, 12.0

Example 79

Preparation of Compound 77

In 0.60 ml of dichloromethane, 61 mg of Compound 72 was dissolved, 61 μl of acetic anhydride was added thereto, and the mixture was stirred at room temperature for 1 hour. A saturated aqueous sodium hydrogencarbonate solution was added thereto, and then the mixture was extracted with dichloromethane. The organic layer was then washed with purified water. The organic layer was dried over anhydrous magnesium sulfate, and then the solvent was evaporated under reduced pressure to give a crude product. The resulting crude product was dissolved in 1.2 ml of tetrahydrofuran, 0.25 ml of the solution A was added thereto, and the mixture was stirred at room temperature for a night. The mixture was then subjected to treatment and purification in the manners similar to those in Example 2 to give 39 mg of the desired compound in a 69% yield.

HR-FAB-MS: Calculated; $C_{52}H_{77}O_{14}NNa$ [M+Na]$^+$ 962.5242 Found; 962.5237 IR(KBr) $\lambda_{max}$cm$^{-1}$: 3400, 2970, 2931, 1734, 1659, 1547, 1454, 1381, 1340, 1309, 1292, 1161, 1117, 1059, 991 $^1$H NMR (270 MHz, CDCl$_3$, partial data) δ (ppm): 5.78 (4H, m), 5.53 (1H, dd, J=2.0, 9.9 Hz), 5.51 (1H, t, J=3.0 Hz), 5.37 (3H, m), 4.98 (1H, m), 4.75 (1H, d, J=3.0 Hz), 4.66 (2H, s), 4.36 (1H, d, J=6.6 Hz), 3.45 (3H, s), 3.35 (3H, s), 1.95 (3H, s), 1.85 (3H, s), 1.47 (3H, s), 1.31 (3H, d, J=6.3 Hz), 1.24 (3H, d, J=5.9 Hz), 1.13 (3H, d, J=6.6 Hz) $^{13}$C NMR (67.8 MHz, CDCl$_3$) δ (ppm): 173.7, 169.9, 142.1, 139.5, 138.1, 137.9, 136.2, 135.1, 127.7, 124.7, 123.3, 120.3, 118.2, 118.0, 96.5, 95.7, 95.0, 81.9, 80.3, 79.9, 79.1, 79.0, 74.8, 72.5, 68.4, 68.3 (*2), 67.6, 67.5, 67.0, 57.0, 56.7, 45.6, 40.4, 39.7, 36.5 (*2), 35.1, 34.7, 34.2, 32.4, 30.5, 27.4, 23.2, 20.1, 19.9, 18.3, 17.9, 16.3, 15.0, 12.9, 12.0

Example 80

Preparation of Compound 78

To 0.5 ml of a 1.0 ml/L tetrahydrofuran solution of lithium hexamethyldisilazane, 120 μl of methyl diethylphosphonoacetate was added, and the mixture was stirred under ice-cooling at 0° C. for 30 minutes. Then, a solution of 400 mg of Compound 42 dissolved in 0.8 ml of tetrahydrofuran was added to the mixture, and the mixture was stirred at room temperature for 3 hours. To the reaction solution was added a saturated aqueous ammonium chloride solution and the mixture was extracted with ethyl acetate. The ethyl acetate layer was dried over anhydrous sodium sulfate, and then the solvent was evaporated under reduced pressure to give a crude product. The crude product was dissolved in 1.5 ml of tetrahydrofuran, 0.5 ml of the solution A was added thereto, and the mixture was stirred at room temperature for a night. The mixture was subjected to post-treatment in the manners similar to those in Example 2, and the resulting crude product was purified by column chromatography on silica gel using stepwise elution with eluting solvents of hexane/2-propanol=6/1~3/1~1/1 to give 67 mg of the desired compound in a 20% yield.

IR(KBr) $\lambda_{max}$cm$^{-1}$: 3492, 2966, 2933, 1724, 1456, 1382, 1193, 1122, 1060, 1008, 985 $^1$H NMR (270 MHz, CDCl$_3$, partial data) δ (ppm): 5.82 (1H, s), 5.45–5.26 (4H, m), 5.13 (1H, s), 4.96(1H, m), 4.74 (1H, d, J=2.6 Hz), 4.66 (2H, s), 4.48(1H, q, J=5.6 Hz), 4.28 (1H, d, J=5.9 Hz), 3.71 (3H, s), 3.44 (3H, s), 3.26 (3H, s), 1.86 (3H, s), 1.13 (3H, d, J=6.6 Hz) $^{13}$C NMR (67.8 MHz, CDCl$_3$) δ (ppm): 173.5, 166.2, 156.7, 139.5, 138.0, 137.9, 135.6, 124.6, 120.3, 117.9, 117.4, 116.6, 99.6, 96.1, 94.9, 81.6, 80.3(*2), 80.2, 79.1, 78.8, 70.7, 70.1, 69.8, 68.3, 68.2, 68.1, 67.6, 67.4, 57.0, 56.4, 51.3, 45.6, 41.1, 40.7, 39.7, 36.4, 35.6, 35.0, 34.7, 34.1, 33.4, 27.2, 20.1, 19.9, 19.3, 17.9, 15.1, 13.7, 12.4, 11.7

Test Example 1

Methods for determining antiparasitic effects of the compounds disclosed according to the present invention are explained below.

As model insects for simple determination of antiparasitic and insecticidal activities, those insects are desired which can be easily obtained and bred in laboratories, and have no pathogenicity to a human. *Caenorhabditis elegans*, an unparasitic eelworm widely used in experiments of genetics, was used as a typical steam worm, and *Artemia salina* used as feed for tropical fish and named Brine shrimp, was used instead of insects.

<Preparation of *Caenorhabditis elegans* used for evaluation>

*Escherichia. coli* for the feed of *Caenorhabditis elegans* (mutant having uracil requirement) was inoculated in a seed medium for *E. coli* to which a small amount of uracil was added, and cultured with shaking at 27° C. for 1 day. A petri dish of 6 cm diameter was filled with 10 ml of an agar medium for eelworm proliferation, and the medium was solidified. Then 0.5 ml of the culture of *E. coli* was spread over the medium in the dish, and the dish was incubated at 37° C. to proliferate *E. coli*. A piece of the agar was collected with a platinum loop from a petri dish in which *Caenorhabditis elegans* successfully proliferated, and inoculated in petri dishes in which *E. coli* was proliferated. The petri dishes were incubated at 20° C. to proliferate *Caenorhabditis elegans*. Since the life of eelworm is about 2 weeks, subculture was carried out every once a week. The eelworms grown with spread on the surface of the petri dish after 3 to 5 days from subculture were used for the experiments.

<Preparation of *Artemia salina* used for evaluation>

To a buffer for *Artemia salina* (obtained by dissolving 0.24% of Tris, 2.57% of sodium chloride, 0.47% of magnesium chloride, 0.07% of potassium chloride, 0.02% of sodium carbonate, 0.64% of magnesium sulfate and 0.11% of calcium chloride in distilled water and adjusting the pH to 7.1 with hydrochloric acid), dried eggs of *Artemia salina* [Tetra Brine Shrimp Eggs, Warner Lambert Co.] were added. The noprius larvae 1 or 2 days after hatching were used for the experiments.

<Preparation of agar medium for eelworm proliferation>

Solution A was obtained by dissolving 0.3% of sodium chloride, 1.7% of bact-agar (DIFCO Co.), 0.5% of bact-peptone (DIFCO Co.) and 1.0% of yeast extract (DIFCO Co.) in distilled water.

Solution B was obtained by dissolving 0.5% of cholesterol in ethanol.

Solution C was obtained by dissolving 13.9% of calcium chloride in distilled water.

Solution D was obtained by dissolving 30.8% of magnesium sulfate heptahydrate in distilled water.

Solution E was obtained by dissolving 13.54% of KH$_2$PO$_4$ and 4.45% of K$_2$HPO$_4$ in distilled water.

The aforementioned Media A, C and D were sterilized in an autoclave at 121° C. for 20 minutes, and each solution was stored at 4° C.

The agar medium for eelworm proliferation was prepared by mixing the solutions in the following proportion: Solution A: 100 ml, Solution B: 0.1 ml, Solution C: 0.05 ml, Solution D: 0.1 ml and Solution E: 2.5 ml (without pH adjustment), and dispensing each 10 ml portion into petri dishes of 60×15 mm.

<Preparation of *E. coli* seed medium>

In distilled water, 2.0% of bact-trypton (DIFCO Co.), 0.55% of sodium chloride and 0.001% of uracil (SIGMA Co., pH 7.4) were dissolved, and the solution was sterilized in an autoclave at 121° C. for 20 minutes.

<Experimental procedure>

Each well of a 96 well microplate was filled with the solution of the test compound (methanol as a solvent), and the solvent was removed using a vacuum pump, then 250 μl of the assay medium was added to each wells (the assay medium was prepared by dissolving 7.5 mM sodium hydrogencarbonate, 7.5 mM potassium chloride, 7.5 mM calcium chloride dihydrate and 7.5 mM magnesium sulfate heptahydrate in distilled water and adding 0.01% of lecithin thereto), and then the microplate was shaken using a microplate mixer for 15 minutes. To each well, a few individuals of *Caenorhabditis elegans* were added by softly rubbing the surface of the agar using a toothpick, or a few individuals of *Artemia salina* were added together with 50 μl of the buffer. The microplate was incubated at 20° C., and then the insects were observed after 24 and 48 hours under a microscope (magnification of 40×). The results were compared to those obtained without addition of the test compound, and evaluated by 4 grades.

The evaluation results were shown by indications of 4 grades from 0 to 3.

3: No movement

2: Between 1 and 3

1: A little week movements

0: Active movements

Of the 4 grades, Indications 3 and 2 were judged as effective, and Indications 1 and 0 as ineffective. The results are shown in Table 9. In Table 9, the values for each compound are minimum inhibitory concentrations (MIC) which were required to give Indication 2 (or 3) for *Caenorhabditis elegans* or *Artemia salina*. In Table 9, *Caenorhabditis elegans* and *Artemia salina* are abbreviated as C.E. and A.S., respectively.

TABLE 9

| Compound No. | C.E. (μg/ml) | A.S.(μg/ml) |
|---|---|---|
| 1 | 100 | 100 |
| 2 | 0.01 | 0.01 |
| 3 | 100 | 20 |
| 4 | 0.01 | 0.01 |
| 5 | 100 | 100 |
| 6 | >100 | ≧100 |
| 7 | 0.01 | 0.002 |
| 8 | 0.01 | 0.01 |
| 9 | 0.01 | 0.002 |
| 10 | 0.01 | 0.002 |
| 11 | 0.05 | 0.01 |
| 12 | 0.01 | 0.01 |
| 13 | 0.01 | 0.002 |
| 14 | 100 | 5 |
| 17 | 100 | 100 |
| 20 | 0.01 | 0.002 |
| 21 | 0.01 | 0.002 |
| 22 | 0.01 | 0.0005 |
| 23 | 0.0005 | 0.0005 |
| 25 | 0.05 | 0.01 |
| 26 | 0.05 | 0.01 |
| 27 | 0.01 | 0.0005 |
| 30 | 0.05 | 0.01 |
| 31 | 0.05 | 0.01 |
| 34 | 0.002 | 0.002 |
| 36 | 0.01 | 0.002 |
| 37 | 0.05 | 0.01 |
| 41 | 0.01 | 0.01 |

Test Example 2

In vivo experiments with *Heterakis spumosa*

For the experiments male mice (strain Bor CFW, 25–30 g of body weight on receipt) were housed in Macrolon cages (3 mice per cage) and provided with water and SNIFF rat feed (10-mm pellets) ad libitum. Mice were infected with *H. spumosa* by oral application of 90 embryonated eggs. The eggs were obtained from female Heterakis. isolated from mouse colon 40 days after infection followed by additional three weeks incubation at 37° C. The mice were treated orally 4 times with the compounds at the dosages of 1, 0.5, 0.25, 0.1, 0.05 and 0.025 mg/kg between days 46 and 49 after infection. Compounds were suspended in Cremophor EL. Infected control mice served as untreated controls which only received Cremophor EL. Mice were killed eight days after treatment (i.e. on day 57 after infection) with carbon dioxide and cecum and colon were dissected. The number of worms which have resided in the cecum and colon were counted macroscopically. The ratios of the number of expelled worms in percent of the total number of worms was defined as level of the anthelmintic activity. Activity was evaluated on a scale 0–3 where 3 represents cure (no parasites detectable), 2 effective (<20% of parasites remaining), 1 trace effect (< of parasites remaining) and 0 ineffective (>50% of parasites remaining).

The results are shown below.

Compound 2: 1, 0.5, 0.25, 0.1 mg/kg (Score 3) 0.05 mg/kg (Score 2)

Compound 23: 0.1 mg/kg (Score 3), 0.05 mg/kg (Score 2)

Compound 31: 1, 0.5 mg/kg (Score 3), 0.25, 0.1 mg/kg (Score 2)

Compound 64: 1 mg/kg (Score 3) 0.5, 0.25, 0.1 0.05 mg/kg (Score 2)

Compound 85: 1, 0.5, 0.25, 0.1 mg/kg (Score 3) 0.05 mg/kg (Score 2)

Test Example 3

In vivo experiments with *Nematospiroides dubius*

Male mice (species and conditions are the same as those in Test Example 2) were orally infected with 60 numbers of dubius larvae. 14 days after infection the mice were orally treated 4 times with the compounds using the same dosages (dose: 1, 0.5, 0.25, 0.1 mg/kg), and killed eight days after treatment. Calculation of the level of anthelmintic activity was performed in the same way as for Test Example 2.

The results are shown below.

Compound 58: 1, 0.5 mg/kg (Score 3)

Test Example 4

Blowfly larvae test/Development-inhibiting activity

Test animals: *Lucilia cuprina* larvae

Solvent: Dimethylsulfoxide 20 mg of active compound are dissolved in one ml of dimethylsulfoxide. In order to prepare a suitable formulation the active compound solution is diluted with water to the concentration required in each case.

Approx. 20 *Lucilia cuprina* larvae are introduced into a test tube containing approx. 1 cm$^3$ of horse-meat and 0.5 ml of the active compound preparation to be tested. After 48 hours the activity of the active compound preparation is determined. The test tubes are transferred to beakers with a sand-covered base. After a further 2 days the test tubes are removed and the pupae counted.

The activity of the active compound preparation is assessed according to the number of flies which have hatched after 1.5 times the development period of an untreated control. 100% means that no flies have hatched: 0% means that all of the flies have hatched normally.

The results are shown below.

Compound 7: 100, 10, 1 ppm (100%)

Compound 21: 100, 10, 1 ppm (100%)

Compound 64: 100, 10, 1 ppm (100%)

Compound 87: 100, 10, 1, 0.1 ppm (100%)

Compound 88: 100, 10, 1 ppm (100%)

Test Example 5

Test on cat fleas/oral absorption

Test animals: Adult *Ctenocephalides felis*

Solvent: Dimethylsulfoxide (DMSO)

In order to prepare a suitable formulation a solution of active compound is prepared from 20 mg of active compound and 1 ml of DMSO. 20 μl of this formulation are added to 4 ml of citrated cow's blood and stirred.

20 starved adult fleas (of "Georgi" species of *Ctenocephalides felis*) are introduced into a chamber (of a diameter of 5 cm) which is sealed with gauze at the top and bottom. A metal cylinder, whose base is sealed with parafilm, is placed on the chamber. The cylinder contains the 4 ml of the blood/active compound formulation, which can be imbibed by the fleas through the parafilm membrane. Whereas the blood is heated to 37° C. a temperature of 25° C. is adjusted in the region of the flea chambers. Controls are mixed with the same volume of DMSO without the addition of any of the compounds. The test are repeated three times.

After 24 hours the mortality is determined in %.

Compounds which produce an at least 25% mortality rate of fleas within 24 hours are rated as being effective.

The results are shown below.

Compound 2: 100 ppm (100%), 10 ppm (50%)

Compound 4: 100 ppm (100%), 10 ppm (42%)

Compound 7: 100 ppm (99%), 10 ppm (61%)

Compound 23: 100 ppm (100%), 10 ppm (100%), 1 ppm (31%)

Compound 25: 100 ppm (100%), 10 ppm (69%)

Compound 58: 100 ppm (100%), 10 ppm (73%)

Compound 88: 100 ppm (100%), 10 ppm (61%)

Test Example 6

Filter test on flies (*Musca domestica*)—ingestion/contact method

Test animals: Adult *Musca domestica* of WHO(N) species

Solvent: DMSO

In order to prepare a suitable formulation a solution of active compound is prepared froom 20 mg of active compound and 1 ml of DMSO. The active compound solution is diluted with water to the concentration required in each case.

2 ml of this preparation of active compound are pipetted onto filter paper discs (of a diameter of 9.5 cm) contained in Petri dishes of the appropriate size. After drying the filter discs, 100 μl of the active compound formulation and 400 μl of a sugar solution are poured onto a block of household sponge cloth measuring 1 cm² and placed in a blister well on the filter disc. 25 $CO_2$-intoxicated test animals are transferred to the Petri dishes and covered.

After 1, 3, 5 and 24 hours the activity of the active compound preparation is determined. 100% means that all of the flies have been destroyed; 0% means that none of the flies have been destroyed.

The results are shown below.

Compound 26: 100 ppm (100%), 10 ppm (75%)

Compound 69: 100 ppm (100%), 10 ppm (50%)

Compound 85: 100 ppm (95%), 10 ppm (75%)

Compound 87: 100 ppm (100%), 10 ppm (100%), 1 ppm (80%)

Test Example 7

Test on cockroaches—ingestion/contact method

Test animals: Fourth larval stage of *Periplaneta americana*

Solvent: Dimethylsulfoxide 20 mg of active compound are dissolved in one ml of dimethylsulfoxide. For the purpose of preparing a suitable formulation the active compound solution is diluted with water to the concentration required in each case.

5 ml of this solution of active compound are pipetted onto baking wafers (of a diameter of 9 cm) contained in Petri dishes of the appropriate size. After drying the wafers 5 cockroach larvae are intoxicated with $CO_2$, transferred to the Petri dishes and covered.

After 1 and 7 days the activity of the active compound formulation is determined.

100% means that all of the cockroach larvae have been destroyed; 0% means that none of the cockroach larvae have been destroyed.

The result is shown below.

Compound 62: 100 ppm (75%)

Test Example 8

Test on cockroached—Immersion process

Test animals: Third larval stages of *Periplaneta americana*

Solvent: Dimethylsulfoxide 20 mg of active compound are dissolved in one ml of dimethylsulfoxide. In order to prepare a suitable formulation the solution of active compound is diluted with water to the concentration required in each case.

20 ml of this preparation of active compound are pipetted into tubes (of a diameter of 1.5 cm and a height of 10 cm). 4 cockroach larvae are intoxicated with $CO_2$ and transferred to a tube (of a diameter of 1.2 cm and a height of 9 cm) containing 3 holes (in the base and 5 cm below the upper rim). The tube is sealed with a stopper and kept at room temperature for 30 minutes until all of the cockroach larvae again display normal activity. The tube is immersed in the active compound formulation for 60 seconds, during which period all of the cockroach larvae are completely coverd. After the liquid has drained off the cockroach larvae are transferred to filter discs in cans made of PP (of a diameter of 9.7 cm and a height of 8 cm height).

After 2 and 24 hours and after 7 days the activity of the active compound formulation is determined. 100% means that all of the cockroach larvae have been destroyed; 0% means that none of the cockroach larvae have been destroyed.

The results are shown below.

Compound 62: 100 ppm (100%), 10 ppm (100%), 1 ppm (75%)

Compound 64: 100 ppm (100%), 10 ppm (100%)

Compound 66: 100 ppm (100%), 10 ppm (100%), 1 ppm (75%)

Compound 75: 100 ppm (100%), 10 ppm (100%), 1 ppm (50%)

Compound 78: 100 ppm (100%), 10 ppm (50%), 1 ppm (50%)

Compound 85: 100 ppm (100%), 10 ppm (100%), 1 ppm (25%)

Compound 87: 100 ppm (100%), 10 ppm (100%), 1 ppm (75%)

INDUSTRIAL APPLICABILITY

According to the present invention, avermectin derivatives having antiparasitic activity and salts thereof are provided. The aforementioned derivatives and salts thereof are useful as active ingredients of antiparasitic agents.

What is claimed is:
1. A compound represented by formula (I) or a salt thereof:

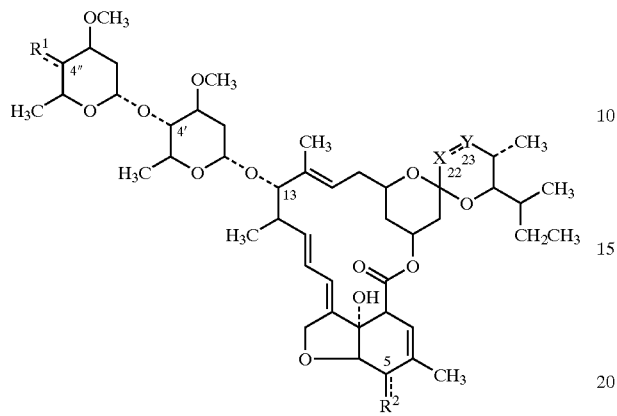

(I)

wherein —X----Y— represents —CH=CH—, —CH$_2$—C(=O)—, —CH$_2$—CH$_2$—, or —CH$^2$—CH(R$^{13}$)—;
- ---- between R$^1$ and a carbon atom at the 4"-position represents a single or double bond;
- ---- between R$^2$ and a carbon atom at the 5-position represents a single or double bond, with the provisos that
  1) when —X----Y— represents —CH=CH— and ---- between R$^1$ and a carbon atom at the 4"-position represents a double bond;
     R$^1$ represents (R$^{11}$)(R$^{12}$)C wherein R$^{11}$ represents a lower alkyl group (optionally substituted with from 1 to 3 members selected from the group consisting of a hydroxyl group, a halogen atom, an amino group, a hydroxyamino group, a mono(lower alkyl)amino group, a mono(lower alkoxy)amino group, an alkanoylamino group, an azide group, a heterocyclic group, a lower alkanoyloxy group, a heterocyclic carbonyloxy group where the heterocyclic moiety may be substituted with a halogen atom or a lower alkoxycarbonyl group, and a heterocyclic oxy group); a formyl group; a lower alkoxycarbonyl group, the alkyl moiety of which is optionally substituted with a heterocyclic group; —CH=N—OR$^3$ wherein R$^3$ represents a hydrogen atom or a lower alkyl group; a lower alkenyloxycarbonyl group; —CH=N—NH—CONH$_2$; a cyano group; —COR$^4$ wherein R$^4$ represents a hydroxyl group or N(R$^5$)(R$^6$) wherein R$^5$ and R$^6$ form a nitrogen-containing heterocyclic group together with the adjacent nitrogen atom; a vinyl group substituted with a lower alkenyloxycarbonyl group; —CO—S—CH$_2$—CH$_2$—NH—CO—R$^x$ wherein R$^x$ represents a lower alkyl group; or —CH=CH—COOH; and R$^{12}$ represents a hydrogen atom, except that when R$^{11}$ represents a cyano group, R$^{12}$ represents a hydrogen atom or a lower alkyl group; when ---- between R$^2$ and a carbon atom at the 5-position represents a single bond, R$^2$ represents a hydroxyl group, a lower alkoxyl group, or a tri(lower alkyl)silyloxy group; and when ---- between R$^2$ and a carbon atom at the 5-position represents a double bond, R$^2$ forms a carbonyl group or a hydroxime group together with the carbon atom at the 5-position;

2) when —X----Y— represents —CH$_2$—C(=O)—,
     ---- between R$^1$ and a carbon atom at the 4"-position represents a double bond;
     R$^1$ represents (R$^{11a}$)R$^{12a}$)C wherein R$^{11a}$ represents a lower alkoxycarbonyl group, the alkyl moiety of which is optionally may be substituted with a heterocyclic group, or —COOCH$_2$CH=CH$_2$; and R$^{12a}$ represents a hydrogen atom; ---- between R$^2$ and a carbon atom at the 5-position represents a single bond; and R$^2$ represents a hydroxyl group, a lower alkoxy group, or a tri(lower alkyl)silyloxy group;

3) when —X----Y— represents —CH$_2$—CH$_2$—,
     R$^1$ represents (R$^{11b}$)(R$^{12b}$)C wherein R$^{11b}$ represents a cyano group, a carboxyl group, or a lower alkenyloxycarbonyl group; and R$^{12b}$ represents a hydrogen atom; or when ---- between R$^1$ and a carbon atom at the 4"-position represents a single bond, R$^1$ represents a carboxymethyl group or a cyanomethyl group; ---- between R$^2$ and a carbon atom at the 5-position represents a single bond; and R$^2$ represents a hydroxyl group, a lower alkoxy group, or a tri(lower alkyl)silyloxy group;

4) when —X----Y— represents —CH$_2$—CH(R$^{13}$)—, and ---- between R$^1$ and a carbon atom at the 4"-position represents a double bond;
     R$^1$ represents (R$^{11c}$)(R$^{12c}$)C wherein R$^{11c}$ represents a cyano group, a carboxyl group, a lower alkoxycarbonyl group or a lower alkenyloxycarbonyl group; and R$^{12c}$ represents a hydrogen atom; R$^{13}$ represents a hydroxyl group or a lower alkylcarbonyloxy group; ---- between R$^2$ and a carbon atom at the 5-position represents a single bond; and R$^2$ represents a hydroxyl group, a lower alkoxy group or a tri(lower alkyl)silyloxy group.

2. The compound or the salt thereof according to claim 1 wherein —X----Y— is —CH=CH—.

3. The compound or the salt thereof according to claim 2 wherein R$^{11}$ represents said optionally substituted lower alkyl group, a cyano group, or said —COR$^4$.

4. The compound or the salt thereof according to any one of claims 1 to 3 wherein R$^2$ is hydroxyl group or a tri(lower alkyl)silyloxy group.

5. The compound or the salt thereof according to claim 1 wherein —X----Y— is —CH$_2$—CH$_2$—.

6. The compound or the salt thereof according to claim 5 wherein R$^{11b}$ is a cyano group or a carboxyl group.

7. A medicament which comprises as an active ingredient the compound or the physiologically acceptable salt thereof according to claim 4.

8. A method for therapeutic treatment of parasitosis which comprises the step of administering to a mammal including a human a therapeutically effective amount of the compound or the physiologically acceptable salt thereof according to claim 4.

9. An agent for the therapeutic treatment of parasitosis which comprises as an active ingredient the compound or the physiologically acceptable salt thereof according to claim 4.

* * * * *

UNITED STATES PATENT AND TRADEMARK OFFICE
CERTIFICATE OF CORRECTION

PATENT NO. : 6,605,595 B1
DATED : August 12, 2003
INVENTOR(S) : Satoshi Omura et al.

It is certified that error appears in the above-identified patent and that said Letters Patent is hereby corrected as shown below:

Title page,
Item [56], References Cited, U.S. PATENT DOCUMENTS, "4,83 3,168 5/1989 Wyuatt, Jr." should read -- 4,833,168 5/1989 Wyvratt, Jr. --.
OTHER PUBLICATIONS, "Shin, et al.," should read -- Shih, et al., --.
Item [57], ABSTRACT,
Lines 3, 5 and 13, "—X----Y—" should read -- —X----Y— --.

Column 1,
Lines 55 and 61, "—X----Y—" should read -- —X----Y— --; and
Lines 57, 59 and 62, "----" should read -- ---- --.

Column 2,
Lines 14, 18, 24, 30, 39, 42, 47 and 54, "----" should read -- ---- --; and
Lines 23, 35, 46, 60 and 63, "—X----Y—" should read -- —X----Y— --.

Column 3,
Lines 6, 39, 42, 47, 53 and 61, "—X----Y—" should read -- —X----Y— --;
Lines 33, 40, 48, 54 and 63, "----" should read -- ---- --.

Column 6,
Line 10, "alkyl)silyl-4",23-dioxoavermectin" should read
--alkyl)silyl-4, 23-dioxoavermectin--; and
Line 31, "—X----Y—" should read -- —X----Y— --.

Column 7,
Line 32, "—$X^1$----" should read -- —$X^1$---- --;
Line 50, "—X----Y—" should read -- —X----Y— --; and
Line 54, "—X----" should read -- —X---- --.

Column 8,
Line 53, "—X----Y—" should read -- —X ----Y— --.

Column 9,
Line 54, "—$X^{1a}$----$Y^{1a}$—" should read -- —$X^{1a}$----$Y^{1a}$— --; and
Line 59, "—$X^1$----$Y^1$" should read -- —X----Y— --.

Column 11,
Line 12, "—X----Y—" should read -- —X----Y— --.

UNITED STATES PATENT AND TRADEMARK OFFICE
CERTIFICATE OF CORRECTION

PATENT NO. : 6,605,595 B1
DATED : August 12, 2003
INVENTOR(S) : Satoshi Omura et al.

It is certified that error appears in the above-identified patent and that said Letters Patent is hereby corrected as shown below:

Column 12,
Line 1, "—$X^{1a}$----$Y^{1a}$—" should read -- —$X^{1a}$$\underline{\phantom{----}}$$Y^{1a}$— --.

Column 13,
Line 22, "—X----Y—" should read -- —X$\underline{\phantom{----}}$Y— --; and
Line 57, "—$X^{1a}$----$Y^{1a}$—" should read -- —$X^{1a}$$\underline{\phantom{----}}$$Y^{1a}$— --.

Column 16,
Line 8, "—X----Y—" should read -- —X$\underline{\phantom{----}}$Y— --.

Column 17,
Line 1, "—$X^{1a}$----" should read -- —$X^{1a}$$\underline{\phantom{----}}$ --.

Column 18,
Line 21, "—X----Y—" should read -- —X$\underline{\phantom{----}}$Y— --.

Column 19,
Line 26, "—$X^{1a}$----$Y^{1a}$—" should read -- —$X^{1a}$$\underline{\phantom{----}}$$Y^{1a}$— --.

Column 20,
Line 36, "—X----Y—" should read -- —X$\underline{\phantom{----}}$Y— --.

Column 21,
Line 31, "—$X^{1a}$----$Y^{1a}$—" should read -- —$X^{1a}$$\underline{\phantom{----}}$$Y^{1a}$— --.

Column 22,
Line 35, "—X----Y—" should read -- —X$\underline{\phantom{----}}$Y— --.

Column 23,
Line 27, "—$X^{1a}$----$Y^{1a}$—" should read -- —$X^{1a}$$\underline{\phantom{----}}$$Y^{1a}$— --.

Column 24,
Line- 35, "—X----Y—" should read -- —X$\underline{\phantom{----}}$Y— --.

Column 25,
Line 31, "—$X^{1a}$----$Y^{1a}$—" should read -- —$X^{1a}$$\underline{\phantom{----}}$$Y^{1a}$— --.

Column 26,
Line 50, "—X----Y—" should read -- —X$\underline{\phantom{----}}$Y— --.

UNITED STATES PATENT AND TRADEMARK OFFICE
CERTIFICATE OF CORRECTION

PATENT NO. : 6,605,595 B1
DATED : August 12, 2003
INVENTOR(S) : Satoshi Omura et al.

It is certified that error appears in the above-identified patent and that said Letters Patent is hereby corrected as shown below:

Column 27,
Line 52, "—$X^1$----$Y^1$—" should read -- —$X^1$----$Y^1$— --.

Column 28,
Line 64, "—X----Y—" should read -- —X----Y— --.

Column 30,
Line 65, "(ivermectin" should read -- (avermectin --.

Column 31,
Line 67, "—X----Y—" should read -- —X----Y— --.

Column 35,
Lines 40, 48, 59 and 62, "—X----Y—" should read -- —X----Y— --.

Column 64,
Line 56, "dioxoavarmectin" should read -- dioxoavermectin --.

Column 67,
Line 38, "dichloromethane" should read -- dichloromethane. --.

Column 72,
Line 12, "phophonate" should read -- phosphonate --.

Column 73,
Line 50, "12.0," should read -- 12.0 --.

Column 74,
Line 35, "12.0," should read -- 12.0 --.

Column 83,
Line 44, "65?" should read -- 65 ° C --.

Column 89,
Line 21, "froom" should read -- from --.

Column 90,
Line 10, "cockroached" should read -- cockroaches --.

UNITED STATES PATENT AND TRADEMARK OFFICE
CERTIFICATE OF CORRECTION

PATENT NO. : 6,605,595 B1
DATED : August 12, 2003
INVENTOR(S) : Satoshi Omura et al.

It is certified that error appears in the above-identified patent and that said Letters Patent is hereby corrected as shown below:

Column 91,
Lines 23 and 30, "—X----Y—" should read -- —X----Y— --; and
Lines 25, 27, 59 and 63, "----" should read -- ---- --.

Column 92,
Lines 1, 14, 26, 40 and 49, "—X----Y—" should read -- —X----Y— --; and
Lines 2, 8, 18, 21, 27 and 35, "----" should read -- ---- --.

Signed and Sealed this

Twenty-fourth Day of August, 2004

JON W. DUDAS
*Director of the United States Patent and Trademark Office*